US005726035A

United States Patent [19]
Jay et al.

[11] Patent Number: 5,726,035
[45] Date of Patent: Mar. 10, 1998

[54] RECOMBINANT PRODUCTION OF MAMMALIAN CALCIUM CHANNEL GAMMA SUBUNITS

[75] Inventors: Scott David Jay, Iowa City, Iowa; Steven Bradley Ellis; Michael Miller Harpold, both of San Diego, Calif.; Kevin Peter Campbell, Iowa City, Iowa

[73] Assignees: SIBIA Neurosciences, Inc., La Jolla, Calif.; University of Iowa Research Foundation, Iowa City, Iowa

[21] Appl. No.: 336,257

[22] Filed: Nov. 7, 1994

Related U.S. Application Data

[63] Continuation of Ser. No. 482,384, Feb. 20, 1990, Pat. No. 5,386,025.

[51] Int. Cl.$^6$ .................... C12N 15/12; C07K 14/435
[52] U.S. Cl. .................. 435/69.1; 435/325; 435/252.3; 435/254.11; 435/6; 536/23.5; 536/24.31; 514/44
[58] Field of Search .................... 536/23.5, 24.31; 435/69.1, 240.2, 252.3, 254.11, 6, 325; 514/44

[56] References Cited

U.S. PATENT DOCUMENTS

| | | | |
|---|---|---|---|
| 4,788,135 | 11/1988 | Davis et al. | 435/6 |
| 4,912,202 | 3/1990 | Campbell et al. | 530/388.22 |
| 4,950,739 | 8/1990 | Cherksey et al. | 530/350 |
| 4,954,436 | 9/1990 | Froehner et al. | 424/1.49 |
| 5,024,939 | 6/1991 | Gorman | 435/69.1 |
| 5,051,403 | 9/1991 | Miljanich et al. | 514/12 |
| 5,189,020 | 2/1993 | Miljanich et al. | 514/12 |
| 5,264,371 | 11/1993 | Miljanich et al. | 436/503 |
| 5,424,218 | 6/1995 | Miljanich et al. | 436/503 |
| 5,643,750 | 7/1997 | Spreyer et al. | 435/69.1 |

FOREIGN PATENT DOCUMENTS

| | | |
|---|---|---|
| 2085502 | 2/1993 | Canada . |
| 0507170 | 3/1992 | European Pat. Off. . |
| 8907608 | 8/1989 | WIPO . |
| 8909834 | 10/1989 | WIPO . |
| 9202639 | 2/1992 | WIPO . |
| 9304083 | 3/1993 | WIPO . |
| 9308469 | 4/1993 | WIPO . |
| 9314098 | 7/1993 | WIPO . |

OTHER PUBLICATIONS

Bosse et al., The cDNA and deduced amino acid sequence of the γ subunit of the L-type calcium channel from rabbit skeletal muscle, *FEBS Letters* 267(1):153–156 (1990).
Spedding et al., "Calcium Antgonists': A Class of Drugs with a Bright Future." Part II. Determination of Basic Pharmacological Properties, *Life Sciences* 35:575–587 (1984).
Kim, et al., "IgG from patients with Lambert–Eaton syndrome blocks voltage–dependent calcium channels," *Science*, 239: 405–408 (1988).
Claudio, et al., "Genetic reconstitution of functional acetylcholine receptor channels in mouse fibroblasts," *Science*, 238: 1688–1694 (1987).
Tanabe, et al., "Primary structure of the receptor for calcium channel blockers from skeletal muscle," *Nature*, 328: 313–318 (1987).
Nakayama, et al., "Purification of a putative $Ca^{2+}$ channel protein from rabbit skeletal muscle," *J.Biol.Chem.*, 262: 6572–6576 (1987).
Vaghy, et al., "Identification of a novel 1,4–dihydropyridine– and phenylalkylamine–binding polypeptide in calcium channel preparations," *J. Biol. Chem.*, 262(29): 14337–14342 (1987).
Leung, et al., "Structural characterization of the 1,4–dihydropyridine receptor of the voltage–dependent $Ca^{2+}$ channel from rabbit skeletal muscle," *J.Biol.Chem.*, 262(17): 7943–7946 (1987).
Sharp, et al., "Identification and characterization of the dihydropyridine–binding subunit of the skeletal muscle dihydropyridine receptor," *J.Biol.Chem.*, 62(25): 12309–12315 (1987).
Takahashi, et al., "Subunit structure of dihydropyridine–sensitive calcium channels from skeletal muscle," *Proc.Natl.Acad.Sci. (USA)*, 84: 5478–5482 (1987).
Morton et al. "Monoclonal antibody identifies a 200–kDA subunit of the dihydropyridine–sensitive calcium channel," *J.Biol.Chem.*, 262(25): 11904–11907 (1987).
Barhanin, et al., "The calcium channel antagonists receptor from rabbit skeletal muscle: reconstitution after purification and subunit characterization," *Eur. J. Biochem.*, 164: 525–531 (1987).
Sieber, et al., "The 165–kDa peptide of the purified skeletal muscle dihydropyridine receptor contains the known regulatory sites of the calcium channel,"0 *Eur.J.Biochem.*, 167: 117–122 (1987).
Lang, et al., "The effect of myasthenic syndrome antibody on presynaptic calcium channels in the mouse," *J.Physiol.*, 390: 257–270 (1987).
Leung, et al., "Monoclonal antibody characterization of the 1,4–dihydropyridine receptor of rabbit skeletal muscle," *Ann.N.Y.Acad.Sci.*, 522: 43–46 (1988).
Vaghy, et al., "Mechanism of action of calcium channel modulator drugs," *Ann.N.Y.Acad.Sci.*, 522: 176–186 (1988).
Noda, et al., "Existence of distinct sodium channel messenger RNAs in rat brain," *Nature*, 320: 188–192 (1986).
Noda, et al., "Expression of functional sodium channels from cloned cDNA," *Nature*, 322: 826–828 (1986).
Mierendorf, et al., "Gene isolation by screening kgt11 libraries with antibodies," *Methods in Enz.*, 152: 458–469 (1986).
Gustin, et al., "Ion channels in yeast," *Science*, 233: 1195–1197 (1986).

(List continued on next page.)

*Primary Examiner*—David L. Fitzgerald
*Attorney, Agent, or Firm*—Stephanie L. Seidman; Brown Martin Haller & McClain

[57] ABSTRACT

Calcium channel γ-subunit-encoding cDNAs, and related compositions and methods, are provided.

43 Claims, 53 Drawing Sheets

OTHER PUBLICATIONS

Curtis, et al., "Purification fo the calcium antagonist receptor of the voltage-sensitive calcium channel from skeletal muscle transverse tubule," *Biochemistry*, 23(10): 2113-2118 (1984).

Striessnig, et al., "Photoaffinity labelling of the phenylalkylamine receptor of the skeletal muscle transverse-tubule calcium channel," *FEBS Letters*, 212(2):247-253 (1987).

Borsotto, et al., "The 1,4-dihydropyridine receptor associated with the skeletal muscle voltage-dependent $Ca^{2+}$ channel," *J.Biol.Chem.*, 260(26): 14255-14263 (1985).

Cooper, et al., "Purification and characterization of the dihydropyridine-sensitive voltage-dependent calcium channel from cardiac tissue," *J.Biol.Chem.*, 262(2): 509-512 (1987).

Schmid, et al., "Immunochemical analysis of subunit structure of 1,4-dihydropyridine receptors associated with voltage-dependent $Ca^{2+}$ channels in skeletal, cardiac, and smooth muscles," *Biochemistry*, 25: 3492-3495 (1986).

Hubbard, et al., "Synthesis and processing of asparagine-linked oligosaccharides[1,2]," *Ann.Rev.Biochem.*, 50: 555-583 (1981).

Breitbart et al., "Alternatvie Splicing: A Ubiquitous Mechanism for the Generation of Multiple Protein Isoforms From Single Genes", *Ann. Rev. Biochem.*, 56:467-495 (1984).

Hamill, et al., "Improved patch-clamp techniques for high--resolution current recording from cells and cell-free membrane patches," *Pfluger Archiv.European Journal of Physiology*, 391: 85-100 (1981).

Hess, et al., "Different modes of Ca channel gating behavior favored by dihydropyridine Ca agonist and antagonists," *Nature*, 311: 538-544 (1984).

Leung, et al., "Biochemical and ultrastructural characterization of the 1,4-dihydropyridine receptor from rabbit skeletal muscle," *J. of Biol.Chem.*, 263(2): 994-1001 (1988).

Imagawa, et al., "Phosphorylation of the 1,4-dihydropyridine receptor of the voltage-dependent $Ca^{2+}$ channel by an intrinsic protein kinase in isolated triads from rabbit skeletal muscle," *J. of Biol.Chem.*, 262(17): 8333-8339 (1987).

Miller, "Multiple calcium channels and neuronal function," *Science*, 235: 46-52 (1987).

Sher, et al., "w-Conotoxin binding and effects on calcium channel function in human neuroblastoma and rat pheochromocytoma cell lines," *FEBS Letters*, 235: (1,2): 178-182 (1988).

Jay, et al., "Structural characterization of the dihydropyridine-sensitive calcium channel $\alpha_2$-subunit and the associated $\gamma$ peptides," *J.Biol.Chem.*, 266(5): 3287-3293 (1991).

Ellis et al. (1988) "Sequence and Expression of mRNAs Encoding the $\alpha_1$ and $\alpha_2$ Subunits of a DHP-Sensitive Calcium Channel", *Science* 241: 1661-1664.

Lotan, et al., "Specific block of calcium channel expression by a fragment of dihydropyridine receptor cDNA," *Science*, 243: 666-669 (1989).

Takahashi, et al., "Identification of an $\alpha$ subunit of dihydropyridine-sensitive brain calcium channels," *Science*, 236: 88-91 (1987).

Hofmann, et al., "Regulation of the L-type calcium channel," *TINS*, 8: 393-398 (1987).

Curtis, et al., "Reconstitution of the voltage-sensitive calcium channel purified from skeletal muscle transverse tubules," *Biochemistry*, 25: 3077-3083 (1986).

Smith, et al., "Calcium channel activity in a purified dihydropyridine-receptor preparation of skeletal muscle," *Biochemistry*, 26: 7182-7188 (1987).

Bean et al., "Classes of calcium channels in vertebrate cells," *Annu.Rev.Physiol.*, 51: 367-384 (1989).

Ruth, et al., "Primary structure of the $\alpha$ subunit of the DHP-sensitive calcium channel from skeletal muscle," *Science*, 245: 1115-1118 (1989).

Mikami, et al., "Primary structure and functional expression of the cardiac dihydropyridine-sensitive calcium channel," *Nature*, 340: 230-233 (1989).

Biel, et al., "Primary structure and functional expression of a high voltage activiated calcium channel from rabbit lung," *FEBS Letters*, 269(2): 409-412 (1990).

Snutch, et al., "Rat brain expresses a heterogeneous family of calcium channels," *Proc.Natl.Acad.Sci. USA*, 87: 3391-3395 (1990).

Burns, et al., "Calcium channel activity of purified human synexin and structure of the human synexin gene," *Proc. Natl.Acad.Sci.*, 86: 3798-3802 (1989).

Campbell, et al., "32,000-Dalton subunit of the 1,4-dihydropyridine receptor," *Ann.N.Y.Acad.Sci.*, 560: 251-257 (1989).

Dascal, N., "The use of *Xenopus oocytes* for the study of ion channels," *CRC Critical Rev.Biochem.*, 22(4): 317-387 (1987).

Jay, et al., "Primary Structure of the $\gamma$ subunit of the DHP-sensitive calcium channel from skeletal muscle," *Science*, 248: 490-492 (1990).

Cruz et al., "Characterization of $\omega$-Conotoxin Target. Evidence for Tissue-Specific Heterogeneity ion Calcium Channel Types", *Biochem. J.* 26:820 (1987).

Carbone, et al., "Ca currents in human neuroblastoma IMR32 cells: kinetics, permeability and pharmacology," *Pfluegers Arch.* 416: 170-179 (1990) (best available copy submitted).

Dascal, et al., "Expression of modulation of voltage-gated calcium channels after RNA injection in *Xenopus oocytes*," *Science*, 231: 1147-1150 (1986).

Hess, et al., "Calcium channels in vertebrate cells," *Ann.Rev.Neurosci.*, 13: 337-356 (1990).

Claudio, T., "Stable expression of transfected *Torpedo* acetylcholine receptor $\alpha$ subunits in mouse fibroblast L cells," *Proc.Natl.Acad.Sci.*, 84: 5967-5971 (1987).

Seagar, et al., "Molecular properties of dehydropyrine-sensitive calcium channels," *Ann.N.Y.Acad.Sci.*, 552: 162-175 (1988).

Takahashi and Catterall, "Dihydropyridine-sensitive calcium channels in cardiac and skeletal muscle membranes: studies with antibodies against the $\alpha$-subunits," *Biochemistry*, 26(17): 1518-1526 (1987).

Perez-Reyes, et al., "Induction of calcium currents by the expression of the $\alpha_1$-subunit of the dihydropyridine receptor from skeletal muscle," *Nature*, 340: 233-236 (1989).

Koch, et al., "Characterization of cDNA clones encoding two putative isoforms of the $\alpha_1$-subunit of the dihydropyridine-sensitive voltage-dependent calcium channel isolated from rat brain and rat aorta," *FEBS Letters*, 250(2): 386-388 (1989).

Slish, et al., "Evidence for the existence of a cardiac specific isoform of the $\alpha_1$-subunit of the voltage dependent calcium channel," *FEBS Letters*, 250(2): 509-514 (1989).

Varadi, et al., "Development regulation of expression of the $\alpha_1$ and $\alpha_2$ subunits mRNAs of the voltage-dependent calcium channel in a differentiating myogenic cell line," *FEBS Letters*, 250(2)CE: 515–518 (1989).

Jongh, et al., "Subunits of purified calcium channels: a 212-kDa form a $\alpha_1$ and partial amino acid sequences of a phosphorylation site of an independent β-subunit," *Proc. Natl.Acad.Sci. USA*, 86: 8585–8589 (1989).

Hamilton, et al., "Subunit composition of the purified dihydropyridine binding protein from skeletal muscle," *Biochemistry*, 28: 7820–7828 (1989).

Nunoki, et al., "Activation of purified calcium channels by stoichiometric protein phosphorylation," *Proc.Natl.Acad. Sci. USA*, 86: 6816–6820 (1989).

Ichida, et al., "Photoaffinity labeling with dihydropyridine derivatives of crude membranes from rat skeletal, cardiac, ileal, and uterine muscles and whole brain," *J.Biochem.*, 105: 767–774 (1989).

Sharp and Campbell, "Characterization of the 1,4–dihydropyridine receptor using subunit–specific polyclonal antibodies," *J.Biol.Chem.*, 264(5): 2816–2825 (1989).

Campbell, et al., "The biochemistry and molecular biology of the dihydropyridine–sensitive calcium channel," *TINS*, 11(10): 425–430 (1988).

Froehner, "New insights into the molecular structure of the dihydropyridine–sensitive calcium channel," *TINS*, 11(3): 90–92 (1988).

Catterall, et al., "Molecular properties of dihydropyridine–sensitive calcium channels in skeletal muscle," *J.Biol.Chem.*, 263(8): 3535–3538 (1988).

Brust et al., "Human Neuronal Voltage–Dependent Calcium Channels: Studies on Subunit Structure and Role in Channel Assembly", *Neuropharmacology* 32(11):1089–1102 (1993).

Williams, et al., "Structure and functional expression of $\alpha_1$, $\alpha_2$ and β subunits of a novel human neuronal calcium channel subtype," *Neuron*, 8:71–84 (1992).

Williams et al., "Structure and Functional Expression of an ω–Conotoxin–Sensitive Human N–Type Calcium Channel", *Science* 257:389–395 (1992).

Williams, et al., "Structure and Functional Characterization of Neuronal $\alpha_{1E}$ Calcium Channel Subtypes," *J. Biol. Chem.* 269(35):22347–22357 (1994).

FIG. 1(a)-1

```
GCGCCGCCGC CAGACCCTAC CTGGAGCACC CACCCCTCTG CAGCCGCC                              48

ATG TCC CCG ACG GAA GCC CCA AAG GTC CGC GTG ACC CTC TTC TGC ATC                   96
Met Ser Pro Thr Glu Ala Pro Lys Val Arg Val Thr Leu Phe Cys Ile
 1               5                  10                  15

CTG GTG GGC ATC GTG CTG GCC ATG ACG GCC GTG GTG AGC GAC CAC TGG                  144
Leu Val Gly Ile Val Leu Ala Met Thr Ala Val Val Ser Asp His Trp
                20                  25                  30

GCC GTG CTG AGC CCC CAC ATG GAG AAC CAC AAC ACC ACC TGC GAG GCC                  192
Ala Val Leu Ser Pro His Met Glu Asn His Asn Thr Thr Cys Glu Ala
        35                  40                  45

GCC CAC TTC GGC CTG TGG CGG ATT TGC ACC AAG CGC ATC GCC CTG GGC                  240
Ala His Phe Gly Leu Trp Arg Ile Cys Thr Lys Arg Ile Ala Leu Gly
    50                  55                  60

GAG GAC AGG AGC TGC GGA GGG CCC ATC ACC CTG CCT GGG GAG AAG AAC TGC              288
Glu Asp Arg Ser Cys Gly Gly Pro Ile Thr Leu Pro Gly Glu Lys Asn Cys
65                  70                  75                  80

TCC TAC TTC CGG CAT TTT AAC CCA GGC GAG AGC TCG GAG ATC TTC GAA                  336
Ser Tyr Phe Arg His Phe Asn Pro Gly Glu Ser Ser Glu Ile Phe Glu
                85                  90                  95
```

```
TTC ACC ACG CAG AAG GAG TAC AGC ATC TCG GCG GCC ATC AGC GTC        384
Phe Thr Thr Gln Lys Glu Tyr Ser Ile Ser Ala Ala Ile Ser Val
            100                 105                 110

TTC AGC CTG GGC TTC CTC ATG ATC ATG GGC ACC ATC TGC GCG CTC ATG GCC  432
Phe Ser Leu Gly Phe Leu Ile Met Gly Thr Ile Cys Ala Leu Met Ala
        115                 120                 125

TTC AGG AAG AAG CGG GAT TAC AGC TAC CTG CGG CCG GCG TCC ATG TTC TAC  480
Phe Arg Lys Lys Arg Asp Tyr Asp Tyr Leu Arg Pro Ala Ser Met Phe Tyr
    130                 135                 140

GTC TTT GCA GGC CTC TGC CTC TTT GTG TCA CTG GAG GTA ATG CGG CAG      528
Val Phe Ala Gly Leu Cys Leu Phe Val Ser Leu Glu Val Met Arg Gln
145                 150                 155                 160

TCG GTG AAA CGC ATG ATC GAC AGC GAG GAC ACC GTC TGG ATC GAG TAC      576
Ser Val Lys Arg Met Ile Asp Ser Glu Asp Thr Val Trp Ile Glu Tyr
        165                 170                 175

TAT TAC TCC TGG TCC TTT GCC TGC GCC TGC TGC GCC TTC GTC CTC CTC      624
Tyr Tyr Ser Trp Ser Phe Ala Cys Ala Cys Cys Ala Phe Val Leu Leu
    180                 185                 190
```

FIG. 1(a)-2

```
TTC CTC GGG GGT ATC TCC CTG CTG CTC TTC TCC CTG CCT CGA ATG CCC         672
Phe Leu Gly Gly Ile Ser Leu Leu Leu Phe Ser Leu Pro Arg Met Pro
            195                 200                 205

CAG AAC CCC TGG GAG TCC TGC ATG GAC GCC GAA CCC GAG CAT TAG             717
Gln Asn Pro Trp Glu Ser Cys Met Asp Ala Glu Pro Glu His End
        210                 215                 220

CCCTCCTGGG GCGCCCAGGG AGCCTCGGCC CAGAACCTTC CAGAAGGGAG GCAGGAATTG       777

CAAACCTGCC CTGTTCCCAT CTGCCTCACC CCGCGACTGC TTCCCTTCCG TGGCTCTGAC       837

GGAGCTCCTC TGCTCACAGG GCAAATGGAC GCGAGCCCAG CCCTGTCCTG GTTGGACGAG       897

GTGGGCAGGT GGTTGGAGGG GCCCGGGCCT CCACTGAGGC TCAAAGCCGT CCCTGCTGTG       957

CCGGTTCTCC TTGGGAAGCT GGGCCTGGT AAACCTGGTA AACCTCCCAG GAGCACCCCG        1017

TGCGCGCATG CCGGTGCTGG GTGCCCCCTG TGTGAAAAGC CGGCCCCTCT GTCTTCCCAG       1077

CCACCAGAAC CTTCGTTGCC TCCCGGAGCT CTGGGAATCA GCATTTTCCA CCAGGGAGTA      1137

TCTGACTGTG GTTTGAAATA AAAGGCTCA GAAC                                    1171
```

FIG. 1(b)

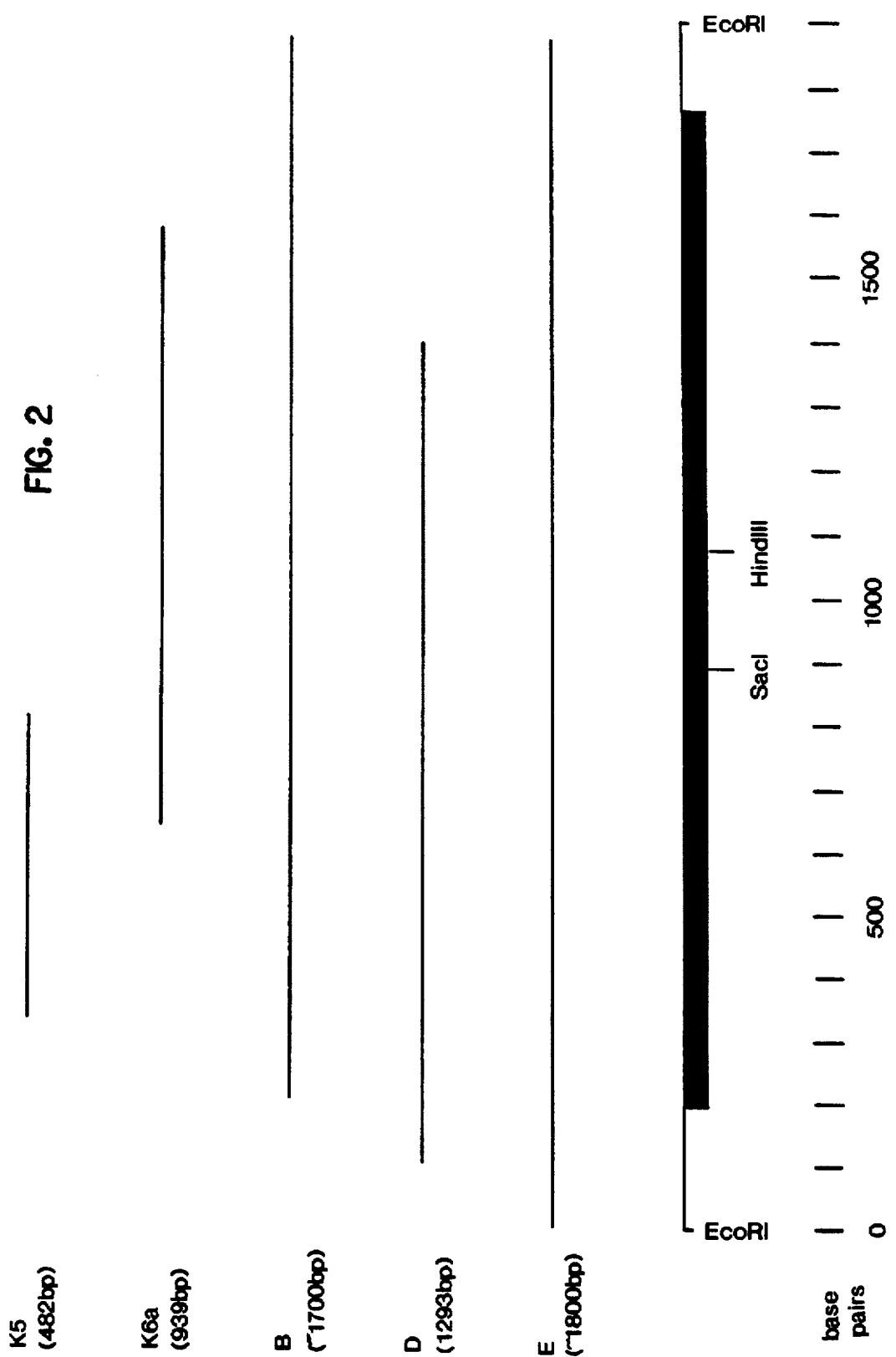

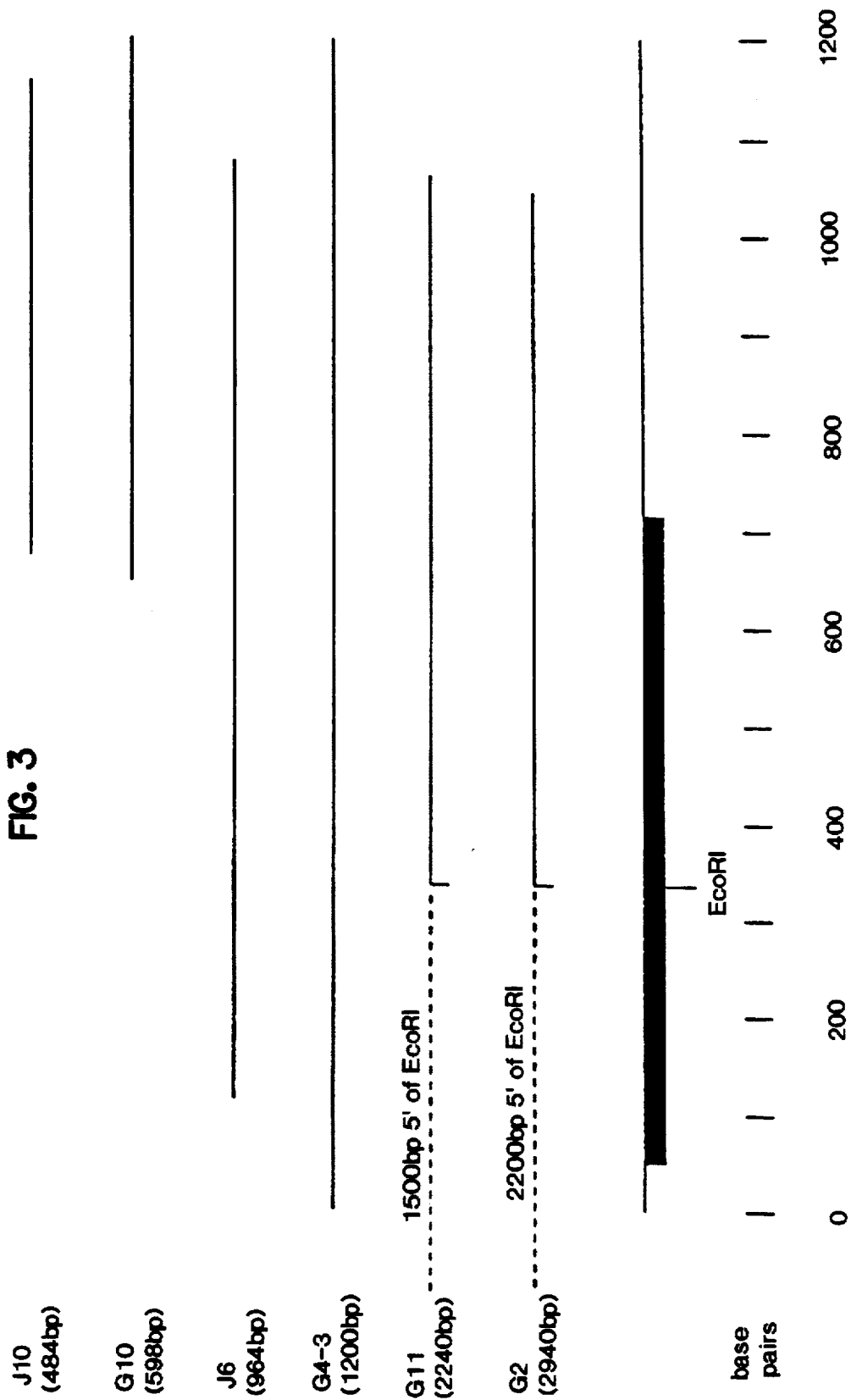

FIG. 4(a)-1

```
GGCTGCGCTG CGCCGCCCTC GGCTCCGACG GGCTTCTCCC ATGCGCTGAG GGGCCGGGCG      60

GGGCGTGGCG GCCGGAGGAG AGGCTCCCCT CC                                     92

ATG GTC CAG AAG ACC AGC ATG TCC CGG GGT CCT TAC CCA CCC TCC CAG        140
Met Val Gln Lys Thr Ser Met Ser Arg Gly Pro Tyr Pro Pro Ser Gln
 1               5                  10                  15

GAG ATC CCC ATG GAG GTC TTC GAC CCC AGC CCG CAG GGC AAA TAC AGC        188
Glu Ile Pro Met Glu Val Phe Asp Pro Ser Pro Gln Gly Lys Tyr Ser
             20                  25                  30

AAG AGA AAA GGG CGC TTC AAA CGG AAG CGG AGC ACC TCC TCA GAT            236
Lys Arg Lys Gly Arg Phe Lys Arg Lys Arg Ser Thr Ser Ser Asp
         35                  40                  45

ACA ACA TCC AAC AGC TTT GTG CGC CAG GGC TCT GCC GAG TCC TAC ACC        284
Thr Thr Ser Asn Ser Phe Val Arg Gln Gly Ser Ala Glu Ser Tyr Thr
     50                  55                  60

AGC CGT CCG TCG GAC TCT GAT GTC TCC CTG GAG GAG GAC CGG GAA GCC        332
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCC CAG CTT GAG AAA GCC        380
Leu Arg Lys Glu Ala Glu Arg Gln Ala Leu Ala Gln Leu Glu Lys Ala
             85                  90                  95
```

```
AAG ACC AAG CCA GTA GCA TTT GCC GTG CGG ACA AAT GTC GGC TAC AAT    428
Lys Thr Lys Pro Val Ala Phe Ala Val Arg Thr Asn Val Gly Tyr Asn
              100                      105                 110

CCA TCT CCA GGG GAT GAG GTG CCT GTG GAG GGA GTG GCC ATC ACC TTT    476
Pro Ser Pro Gly Asp Glu Val Pro Val Glu Gly Val Ala Ile Thr Phe
              115                      120                 125

GAG CCC AAG GAC TTC CTG CAC ATC AAG GAG AAA TAC AAC AAT GAC TGG    524
Glu Pro Lys Asp Phe Leu His Ile Lys Glu Lys Tyr Asn Asn Asp Trp
              130                      135                 140

TGG ATT GGG CGG CTG GTG AAG GAG GGC TGC GAG GTT GGC TTC ATC CCC    572
Trp Ile Gly Arg Leu Val Lys Glu Gly Cys Glu Val Gly Phe Ile Pro
              145                      150                 155                 160

AGC CCC GTC AAA CTG GAC AGC CTG CGC CTG CAG GAA CAG AAG CTG         620
Ser Pro Val Lys Leu Asp Ser Leu Arg Leu Gln Glu Gln Lys Leu
              165                      170                 175

CGT CAG AGC CGC CTC AGC TCC AGC AAA TCA GGC GAC AAC TCC AGC TCC    668
Arg Gln Ser Arg Leu Ser Ser Ser Lys Ser Gly Asp Asn Ser Ser Ser
              180                      185                 190
```

```
AGT CTG GGT GAC GTA GTG ACT GGC ACG CGC CGC CCC ACA CCC CCT GCC    716
Ser Leu Gly Asp Val Val Thr Gly Thr Arg Arg Pro Thr Pro Pro Ala
            195                 200                 205

AGT GGT AAC GAG ATG ACT AAC TTA GCC TTT GAA CTA GAG CCC TTA GAC    764
Ser Gly Asn Glu Met Thr Asn Leu Ala Phe Glu Leu Glu Pro Leu Asp
            210                 215                 220

TTA GAG GAC GCA GAG CTC GGT GAG CAG CAG AGC GGC TCT GCC AAG        812
Leu Glu Asp Ala Glu Leu Gly Glu Gln Gln Ser Gly Ser Ala Lys
            225                 230                 235         240

ACT AGC GTT AGC AGT GTC ACC ACC CCG CCA CCC CAC GGC ACA CGC ATC    860
Thr Ser Val Ser Ser Val Thr Thr Pro Pro Pro His Gly Thr Arg Ile
            245                 250                 255

CCC TTC TTT AAG ACA AAG GAG CAC GTG CTG GTG CCC TAT GAC GTG CCT    908
Pro Phe Phe Lys Thr Lys Glu His Val Leu Val Pro Tyr Asp Val Pro
            260                 265                 270

TCC ATG AGG CCC ATC ATC CTG GGA CCG TCG CTC AAG GGC TAT GAG        956
Ser Met Arg Pro Ile Ile Leu Val Gly Pro Ser Leu Lys Gly Tyr Glu
            275                 280                 285

GTG ACA GAC ATG ATG CAG AAA GCT TTG TTT GAC TTC CTG AAG CAT CGG   1004
Val Thr Asp Met Met Gln Lys Ala Leu Phe Asp Phe Leu Lys His Arg
            290                 295                 300
```

```
TTT GAT GGC AGG ATC TCC ATC ACG CGG GTG ACA GCC GAC ATC TCC CTG   1052
Phe Asp Gly Arg Ile Ser Ile Thr Arg Val Thr Ala Asp Ile Ser Leu
305                 310                 315                 320

GCT AAG CGC TCA GTC CTC AAC AAC CCC AGC AAG CAC ATC ATC ATC GAG   1100
Ala Lys Arg Ser Val Leu Asn Asn Pro Ser Lys His Ile Ile Ile Glu
            325                 330                 335

CGC TCC AAC ACA CGC TCC AGC CTG GCT GAG GTG CAG AGT GAG ATT GAA   1148
Arg Ser Asn Thr Arg Ser Ser Leu Ala Glu Val Gln Ser Glu Ile Glu
        340                 345                 350

CGA ATC TTC GAG CTG GCC CGG ACC CTC CAG CTC GTC GCT CTG GAC GCG   1196
Arg Ile Phe Glu Leu Ala Arg Thr Leu Gln Leu Val Ala Leu Asp Ala
    355                 360                 365

GAC ACC ATC AAC CAC CCT GCC CTC TCC AAG ACC TCA CTG GCG CCC       1244
Asp Thr Ile Asn His Pro Ala Leu Ser Lys Thr Ser Leu Ala Pro
370                 375                 380

ATC ATT GTT TAC ATC AAG ATC ACC TCC CCC AAG GTA CTT CAG AGG CTC   1292
Ile Ile Val Tyr Ile Lys Ile Thr Ser Pro Lys Val Leu Gln Arg Leu
385                 390                 395                 400                 500
```

FIG. 4(b)-2

| | | | | | | | | |
|---|---|---|---|---|---|---|---|---|
| ATC | AAG | TCC | CGG | GGG | AAG | TCT | CAG | TCC | AAA | CAC | CTC | AAC | GTC | CAG | ATA | 1340 |
| Ile | Lys | Ser | Arg | Gly | Lys | Ser | Gln | Ser | Lys | His | Leu | Asn | Val | Gln | Ile |
| | | 505 | | | | | | 510 | | | | | | | 515 | |

GCA GCC TCG GAG AAG CTG GCG CAG TGT CCG CCC GAA ATG TTT GAC ATC 1388
Ala Ala Ser Glu Lys Leu Ala Gln Cys Pro Pro Glu Met Phe Asp Ile
520                              525                              530

ATC CTG GAC GAG AAC CAA TTG GAG GAT GCC TGC GAG CAC CTG GCC GAG 1436
Ile Leu Asp Glu Asn Gln Leu Glu Asp Ala Cys Glu His Leu Ala Glu
535                              540                              545

TAC TTG GAA GCC TAC TGG AAG GCC ACA CAC CCG AGC AGC ACA CCG 1484
Tyr Leu Glu Ala Tyr Trp Lys Ala Thr His Pro Ser Ser Thr Pro
550                              555                              560

CCC AAT CCG CTG CTG AAC CGC ACC ATG GCC ACC GCA GTG CAG GCC GCC 1532
Pro Asn Pro Leu Leu Asn Arg Thr Met Ala Thr Ala Val Gln Ala Ala
565                              570                              575                              580

AGC CCT GCC CCT GTC TCC AAC CTC CAG GTA CAG GTG CTC ACC TCG CTC 1580
Ser Pro Ala Pro Val Ser Asn Leu Gln Val Gln Val Leu Thr Ser Leu
585                              590                              595

AGG AGA AAC CTC AGC TTC TGG GGC GGG CTG GAG ACC TCC CAG CGG GGC 1628
Arg Arg Asn Leu Ser Phe Trp Gly Gly Leu Glu Thr Ser Gln Arg Gly
600                              605                              610

GGC GGT GCG GTG CCC CAA CAG CAG GAG CAC GCC ATG TAG 1667
Gly Gly Ala Val Pro Gln Gln Gln Glu His Ala Met End

CGGGGACCG CCCGTCTTCC CTCCGCCCAG GGCGTGGAAC TGGAGTGCAG GGAACATGGG 1727

CAAGGAAGGG AAGAGCTTTA TTTTGTAAAA AACGTGGTGA GCGGC 1772

FIG. 4 (c)

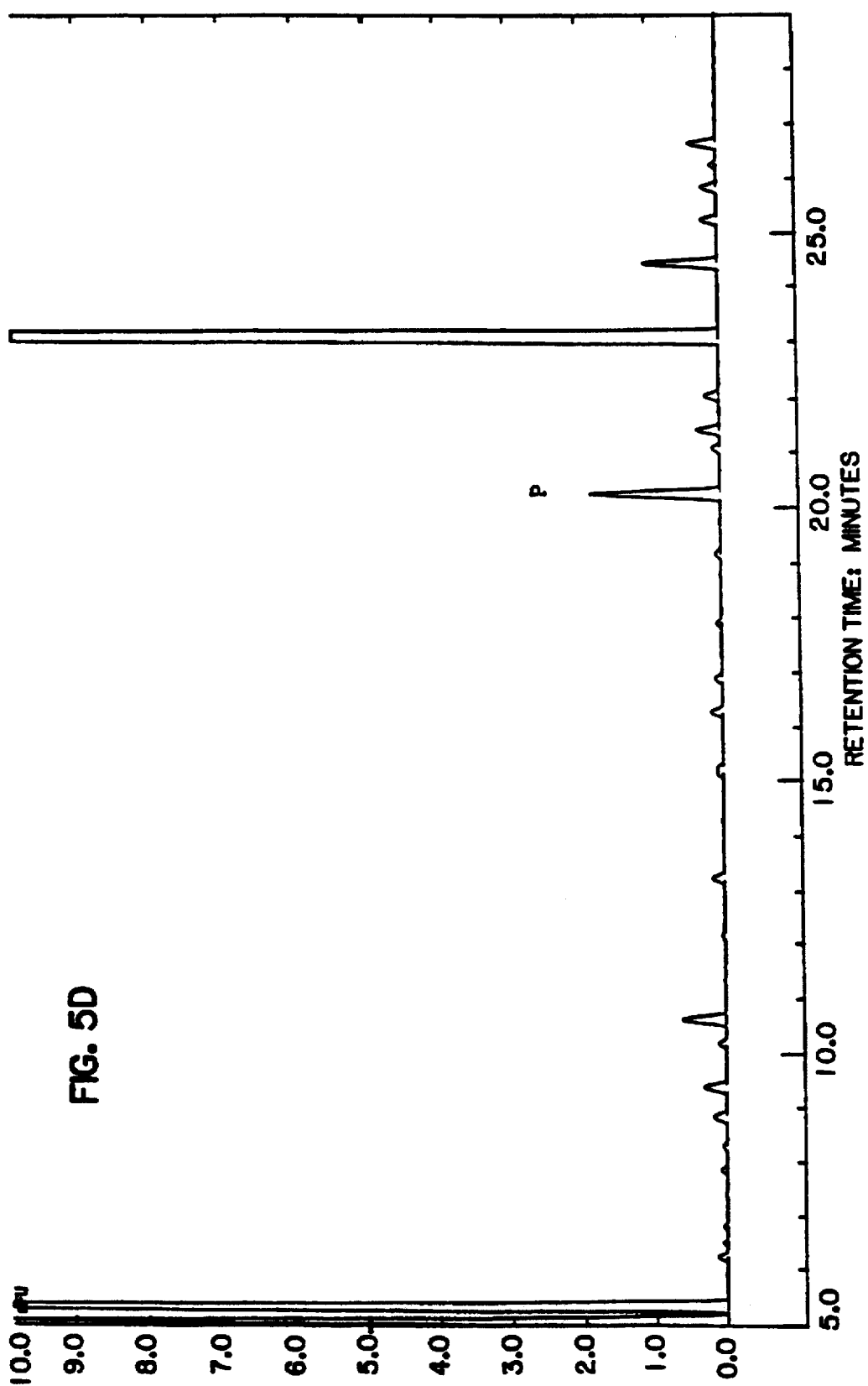

FIG. 8(a)-1

```
GCGGGGAACA CTGGGGACGC AGGGAAGAGA GGGCCCGCGGG GTGGGGGAGC AGCAGGAAGC      60

GCCGTGGCCA GGGAAGCC                                                    78

ATG GAG CCA TCC TCA CCC CAG GAT GAG GGC CTG AGG AAG AAA CAG CCC       126
Met Glu Pro Ser Ser Pro Gln Asp Glu Gly Leu Arg Lys Lys Gln Pro
 1               5                  10                  15

AAG AAG CCC CTG CCC GAG GTC CTG CCC AGG CCG CGG GCT CTG TTC           174
Lys Lys Pro Leu Pro Glu Val Leu Pro Arg Pro Arg Ala Leu Phe
             20                  25                  30

TGC CTG ACC CTG CAG AAC CCG CTG AGG AAG GCG TGC ATC AGC ATC GTG       222
Cys Leu Thr Leu Gln Asn Pro Leu Arg Lys Ala Cys Ile Ser Ile Val
         35                  40                  45

GAA TGG AAA CCC TTC GAG ACC CTG ATC ATC CTC ACC ATC TTT GCC AAC       270
Glu Trp Lys Pro Phe Glu Thr Leu Ile Ile Leu Thr Ile Phe Ala Asn
     50                  55                  60

TGT GTG GCC CTG GCC GTG TAC CTG TAC CTG GCC GTG CCC ATG CCC GAG GAT GAC AAC AAC       318
Cys Val Ala Leu Ala Val Tyr Leu Tyr Leu Pro Met Pro Glu Asp Asp Asn Asn
 65                  70                  75                  80

TCC CTG AAC CTG GGC CTG GAG AAG CTG GAG TAC TTC TTC CTC ACC GTC       366
Ser Leu Asn Leu Gly Leu Glu Lys Leu Glu Tyr Phe Phe Leu Thr Val
         85                  90                  95
```

```
TTC TCC ATC GAA GCC GCC ATG AAG ATC ATC GCC TAC GGC TTC CTG TTC    414
Phe Ser Ile Glu Ala Ala Met Lys Ile Ile Ala Tyr Gly Phe Leu Phe
100                         105                         110

CAC CAG GAC GCC TAC CTG CGC AGC CGC AGC TGG AAC GTG CTG GAC TTC ATC    462
His Gln Asp Ala Tyr Leu Arg Ser Arg Ser Gly Trp Asn Val Leu Asp Phe Ile
         115                         120                         125

ATC GTC TTC CTG GGG GTC TTC ACG GCG ATT CTG GAA CAG GTC AAC GTC    510
Ile Val Phe Leu Gly Val Phe Thr Ala Ile Leu Glu Gln Val Asn Val
130                         135                         140

ATC CAG AGC AAC ACG GCC CCG ATG AGC AGC AAA GGA GCC GGC CTG GAC    558
Ile Gln Ser Asn Thr Ala Pro Met Ser Ser Lys Gly Ala Gly Leu Asp
145                         150                         155                    160

GTC AAG GCC CTG AGG GCC TTC CGT GTG CTC AGA CCC CTC CGG CTG GTG    606
Val Lys Ala Leu Arg Ala Phe Arg Val Leu Arg Pro Leu Arg Leu Val
                    165                         170                         175

TCG GGG GTG CCT AGT TTG CAG GTG GTC CTC AAC TCC ATC TTC AAG GCC    654
Ser Gly Val Pro Ser Leu Gln Val Val Leu Asn Ser Ile Phe Lys Ala
180                         185                         190
```

```
ATG CTC CCC CTG TTC CAC ATC GCC CTG CTC GTC CTC TTC ATG GTC ATC    702
Met Leu Pro Leu Phe His Ile Ala Leu Leu Val Leu Phe Met Val Ile
        195                     200                     205

ATC TAC GCC ATC ATC GGG CTG GAG CTC TTC AAG GGC AAG ATG CAC AAG    750
Ile Tyr Ala Ile Ile Gly Leu Glu Leu Phe Lys Gly Lys Met His Lys
    210                     215                     220

ACC TGC TAC TAC ATC GGG ACA GAC ATC GTG GCC ACA GTG GAG AAT GAG    798
Thr Cys Tyr Tyr Ile Gly Thr Asp Ile Val Ala Thr Val Glu Asn Glu
225                     230                     235             240

AAG CCC TCG CCC TGC GCT AGG ACG GGC TCG CCC TGC ACC GGC ATC        846
Lys Pro Ser Pro Cys Ala Arg Thr Gly Ser Gly Arg Pro Cys Thr Ile
            245                     250                     255

AAC GGC AGC GAG TGC CGG GGC TGG GGC CCG AAC CAC GGC ATC            894
Asn Gly Ser Glu Cys Arg Gly Trp Gly Pro Asn His Gly Ile
        260                     265                     270

ACG CAC TTC GAC AAC TTC GGC ATG TCC ATG TCC ATG CTC ACC GTG TAC CAG TGC    942
Thr His Phe Asp Asn Phe Gly Met Ser Met Leu Thr Val Tyr Gln Cys
    275                     280                     285

ATC ACC ATG GAG GGC TGG ACA GAT GTC CTC TAC GTC AAC GAT GCC        990
Ile Thr Met Glu Gly Trp Thr Asp Val Leu Tyr Val Asn Asp Ala
290                     295                     300
```

```
ATC GGG AAC GAG TGG CCC TGG ATC TAC TTT GTC ACT CTC ATC CTG CTG    1038
Ile Gly Asn Glu Trp Pro Trp Ile Tyr Phe Val Thr Leu Ile Leu Leu
305                     310                     315          320

GGG TCC TTC TTC ATC CTC AAC CTG GTG CTG GGC GTC CTG AGT GGG GAA    1086
Gly Ser Phe Phe Ile Leu Asn Leu Val Leu Gly Val Leu Ser Gly Glu
            325                     330                     335

TTC ACC AAG GAG CGG GAG AAG GCC AAG TCC AGG GGA ACC TTC CAG AAG    1134
Phe Thr Lys Glu Arg Glu Lys Ala Lys Ser Arg Gly Thr Phe Gln Lys
        340                     345                     350

CTG CGG GAG AAG CAG CAG CTG GAG GAG GAC CTT CGG GGC TAC ATG AGC    1182
Leu Arg Glu Lys Gln Gln Leu Glu Glu Asp Leu Arg Gly Tyr Met Ser
355                     360                     365

TGG ATC ACG CAG GGC GAG ATG GAC GTG GAG GAC GTG AGA GAA GGA        1230
Trp Ile Thr Gln Gly Glu Met Asp Val Glu Asp Val Arg Glu Gly
        370                     375                     380

AAG CTG TCC TTG GAA GAG GGA GGC TCC GAC ACG GAA AGC CTG TAC GAA    1278
Lys Leu Ser Leu Glu Glu Gly Gly Ser Asp Thr Glu Ser Leu Tyr Glu
385                     390                     395          400
```

```
ATC GAG GGC TTG AAC AAA ATC ATC CAG TTC ATC CGA CAC TGG AGG CAG      1326
Ile Glu Gly Leu Asn Lys Ile Ile Gln Phe Ile Arg His Trp Arg Gln
                    405                 410                 415

TGG AAC CGT GTC TTT CGC TGG AAG TGC CAT GAC CTG GTG AAG TCG AGA      1374
Trp Asn Arg Val Phe Arg Trp Lys Cys His Asp Leu Val Lys Ser Arg
            420                 425                 430

GTC TTC TAC TGG CTG GTC ATC GTC CTG GCC CTC AAC ACC CTG TCC          1422
Val Phe Tyr Trp Leu Val Ile Val Leu Ala Leu Asn Thr Leu Ser
        435                 440                 445

ATC GCC TCG GAG CAC CAC AAC CAG CCG CTC TGG CTG ACC CAC TTG CAA      1470
Ile Ala Ser Glu His His Asn Gln Pro Leu Trp Leu Thr His Leu Gln
        450                 455                 460

GAC ATC GCC AAT CGA GTG CTG CTG TCA CTC TTC ACC ATC GAG ATG CTG      1518
Asp Ile Ala Asn Arg Val Leu Leu Ser Leu Phe Thr Ile Glu Met Leu
    465                 470                 475                 480

CTG AAG ATG TAC GGG CTG GGC CTG CGC CAG TAC TTC ATG TCC ATC TTC      1566
Leu Lys Met Tyr Gly Leu Gly Leu Arg Gln Tyr Phe Met Ser Ile Phe
            485                 490                 495

AAC CGC TTC GAC TGC TTC GTG GTG TGC AGC GGC ATC CTG GAG CTG CTG      1614
Asn Arg Phe Asp Cys Phe Val Val Cys Ser Gly Ile Leu Glu Leu Leu
        500                 505                 510
```

```
CTG GTG GAG TCG GGC GCC ATG ACG CCG CTG GGC ATC TCC GTG TTG CGC    1662
Leu Val Glu Ser Gly Ala Met Thr Pro Leu Gly Ile Ser Val Leu Arg
     515                 520                 525

TGC ATC CGC CTC CTG AGG CTC TTC AAG ATC ACC AAG TAC TGG ACG TCG    1710
Cys Ile Arg Leu Leu Arg Leu Phe Lys Ile Thr Lys Tyr Trp Thr Ser
             530                 535                 540

CTC AGC AAC CTG GTG GCC TCC CTG CTG CTC AAC TCC ATC CGC ATC GCC    1758
Leu Ser Asn Leu Val Ala Ser Leu Leu Leu Asn Ser Ile Arg Ile Ala
 545                 550                 555                 560

TCG CTG CTG CTG CTC TTC CTC CTG CTC TTC ATC ATC ATC TTC GCC CTG CTG   1806
Ser Leu Leu Leu Leu Phe Leu Leu Leu Phe Ile Ile Ile Phe Ala Leu Leu
             565                 570                 575

GGC ATG CAG CTC TTC GGG CGG TAC GAC TTC GAG GAC ACG GAA GTG          1854
Gly Met Gln Leu Phe Gly Gly Arg Tyr Asp Phe Glu Asp Thr Glu Val
 580                 585                 590

CGA CGC AGC AAC TTC GAC AAC TTC CCC CAG GCC CTC ATC AGC GTC TTC    1902
Arg Arg Ser Asn Phe Asp Asn Phe Pro Gln Ala Leu Ile Ser Val Phe
             595                 600                 605
```

```
CAG GTG CTG ACG GGT GAG GAC TGG AAC TCC GTG ATG TAC AAC GGG ATC          1950
Gln Val Leu Thr Gly Glu Asp Trp Asn Ser Val Met Tyr Asn Gly Ile
610                          615                      620

ATG GCC TAC GGA GGC CCG TCC TAC CCG GGC GTT CTC GTG TGC ATC TAT          1998
Met Ala Tyr Gly Gly Pro Ser Tyr Pro Gly Val Leu Val Cys Ile Tyr
625                      630                      635              640

TTC ATC ATC CTT TTT GTC TGC GGC AAC TAT ATC CTG AAT GTC TTC              2046
Phe Ile Ile Leu Phe Val Cys Gly Asn Tyr Ile Leu Asn Val Phe
645                      650                      655

CTG GCC ATC GCC GTG GAC AAC CTG GCC GAG GCC GAG AGC CTG ACT TCC          2094
Leu Ala Ile Ala Val Asp Asn Leu Ala Glu Ala Glu Ser Leu Thr Ser
660                      665                      670

GCC CAA AAG GCC AAG GCC AAG GAG GAG AGG AAA CGT AGG AAG ATG TCC AGG      2142
Ala Gln Lys Ala Lys Ala Lys Glu Glu Arg Lys Arg Arg Lys Met Ser Arg
675                      680                      685

GGT CTC CCT GAC AAG ACG GAG GAG AAG TCT GTG ATG GCC AAG AAG              2190
Gly Leu Pro Asp Lys Thr Glu Glu Lys Ser Val Met Ala Lys Lys
690                      695                      700

CTG GAG CAG AAG CCC AAG GGG GAG GGC ATC CCC ACC ACT GCC AAG CTC          2238
Leu Glu Gln Lys Pro Lys Gly Glu Gly Ile Pro Thr Thr Ala Lys Leu
705                      710                      715              720
```

```
AAG GTC GAT GAG TTC GAA TCT AAC GTC AAC GAG GTG AAG GAC CCC TAC    2286
Lys Val Asp Glu Phe Glu Ser Asn Val Asn Glu Val Lys Asp Pro Tyr
                725             730             735

CCT TCA GCT GAC TTC CCA GGG GAT GAT GAG GAG CCT GAG ATC            2334
Pro Ser Ala Asp Phe Pro Gly Asp Asp Glu Glu Pro Glu Ile
            740             745             750

CCA GTG AGC CCC CGA CCG CGC CCG CTG GCC CTG CAG CTC AAA GAG        2382
Pro Val Ser Pro Arg Pro Arg Pro Leu Ala Leu Gln Leu Lys Glu
        755             760             765

AAG GCA GTG CCC ATC CCG GAA GCC AGC TCC TTC ATC TTC AGT CCC        2430
Lys Ala Val Pro Ile Pro Glu Ala Ser Ser Phe Ile Phe Ser Pro
770             775             780

ACC AAT AAG GTC CGT GTC CTG TGT CAC CGC ATC GTC AAC GCC ACC TGG    2478
Thr Asn Lys Val Arg Val Leu Cys His Arg Ile Val Asn Ala Thr Trp
785             790             795             •           800

TTC ACC AAC TTC ATC CTG CTC ATC CTG TTC AGC AGT GCT GCG CTG        2526
Phe Thr Asn Phe Ile Leu Leu Ile Leu Phe Ser Ser Ala Ala Leu
    805             810             815
```

```
GCC GCC GAG GAC CCC ATC CGG GCG GAG TCC GTG AGG AAT CAG ATC CTT    2574
Ala Ala Glu Asp Pro Ile Arg Ala Glu Ser Val Arg Asn Gln Ile Leu
         820                     825                     830

GGA TAT TTT GAT ATT GCC TTC ACC TCT GTC TCT GTC GAG ATT GTC        2622
Gly Tyr Phe Asp Ile Ala Phe Thr Ser Val Phe Thr Val Glu Ile Val
         835                     840                     845

CTC AAG ACA ACC TAC GGC GCC TTC CTG CAC AAG GGC TCC TTC TGC        2670
Leu Lys Met Thr Thr Tyr Gly Ala Phe Leu His Lys Gly Ser Phe Cys
         850                     855                     860

CGC AAC TAC TTC AAC ATC CTG GAC CTG CTG GTG GCC GTG TCT CTC        2718
Arg Asn Tyr Phe Asn Ile Leu Asp Leu Leu Val Ala Val Ser Leu
         865                     870                     875        880

ATC TCC ATG GGT CTC GAG TCC AGC ACC ATC TCC GTG GTA AAG ATC CTG    2766
Ile Ser Met Gly Leu Glu Ser Ser Thr Ile Ser Val Val Lys Ile Leu
         885                     890                     895

AGA GTG CTA AGG GTG CTC CGG CCC CTG CGA GCC ATC AAC AGA GCC AAA    2814
Arg Val Leu Arg Val Leu Arg Pro Leu Arg Ala Ile Asn Arg Ala Lys
         900                     905                     910

GGG TTG AAG CAC GTG GTG CAG TGC GTG TTC GTG GCC ATC CGC ACC ATC    2862
Gly Leu Lys His Val Val Gln Cys Val Phe Val Ala Ile Arg Thr Ile
         915                     920                     925
```

```
GGG AAC ATC GTC CTG GTC ACC ACG CTC CAG TTC ATG TTC GCC TGC   2910
Gly Asn Ile Val Leu Val Thr Thr Leu Gln Phe Met Phe Ala Cys
930                     935                     940

ATC GGT GTC CAG CTC TTC AAG GGC AAG TTC TTC AGC TGC AAT GAC CTA   2958
Ile Gly Val Gln Leu Phe Lys Gly Lys Phe Phe Ser Cys Asn Asp Leu
945                     950                     955            960

TCC AAG ATG ACA GAA GAG TGC AGG GGC TAC TAC TAT GTG TAC AAG       3006
Ser Lys Met Thr Glu Glu Cys Arg Gly Tyr Tyr Tyr Val Tyr Lys
                965                     970                 975

GAC GGG GAC CCC ACG CAG ATG GAG CTG CGC CCC CGC CAG TGG ATA CAC   3054
Asp Gly Asp Pro Thr Gln Met Glu Leu Arg Pro Arg Gln Trp Ile His
        980                     985                     990

AAT GAC TTC CAC TTT GAC AAC GTG TCG GCC ATG ATG TCG CTC TTC       3102
Asn Asp Phe His Phe Asp Asn Val Ser Ala Met Met Ser Leu Phe
    995                    1000                    1005

ACG GTG TCC ACC TTC GAG GGA TGG CCC CAG CTG CTG TAC AGG GCC ATA   3150
Thr Val Ser Thr Phe Glu Gly Trp Pro Gln Leu Leu Tyr Arg Ala Ile
1010                   1015                    1020
```

| | | |
|---|---|---|
| GAC TCC AAC GAG GAG GAC ATG GGC CCC GTT TAC AAC AAC CGA GTG GAG<br>Asp Ser Asn Glu Glu Asp Met Gly Pro Val Tyr Asn Asn Arg Val Glu<br>1025                                            1030                                      1035                                    1040 | 3198 |
| ATG GCC ATC TTC ATC ATC TAC ATC ATC CTC ATT GCC TTC TTC ATG<br>Met Ala Ile Phe Ile Ile Tyr Ile Ile Leu Ile Ala Phe Phe Met<br>                   1045                                      1050                                    1055 | 3246 |
| ATG AAC ATC TTT GTG GGC TTT GTC ATC GTC ACC TTC CAG GAG CAG GGG<br>Met Asn Ile Phe Val Gly Phe Val Ile Val Thr Phe Gln Glu Gln Gly<br>1060                                      1065                                  1070 | 3294 |
| GAG ACG GAG TAC AAG AAC TGC GAG CTG GAC AAG AAC CAG CGC CAG TGT<br>Glu Thr Glu Tyr Lys Asn Cys Glu Leu Asp Lys Asn Gln Arg Gln Cys<br>     1075                                    1080                                    1085 | 3342 |
| GTG CAG TAT GCC CTG AAG GCC CGC CCA CTT CGG TGC TAC ATC CCC AAG<br>Val Gln Tyr Ala Leu Lys Ala Arg Pro Leu Arg Cys Tyr Ile Pro Lys<br>1090                                      1095                                  1100 | 3390 |
| AAC CCA TAC CAG TAC CAG TAC GTC GTC ACC TCC TCC TAC TTT<br>Asn Pro Tyr Gln Tyr Gln Val Trp Tyr Val Val Thr Ser Ser Tyr Phe<br>1105                                      1110                                  1115                                  1120 | 3438 |
| GAA TAC CTG ATG TTC GCC CTC ATG CTC ATC ATG CTC ATC ATC TGC CTG GGC<br>Glu Tyr Leu Met Phe Ala Leu Met Leu Ile Met Leu Asn Thr Ile Cys Leu Gly<br>                   1125                                      1130                                    1135 | 3486 |

```
ATG CAG CAC TAC CAC CAG TCG GAG GAG ATG AAC CAC ATC TCA GAC ATC    3534
Met Gln His Tyr His Gln Ser Glu Glu Met Asn His Ile Ser Asp Ile
1140                    1145                    1150

CTC AAT GTG GCC TTC ACC ATC ATC TTC ACG CTG GAG ATG ATT CTC AAG    3582
Leu Asn Val Ala Phe Thr Ile Ile Phe Thr Leu Glu Met Ile Leu Lys
    1155                    1160                    1165

CTC TTG GCG TTC AAG GCC AGG GGC TAT TTC GGA GAC CCC TGG AAT GTG    3630
Leu Leu Ala Phe Lys Ala Arg Gly Tyr Phe Gly Asp Pro Trp Asn Val
1170                    1175                    1180

TTC GAC TTC CTG ATC GTC ATC GGC AGC ATC ATT GAC GTC ATC CTC AGC    3678
Phe Asp Phe Leu Ile Val Ile Gly Ser Ile Ile Asp Val Ile Leu Ser
1185                    1190                    1195            1200

GAG ATC GAC ACT TTC CTG GCC TCC AGC GGG GGA CTG TAT TGC CTG GGT    3726
Glu Ile Asp Thr Phe Leu Ala Ser Ser Gly Gly Leu Tyr Cys Leu Gly
        1205                    1210                    1215

GGC TGC GGG AAC GTT GAC CCA GAC GAG AGC GCC CGC ATC TCC AGT        3774
Gly Gly Cys Gly Asn Val Asp Pro Asp Glu Ser Ala Arg Ile Ser Ser
        1220                    1225                    1230
```

```
GCC TTC TTC CGC CTG TTC CGG GTT ATG AGG CTG ATC AAG CTG AGT      3822
Ala Phe Phe Arg Leu Phe Arg Val Met Arg Leu Ile Lys Leu Leu Ser
           1235                     1240                 1245

CGG GCC GAG GGC GTG CGC ACG CTG CTG TGG ACG TTC ATC AAG TCC TTC  3870
Arg Ala Glu Gly Val Arg Thr Leu Leu Trp Thr Phe Ile Lys Ser Phe
           1250                     1255                 1260

CAG GCC CTG CCC TAC GTG GCC CTC ATC GTC CTG ATG CTG TTC TTC ATC  3918
Gln Ala Leu Pro Tyr Val Ala Leu Ile Val Leu Met Leu Phe Phe Ile
           1265                     1270                 1275     1280

TAC GCC GTC ATC GGC ATG TTT GGA AAG ATC GCC CTG GTG GAC          3966
Tyr Ala Val Ile Gly Met Phe Gly Lys Ile Ala Leu Val Asp
           1285                     1290                 1295

GGG ACC CAG ATC AAC AAC CGC AAC AAC TTC CAG ACC TTC CCG CAG GCC  4014
Gly Thr Gln Ile Asn Asn Arg Asn Asn Phe Gln Thr Phe Pro Gln Ala
           1300                     1305                 1310

GTG CTG CTC TTC AGG TGT GCG ACA GGG GAG GCG TGG CAA GAG ATC      4062
Val Leu Leu Phe Arg Cys Ala Thr Gly Glu Ala Trp Gln Glu Ile
           1315                     1320                 1325

CTG CTG GCC TGC AGC TAC GGG AAG TTG TGC GAC CCA GAG TCA GAC TAC  4110
Leu Leu Ala Cys Ser Tyr Gly Lys Leu Cys Asp Pro Glu Ser Asp Tyr
           1330                     1335                 1340
```

```
GCC CCG GGC GAG GAG TAC ACG TGT GGC ACC AAC TTC GCC TAC TAC TAC      4158
Ala Pro Gly Glu Glu Tyr Thr Cys Gly Thr Asn Phe Ala Tyr Tyr Tyr
1345                    1350                1355                1360

TTC ATC AGC TTC TAC ATG CTC TGC GCC TTC CTG ATC ATC AAC CTC TTC      4206
Phe Ile Ser Phe Tyr Met Leu Cys Ala Phe Leu Ile Ile Asn Leu Phe
            1365                1370                1375

GTG GCT GTC ATC ATG GAC AAC TTT GAC TAC CTG ACA CGC GAC TGG TCC      4254
Val Ala Val Ile Met Asp Asn Phe Asp Tyr Leu Thr Arg Asp Trp Ser
        1380                1385                1390

ATC CTG GGC CCT CAC CAC CTG GAC CAC CTG GAG TTC AAG GCC ATC TGG      4302
Ile Leu Gly Pro His His Leu Asp His Leu Glu Phe Lys Ala Ile Trp
            1395                1400                1405

TAT GAC CCA GAG GCC AAG GGG CGA ATC AAG CAC CTG GAC GTG GTG ACC      4350
Tyr Asp Pro Glu Ala Lys Gly Arg Ile Lys His Leu Asp Val Val Thr
        1410                1415                1420

CTG AGA AGG ATC CAG CCC CCT CTG GGC TTC GGG AAG TTC TGT CCA          4398
Leu Arg Arg Ile Gln Pro Pro Leu Gly Phe Gly Lys Phe Cys Pro
    1425                1430                1435            1440
```

```
CAC CGG GTG GCC TGT AAG CGC CTG GTG GGC ATG AAC ATG CCC CTG AAC      4446
His Arg Val Ala Cys Lys Arg Leu Val Gly Met Asn Met Pro Leu Asn
        1445                    1450                    1455

AGT GAC GGC ACG GTC ACC TTC AAT GCC ACG CTC TTT GCC CTG GTG CGC      4494
Ser Asp Gly Thr Val Thr Phe Asn Ala Thr Leu Phe Ala Leu Val Arg
        1460                    1465                    1470

ACG GCC CTC AAG ATC AAG ACA GAA GGT AAC TTC GAG CAG GCC AAC GAG      4542
Thr Ala Leu Lys Ile Lys Thr Glu Gly Asn Phe Glu Gln Ala Asn Glu
        1475                    1480                    1485

GAG CTG AGG GCC ATC ATC AAG ATC TGG AAG ATA ACC AGC ATG AAG          4590
Glu Leu Arg Ala Ile Ile Lys Ile Trp Lys Arg Thr Ser Met Lys
        1490                    1495        1500
                                            (P)

CTA CTG GAC CAG GTC ATC CCT CCC ATA GGA GAT GAC GAG GTG ACC GTG      4638
Leu Leu Asp Gln Val Ile Pro Pro Ile Gly Asp Asp Glu Val Thr Val
        1505                    1510                    1515
                                                                1520

GGG AAG TTC TAC GCC ACA TTC CTC ATC CAG GAG CAC TTC CGG AAG TTC      4686
Gly Lys Phe Tyr Ala Thr Phe Leu Ile Gln Glu His Phe Arg Lys Phe
        1525                    1530                    1535

ATG AAG CGC CAG GAG GAA TAT TAT GGG TAT CGG CCC AAG AAG GAC ACC      4734
Met Lys Arg Gln Glu Glu Tyr Tyr Gly Tyr Arg Pro Lys Lys Asp Thr
        1540                    1545                    1550
```

```
GTG CAG ATC CAG GCT GGG CTG CGG ACC ATA GAG GAG GAG GCG GCC CCT    4782
Val Gln Ile Gln Ala Gly Leu Arg Thr Ile Glu Glu Glu Ala Ala Pro
                    1555              1560              1565

GAG ATC CGC CGC ACC ATC TCA GGA GAC CTG ACC GCC GAG GAG GAG CTG    4830
Glu Ile Arg Arg Thr Ile Ser Gly Asp Leu Thr Ala Glu Glu Glu Leu
              1570          (P)         1575              1580

GAG AGA GCC ATG GTG GAG GCT GCG ATG GAG GAG GAG AGG ATC TTC CGG AGG    4878
Glu Arg Ala Met Val Glu Ala Ala Met Glu Glu Glu Arg Ile Phe Arg Arg
        1585              1590              1595              1600

ACC GGA GGC CTG TTT GGC CAG GTG GAC ACC TTC CTG GAA GAG ACC AAC    4926
Thr Gly Gly Leu Phe Gly Gln Val Asp Thr Phe Leu Glu Glu Thr Asn
        1605              1610              1615

TCC CTA CCC CCG GTG ATG GCC AAC CAA AGA CCG CTC CAG TTT GCT GAG    4974
Ser Leu Pro Pro Val Met Ala Asn Gln Arg Pro Leu Gln Phe Ala Glu
        1620              1625              1630

ATA GAA ATG GAA GAG CTT GAG TCG CCT GTC TTC TTG GAC TTC CCT    5022
Ile Glu Met Glu Glu Leu Glu Ser Pro Val Phe Leu Glu Asp Phe Pro
        1635              1640              1645
```

```
CAA GAC GCA AGA ACC AAC CCT CTC GCT CGT GCC AAT ACC AAC AAC GCC    5070
Gln Asp Ala Arg Thr Asn Pro Leu Ala Arg Ala Asn Thr Asn Asn Ala
1650                     1655                1660

AAT GCC AAT GTT GCC TAT GGC AAC AGC AAC CAT AGC AAC AAC CAG ATG    5118
Asn Ala Asn Val Ala Tyr Gly Asn Ser Asn His Ser Asn Asn Gln Met
1665                     1670            1675                1680

TTT TCC AGC GTC CAC TGT GAA AGG GAG TTC CCG GGA GAG GCG GAG ACA    5166
Phe Ser Ser Val His Cys Glu Arg Glu Phe Pro Gly Glu Ala Glu Thr
          1685                     1690                1695

CCG GCT GCC GGA CGA GGA GCC CTC AGC CAC TCC CAC AGG GCC CTG GGA    5214
Pro Ala Ala Gly Arg Gly Ala Leu Ser His Ser His Arg Ala Leu Gly
       1700                     1705                1710

CCT CAC AGC AAG CCC TGT GCT GGA AAA CTG AAT GGG CAG CTG GTC CAG    5262
Pro His Ser Lys Pro Cys Ala Gly Lys Leu Asn Gly Gln Leu Val Gln
1715                     1720                1725

CCG GGA ATG CCC ATC AAC CAG GCA CCT CCT GCC CCC TGC CAG CAG CCT    5310
Pro Gly Met Pro Ile Asn Gln Ala Pro Pro Ala Pro Cys Gln Gln Pro
       1730                     1735                1740

AGC ACA GAT CCC CCA GAG CGC GGG CAG AGG AGG ACC TCC CTG ACA GGG    5358
Ser Thr Asp Pro Pro Glu Arg Gly Gln Arg Arg Thr Ser Leu Thr Gly
1745                     1750                1755            1760
                                                  (P)
```

```
TCT CTG CAA GAC GAA GCA CCC CAG AGG AGC TCC GAG GGG AGC ACC      5406
Ser Leu Gln Asp Glu Ala Pro Gln Arg Arg Ser Ser Glu Gly Ser Thr
             1765                    1770       (P)      1775

CCC AGG CGC CCG GCT CCT GCT ACA GCT CTG CTG ATC CAA GAG GCT CTG  5454
Pro Arg Arg Pro Ala Pro Ala Thr Ala Leu Leu Ile Gln Glu Ala Leu
         1780                    1785                    1790

GTT CGA GGG GGC CTG GAC ACC TTG GCA GCT GAT GCT GGC TTC GTC ATG  5502
Val Arg Gly Gly Leu Asp Thr Leu Ala Ala Asp Ala Gly Phe Val Met
             1795                    1800                    1805

GCA ACA AGC CAG GCC CTG GTA GAC GCC TGT CAG ATG GAA CCG GAG GAA  5550
Ala Thr Ser Gln Ala Leu Val Asp Ala Cys Gln Met Glu Pro Glu Glu
         1810                    1815                    1820

GTA GAG GTC GCA GCC ACA GAG CTA CTG AAA GAG CGA GAG TCC GTC CAG  5598
Val Glu Val Ala Ala Thr Glu Leu Leu Lys Glu Arg Glu Ser Val Gln
             1825                    1830                    1835                1840

GGC ATG GCC AGT GTC CCG GGA AGC CTG AGC CGC AGG TCC TCC CTG GGC  5646
Gly Met Ala Ser Val Pro Gly Ser Leu Ser Arg Arg Ser Ser Leu Gly
         1845                    1850                    (P)  1855
```

```
AGC CTT GAC CAG GTC CAG GGC TCC CAG GAA ACC CTT ATT CCT CCC AGG    5694
Ser Leu Asp Gln Val Gln Gly Ser Gln Glu Thr Leu Ile Pro Pro Arg
        1860                1865                1870

CCG TGA                                                             5700
Pro End

TGGCTGTGCA GTGTCCACAT GACCAAGGCG AGGGGGACAG TGCGTGCAGA AGCTCAGCCC    5760
TGCATGGCAG CCTCCCTCTG TCTCAGCCCT CCTGCTGAGC TGGGGCGGTC TGGAACCGAC    5820
CAGGAAGCCA GGAGCCTCCC CTGGCCAGCA AGAGGCATGA TTCTAAAGCA TCCAGAAAGG    5880
CCTGGTCAGT GCCACTCCCC AGCAGGACAT TAAAGTCTCT AGGTCTGTGG CAAAAAAAA    5940
AAAAAAAAAA AAAAAAAAAA AAAAA                                         5975
```

FIG. 9(a)-1

```
AGAAGGGAGG GCCGAGCGTGG TGTGTGCGCG CTCGGGGCGCC GGCGGCACCG CCGAGGTCTG        60
TTGGCAAAAG TCGCCCTTGA TGGCGGGCGA GGCGAGGCAG CCGGCGGCGCC GAACAGCCGA       120
CGCGCGCTAG CGGGGTCCGC CCGCCCCTTT CCCAGAGCCC AGCGCCCGCC TTCGCCGCCG       180
CCGCCCGCCCG GTTCGCCCGCC GCCCCGCCC GCGGGTGGCA GCGCCCGCTCG               240
GTCCCCGGCC CCGGGGGCCGG CTGGGGGCCGG GTCGGGGGCGT GTGAGGGGCT TGCTCCCAGC   300
TCGCGAAG                                                                308

ATG GCT GCG GGC CGC CCG CTG GCC TGG ACG CTG ACA CTT TGG CAG GCG        356
Met Ala Ala Gly Arg Pro Leu Ala Trp Thr Leu Thr Leu Trp Gln Ala
  1               5                  10                  15

TGG CTG ATC CTG ATC GGG CCC TCG GAG GAG CCG TTC CCT TCA GCC           404
Trp Leu Ile Leu Ile Gly Pro Ser Ser Glu Glu Pro Phe Pro Ser Ala
             20                  25                  30

GTC ACT ATC AAG TCA TGG GTG GAT AAG ATG CAA GAA GAC CTG GTC ACA       452
Val Thr Ile Lys Ser Trp Val Asp Lys Met Gln Glu Asp Leu Val Thr
             35                  40                  45

CTG GCA AAA ACA GCA AGT GGA GTC CAT CAG CTT GTT GAT ATT TAT GAG       500
Leu Ala Lys Thr Ala Ser Gly Val His Gln Leu Val Asp Ile Tyr Glu
             50                  55                  60
```

| | | | | | | | | | | |
|---|---|---|---|---|---|---|---|---|---|---|
| AAA | TAT | CAA | GAT | TTG | TAT | ACT | GTG | GAA | CCA | AAT | AAT | GCA | CGT | CAG | CTG | 548 |
| Lys | Tyr | Gln | Asp | Leu | Tyr | Thr | Val | Glu | Pro | Asn | Asn | Ala | Arg | Gln | Leu |
| 65 | | | | | 70 | | | | | 75 | | | | | 80 |

| GTG | GAA | ATT | GCA | GCC | AGA | GAC | ATT | GAG | AAG | CTT | CTC | AGC | AAC | AGA | TCT | 596 |
| Val | Glu | Ile | Ala | Ala | Arg | Asp | Ile | Glu | Lys | Leu | Leu | Ser | Asn | Arg | Ser |
| | 85 | | | | | 90 | | | | | 95 | | | | |

| AAA | GCC | CTG | GTG | CGC | CTG | GCT | TTG | GAA | GCA | GAG | AAA | GTT | CAA | GCA | GCC | 644 |
| Lys | Ala | Leu | Val | Arg | Leu | Ala | Leu | Glu | Ala | Glu | Lys | Val | Gln | Ala | Ala |
| | 100 | | | | | 105 | | | | | 110 | | | | |

| CAC | CAA | TGG | AGG | GAA | GAT | TTT | GCA | AGC | AAT | GAA | GTT | GTC | TAC | TAT | AAC | 692 |
| His | Gln | Trp | Arg | Glu | Asp | Phe | Ala | Ser | Asn | Glu | Val | Val | Tyr | Tyr | Asn |
| 115 | | | | | 120 | | | | | 125 | | | | | |

| GCG | AAG | GAT | GAT | CTT | GAT | CCT | GAA | AAA | AAT | GAC | AGT | GAA | CCA | GGC | AGC | 740 |
| Ala | Lys | Asp | Asp | Leu | Asp | Pro | Glu | Lys | Asn | Asp | Ser | Glu | Pro | Gly | Ser |
| 130 | | | | | 135 | | | | | 140 | | | | | |

| CAG | AGG | ATC | AAA | CCT | GTT | TTC | ATT | GAC | GAT | GCT | AAC | TTT | AGA | AGA | CAA | 788 |
| Gln | Arg | Ile | Lys | Pro | Val | Phe | Ile | Asp | Asp | Ala | Asn | Phe | Arg | Arg | Gln |
| 145 | | | | | 150 | | | | | 155 | | | | | 160 |

```
GTA TCC TAT CAG CAC GCA GCT GTC CAT ATC CCC ACT GAC ATC TAT GAA    836
Val Ser Tyr Gln His Ala Ala Val His Ile Pro Thr Asp Ile Tyr Glu
            165                     170                 175

GGA TCG ACA ATC GTG TTA AAC GAA CTC AAC TGG ACA AGT GCC TTA GAT    884
Gly Ser Thr Ile Val Leu Asn Glu Leu Asn Trp Thr Ser Ala Leu Asp
        180                     185                     190

GAC GTT TTC AAA AAT CGA GAG GAA GAC CCT TCA CTG TTG TGG CAG        932
Asp Val Phe Lys Asn Arg Glu Glu Asp Pro Ser Leu Leu Trp Gln
    195                     200                     205

GTG TTT GGC AGT GCC ACT GGC CTG GCC CGG TAT TAC CCA GCT TCT CCA    980
Val Phe Gly Ser Ala Thr Gly Leu Ala Arg Tyr Tyr Pro Ala Ser Pro
210                     215                     220

TGG GTT GAT AAT AGC CGA ACC CCA AAC AAG ATT GAT CTT TAT GAT GTA   1028
Trp Val Asp Asn Ser Arg Thr Pro Asn Lys Ile Asp Leu Tyr Asp Val
225                     230                     235                 240

CGC AGA AGA CCA TGG TAC ATC CAA GGT GCA TCC CCT AAA GAT ATG       1076
Arg Arg Arg Pro Trp Tyr Ile Gln Gly Ala Ser Pro Lys Asp Met
    245                     250                     255

CTT ATT CTG GTG GAT GTG AGT GGA AGC GTT AGT GGA CTG ACA CTC AAA   1124
Leu Ile Leu Val Asp Val Ser Gly Ser Val Ser Gly Leu Thr Leu Lys
        260                     265                     270
```

```
CTC ATC CGG ACA TCC GTC TCC GAA ATG TTG GAA ACC CTC TCA GAT GAT    1172
Leu Ile Arg Thr Ser Val Ser Glu Met Leu Glu Thr Leu Ser Asp Asp
        275                 280                 285

GAT TTT GTG AAC GTG GCT TCA TTT AAC AGC AAT GCT CAG GAT GTA AGC    1220
Asp Phe Val Asn Val Ala Ser Phe Asn Ser Asn Ala Gln Asp Val Ser
        290                 295                 300

TGC TTT CAG CAC CTT GTC CAA GCA AAT GTA AGA AAT AAG AAA GTG TTG    1268
Cys Phe Gln His Leu Val Gln Ala Asn Val Arg Asn Lys Lys Val Leu
305                 310                 315                 320

AAA GAT GCA GTG AAT ATC ACA GCA AAA GGA ATC ACA GAT TAT AAG        1316
Lys Asp Ala Val Asn Ile Thr Ala Lys Gly Ile Thr Asp Tyr Lys
                325                 330                 335

AAG GGC TTT AGT TTT GCT TTT GAG CAG CTG CTT AAT TAT AAT GTA TCC    1364
Lys Gly Phe Ser Phe Ala Phe Glu Gln Leu Leu Asn Tyr Asn Val Ser
        340                 345                 350

AGA GCC AAC TGC AAT AAG ATT ATC ATG TTG TTC ACG GAC GGA GGA GAA    1412
Arg Ala Asn Cys Asn Lys Ile Ile Met Leu Phe Thr Asp Gly Gly Glu
355                 360                 365
```

```
GAG AGA GCC CAG GAG ATA TTT GCC AAA TAC AAT AAA GAC AAG AAA GTA     1460
Glu Arg Ala Gln Glu Ile Phe Ala Lys Tyr Asn Lys Asp Lys Lys Val
370                         375                 380

CGT GTA TTC ACA TTC TCA GTT GGC CAA CAT AAT TAC GAC AGA GGA CCT     1508
Arg Val Phe Thr Phe Ser Val Gly Gln His Asn Tyr Asp Arg Gly Pro
385                         390                 395             400

ATT CAG TGG ATG GCT TGC GAA AAT AAA GGT TAT TAT TAT GAA ATT CCA     1556
Ile Gln Trp Met Ala Cys Glu Asn Lys Gly Tyr Tyr Tyr Glu Ile Pro
        405                         410                 415

TCC ATT GGA GCC ATA AGA ATT AAT ACT CAG GAA TAC CTA GAT GTT CTG     1604
Ser Ile Gly Ala Ile Arg Ile Asn Thr Gln Glu Tyr Leu Asp Val Leu
420                         425                 430

GGA AGA CCG ATG GTT TTA GCA GGA GAC AAA GCT AAG CAA GTC CAA TGG     1652
Gly Arg Pro Met Val Leu Ala Gly Asp Lys Ala Lys Gln Val Gln Trp
        435                         440                 445

ACA AAT GTG TAC CTG GAT GCA CTG GAA CTG GGA CTT GAA GTC ATT ACT GGA 1700
Thr Asn Val Tyr Leu Asp Ala Leu Glu Leu Gly Leu Glu Val Ile Thr Gly
450                         455                 460

ACT CTT CCG GTC TTC AAC ATA ACT GGC CAA TTT GAA AAT AAG ACA AAC     1748
Thr Leu Pro Val Phe Asn Ile Thr Gly Gln Phe Glu Asn Lys Thr Asn
465                         470                 475             480

TTA AAG AAC CAG CTG ATT CTT GGA GTG ATG GGA GTT GAT GTG TCT TTG     1796
Leu Lys Asn Gln Leu Ile Leu Gly Val Met Gly Val Asp Val Ser Leu
        485                         490                 495
```

```
GAA GAT ATT AAA AGA CTG ACA CCA CGT TTT ACA CTC TGC CCC AAT GGC    1844
Glu Asp Ile Lys Arg Leu Thr Pro Arg Phe Thr Leu Cys Pro Asn Gly
        500                 505                 510

TAC TAT TTT GCA ATT GAT CCT AAT GGT TAT GTG TTA TTA CAT CCA AAT    1892
Tyr Tyr Phe Ala Ile Asp Pro Asn Gly Tyr Val Leu Leu His Pro Asn
        515                 520                 525

CTT CAG CCA AAG CCT ATT GGT GTA GGT ATA CCA ACA ATT AAT TTG AGA    1940
Leu Gln Pro Lys Pro Ile Gly Val Gly Ile Pro Thr Ile Asn Leu Arg
        530                 535                 540

AAA AGG AGA CCC AAT GTT CAG AAC CCC AAA TCT CAG GAG CCA GTG ACA    1988
Lys Arg Arg Pro Asn Val Gln Asn Pro Lys Ser Gln Glu Pro Val Thr
        545                 550                 555                 560

TTG GAT TTC CTC GAT GCA GAG TTG GAG AAT GAC ATT AAA GTG GAG ATT    2036
Leu Asp Phe Leu Asp Ala Glu Leu Glu Asn Asp Ile Lys Val Glu Ile
        565                 570                 575
```

```
CGA AAT AAA ATG ATC GAT GGA GAA AGT GGA GAA AAA ACA TTC AGA ACT    2084
Arg Asn Lys Met Ile Asp Gly Glu Ser Gly Glu Lys Thr Phe Arg Thr
        580                 585                 590

CTG GTT AAA TCT CAA GAT GAG AGA TAT ATT GAC AAA GGA AAC AGG ACA    2132
Leu Val Lys Ser Gln Asp Glu Arg Tyr Ile Asp Lys Gly Asn Arg Thr
        595                 600                 605

TAC ACG TGG ACT CCT GTC AAC GGC ACA GAT TAT AGC AGT TTG GCC TTG    2180
Tyr Thr Trp Thr Pro Val Asn Gly Thr Asp Tyr Ser Ser Leu Ala Leu
        610                 615                 620

GTA TTA CCA ACC TAC AGT TTT TAC TAT ATA AAA GCC AAA ATA GAA GAG    2228
Val Leu Pro Thr Tyr Ser Phe Tyr Tyr Ile Lys Ala Lys Ile Glu Glu
        625                 630                 635                 640

ACA ATA ACT CAG GCC AGA TAT TCA GAA ACA CTG AAA CCA GAT AAT TTT    2276
Thr Ile Thr Gln Ala Arg Tyr Ser Glu Thr Leu Lys Pro Asp Asn Phe
        645                 650                 655

GAA GAA TCT GGC TAC ACA TTC CTA GCA CCA AGA GAT TAC TGC AGT GAC    2324
Glu Glu Ser Gly Tyr Thr Phe Leu Ala Pro Arg Asp Tyr Cys Ser Asp
        660                 665                 670

CTT AAA CCT TCA GAT AAT AAC ACT GAA TTT CTT TTA AAT TTC AAT GAG    2372
Leu Lys Pro Ser Asp Asn Asn Thr Glu Phe Leu Leu Asn Phe Asn Glu
        675                 680                 685
```

| | | | | | | | | | | | | | | | |
|---|---|---|---|---|---|---|---|---|---|---|---|---|---|---|---|
| TTT | ATT | GAT | AGA | AAA | ACT | CCA | AAC | AAC | CCA | TCC | TGT | AAT | ACA | GAC | TTG |
| Phe | Ile | Asp | Arg | Lys | Thr | Pro | Asn | Asn | Pro | Ser | Cys | Asn | Thr | Asp | Leu |
| 690 | | | | | | 695 | | | | | 700 | | | | |

2420

| ATT | AAT | AGA | GTC | TTG | CTG | GAT | GCA | GGC | TTT | ACA | AAT | GAA | CTT | GTT | CAA |
|---|---|---|---|---|---|---|---|---|---|---|---|---|---|---|---|
| Ile | Asn | Arg | Val | Leu | Leu | Asp | Ala | Gly | Phe | Thr | Asn | Glu | Leu | Val | Gln |
| 705 | | | | 710 | | | | | 715 | | | | | 720 | |

2468

| AAT | TAC | TGG | AGT | AAG | CAG | AAG | AAT | ATC | AAG | GGA | GTG | AAA | GCA | CGG | TTT |
|---|---|---|---|---|---|---|---|---|---|---|---|---|---|---|---|
| Asn | Tyr | Trp | Ser | Lys | Gln | Lys | Asn | Ile | Lys | Gly | Val | Lys | Ala | Arg | Phe |
| | | 725 | | | | | | 730 | | | | | 735 | | |

2516

| GTT | GTG | ACT | GAT | GGT | GGG | ATT | ACC | AGA | GTT | TAT | CCC | AAA | GAG | GCT | GGA |
|---|---|---|---|---|---|---|---|---|---|---|---|---|---|---|---|
| Val | Val | Thr | Asp | Gly | Gly | Ile | Thr | Arg | Val | Tyr | Pro | Lys | Glu | Ala | Gly |
| 740 | | | | | 745 | | | | | 750 | | | | | |

2564

| GAA | AAT | TGG | CAG | GAA | AAC | CCA | GAG | ACA | TAT | GAA | GAC | AGC | TTC | TAT | AAA |
|---|---|---|---|---|---|---|---|---|---|---|---|---|---|---|---|
| Glu | Asn | Trp | Gln | Glu | Asn | Pro | Glu | Thr | Tyr | Glu | Asp | Ser | Phe | Tyr | Lys |
| 755 | | | | | 760 | | | | | 765 | | | | | |

2612

| AGG | AGC | CTC | GAT | AAT | GAT | AAC | TAC | GTT | TTC | ACT | GCT | CCC | TAC | TTT | AAC |
|---|---|---|---|---|---|---|---|---|---|---|---|---|---|---|---|
| Arg | Ser | Leu | Asp | Asn | Asp | Asn | Tyr | Val | Phe | Thr | Ala | Pro | Tyr | Phe | Asn |
| 770 | | | | | 775 | | | | | 780 | | | | | |

```
AAA AGT GGA CCT GGG GCC TAT GAG TCA GGC ATT ATG GTA AGC AAA GCT   2708
Lys Ser Gly Pro Gly Ala Tyr Glu Ser Gly Ile Met Val Ser Lys Ala
785                 790                 795                 800

GTA GAA ATA TAT ATC CAA GGA AAA CTT CTT GCA CCT GCA GTT GTT GGA   2756
Val Glu Ile Tyr Ile Gln Gly Lys Leu Leu Ala Pro Ala Val Val Gly
            805                 810                 815

ATT AAA ATT GAT GTA AAT TCT TGG ATA GAG AAT TTC ACC AAA ACT TCA   2804
Ile Lys Ile Asp Val Asn Ser Trp Ile Glu Asn Phe Thr Lys Thr Ser
        820                 825                 830

ATC AGG GAT CCG TGT GCT GGT CCA GTT TGT GAC TGC AAA CGA AAC AGT   2852
Ile Arg Asp Pro Cys Ala Gly Pro Val Cys Asp Cys Lys Arg Asn Ser
    835                 840                 845             (P)

GAT GTA ATG GAT TGT GTG ATT CTA GAT GAC GGT GGG TTT CTT TTG ATG   2900
Asp Val Met Asp Cys Val Ile Leu Asp Asp Gly Gly Phe Leu Leu Met
850                 855                 860

GCC AAC CAT GAT GAT TAT ACC AAT CAG ATT GGA AGA TTC TTT GGA GAG   2948
Ala Asn His Asp Asp Tyr Thr Asn Gln Ile Gly Arg Phe Phe Gly Glu
865                 870                 875                 880

ATT GAT CCA AGC TTG ATG AGA CAC CTG GTC AAT ATA TCA GTT TAT GCC   2996
Ile Asp Pro Ser Leu Met Arg His Leu Val Asn Ile Ser Val Tyr Ala
            885                 890                 895
```

```
TTT AAC AAA TCT TAT GAT TAT CAG TCG GTG TGT GAA CCT GGT GCT GCG       3044
Phe Asn Lys Ser Tyr Asp Tyr Gln Ser Val Cys Glu Pro Gly Ala Ala
        900                 905                 910

CCA AAG CAG GGA GCA GGG CAC CGC TCG GCT TAT GTG CCA TCA ATA GCA       3092
Pro Lys Gln Gly Ala Gly His Arg Ser Ala Tyr Val Pro Ser Ile Ala
        915                 920                 925

GAC ATA CTG CAG ATT GGA TGG TGG GCC ACT GCT GCT GCC TGG TCT ATT       3140
Asp Ile Leu Gln Ile Gly Trp Trp Ala Thr Ala Ala Ala Trp Ser Ile
        930                 935                 940

CTT CAG CAG TTT CTG TTG AGT TTG ACT TTT CCA CGG CTC CTT GAG GCA       3188
Leu Gln Gln Phe Leu Leu Ser Leu Thr Phe Pro Arg Leu Leu Glu Ala
        945                 950                 955                 960

GCT GAT ATG GAG GAT GAC TTC ACT GCC TCC ATG TCA AAG CAG AGC           3236
Ala Asp Met Glu Asp Asp Phe Thr Ala Ser Met Ser Lys Gln Ser
        965                 970                 975

TGC ATC ACT GAG CAA ACC CAG TAT TTC TTC GAT AAT GAC AGC AAA TCG       3284
Cys Ile Thr Glu Gln Thr Gln Tyr Phe Phe Asp Asn Asp Ser Lys Ser
        980                 985                 990
```

```
TTC AGT GGG GTA TTA GAC TGT GGG AAT TGT TCC AGA ATC TTT CAT GTA      3332
Phe Ser Gly Val Leu Asp Cys Gly Asn Cys Ser Arg Ile Phe His Val
         995                  1000                 1005

GAA AAG CTC ATG AAC ACC AAT TTA ATA TTC ATA ATG GTA GAG AGC AAG      3380
Glu Lys Leu Met Asn Thr Asn Leu Ile Phe Ile Met Val Glu Ser Lys
        1010                 1015                 1020

GGG ACA TGT CCC TGT GAC ACA CGG CTG CTC ATA CAA GCA GAG CAA ACT      3428
Gly Thr Cys Pro Cys Asp Thr Arg Leu Leu Ile Gln Ala Glu Gln Thr
        1025                 1030                 1035         1040

TCT GAT GGA CCA GAT CCT TGT GAT ATG GTT AAG CAA CCC AGA TAT CGA      3476
Ser Asp Gly Pro Asp Pro Cys Asp Met Val Lys Gln Pro Arg Tyr Arg
        1045                 1050                 1055
```

```
AAA GGG CCA GAT GTC TGC TTT GAC AAC AAT GTC CTG GAG GAT TAT ACT      3524
Lys Gly Pro Asp Val Cys Phe Asp Asn Asn Val Leu Glu Asp Tyr Thr
        1060                        1065                   1070

GAC TGC GGT GGG GTC TCT GGA TTA AAT CCT TCC CTG TGG TCC ATC ATC      3572
Asp Cys Gly Gly Val Ser Gly Leu Asn Pro Ser Leu Trp Ser Ile Ile
        1075                       1080                    1085

GGG ATA CAG TTT GTA CTG CTT TGG CTG GTT TCT GGC AGC AGA CAC TGC      3620
Gly Ile Gln Phe Val Leu Leu Trp Leu Val Ser Gly Ser Arg His Cys
        1090                       1095                    1100

CTG TTA TGA                                                          3629
Leu Leu End
1105

CCTTCTAAAA CCAAATCTCC ATAATTAAAC TCCAGACCCT GCCACAACAT GATCCCTCCG    3689

TTATGTTAAA GTAGGGTCAA CTGTTAAATC AGAACATTAG CTGGGCCTCT GCCATGGCAG    3749

AGCCCTAAGG CGCAGACTCA TCAGGCACCC ACTGGCTGCA TGTCAGGGTG TCC           3802
```

FIG. 9(f)-2

RECOMBINANT PRODUCTION OF MAMMALIAN CALCIUM CHANNEL GAMMA SUBUNITS

This is a continuation of application Ser. No. 07/482,384, filed Feb. 20, 1990, now U.S. Pat. No. 5,386,025.

The work was supported in part by the Government under Grants HL-37187, HL-14388 and HL-39265 awarded by the National Institutes of Health (DHHS). The Government has certain rights in the invention.

TECHNICAL FIELD

The present invention relates to calcium channel compositions and component peptides thereof, as well as methods of making and using same.

Background of the Invention

Calcium channels are membrane-spanning, multisubunit proteins that allow controlled entry of $Ca^{+2}$ ions into cells from the extracellular fluid. All cells throughout the animal kingdom, and at least some bacterial, fungal and plant cells, possess one or more types of calcium channel.

The most common type of calcium channel is voltage-dependent. In a voltage-dependent channel, the "opening" which allows there to begin an influx of $Ca^{+2}$ ions into the cells requires a depolarization to a certain level of the potential difference between the inside of the cell bearing the channel and the extracellular medium bathing the cell. The rate of influx of $Ca^{+2}$ into the cell depends on this potential difference. All "excitable" cells in animals, such as neurons of the central nervous systems, peripheral nerve cells, and muscle cells, including those of skeletal muscles, cardiac muscles, and venous and arterial smooth muscles, have voltage-dependent calcium channels.

Calcium channels are physiologically important because the channels have a central role in regulating intracellular $Ca^{+2}$ levels, which levels are important for cell viability and function. Thus, intracellular $Ca^{+2}$ concentrations are implicated in a number of vital processes in animals, such as neurotransmitter release, muscle contraction, pacemaker activity, and secretion of hormones and other substances.

A number of compounds useful in treating various diseases in animals, including humans, are thought to exert their beneficial effects by modulating functions of voltage-dependent calcium channels. Many of these compounds bind to calcium channels and block, or reduce the rate of, influx of $Ca^{+2}$ into cells in response to depolarization of the inside and outside of the cells.

An understanding of the pharmacology of compounds that interact with calcium channels, and the ability to rationally design compounds that will interact with calcium channels to have desired therapeutic effects, have been hampered by a lack of understanding of the structure of channel subunits and the genes that code for them. Thus, it has not been possible to obtain the large amounts of highly purified channel subunits that are required to understand, at the molecular level, the nature of the subunits and their interactions with one another, with the cell membranes across which the channels allow $Ca^{+2}$ ions to pass, with $Ca^{+2}$ and other ions, and with low molecular weight compounds that affect channel function. For example, with the availability of large amounts of purified calcium channel subunits, functional channels could be prepared and used to screen the effects of compounds on channel function, thereby providing a basis for the design of therapeutic agents which affect the calcium channel, or various combinations of channel subunits could be crystallized and have their structures determined to high resolution employing X-ray or neutron diffraction techniques, providing yet another basis for rational design of therapeutic agents that affect channel function.

Certain diseases, such as Lambert-Eaton Syndrome, involve autoimmune interactions with calcium channels. The ready availability of each of the calcium channel subunits would make possible immunoassays for the diagnosis of such diseases and an understanding of them at the molecular level that could lead to effective methods of treatment.

The lack of information on genes that code for calcium channel subunits has prevented the understanding of the molecular properties of the mature calcium channel subunits and their precursor proteins (i.e., the mature subunits with signal peptides appended to the amino-terminus) and the regulation of expression of calcium channel subunits. An understanding of these properties, and of how expression of calcium channel subunit genes is regulated, may provide the basis for designing therapeutic agents which have beneficial effects through affecting calcium channel function or concentration. Furthermore, the availability of sequences of genes coding for calcium channel subunits would make possible the diagnosis of defects in genes coding for such subunits, which might underlie a number of diseases.

The availability of a DNA with the sequence of a segment of at least about 14 and more preferably at least about 30 nucleotides of a cDNA encoding a subunit of a calcium channel from the cells of a tissue of an animal would make possible the isolation and cloning of cDNAs, and possibly genomic DNAs, coding for the corresponding subunit of different calcium channels from the same or different tissues and animals of the same or different species. The availability of the sequences of numerous full-length cDNAs coding for corresponding subunits of calcium channels from a variety of tissues and animal species would contribute to elucidating structure-function relationships in the subunits. This knowledge, in turn, would be useful in the design of therapeutic agents whose activities are exerted through binding to calcium channels.

In skeletal muscle, where voltage-dependent calcium channels have been best characterized, voltage-dependent calcium channels are thought to consist of two large subunits, of between about 130 and about 200 kilodaltons ("kD") in molecular weight, and a number (generally thought to be two or three) of different smaller subunits, of less than about 60 kD in molecular weight. At least one of the larger subunits and possibly some of the smaller are glycosylated. Some of the subunits are capable of being phosphorylated. There has been confusion in the art concerning the naming of the various subunits of voltage-dependent calcium channels.

The two large subunits of voltage-dependent calcium channels are designated herein the "$\alpha_1$-subunit" and the "$\alpha_2$-subunit".

The $\alpha_1$-subunit is not detectably changed in molecular weight when treated with dithiothreitol ("DTT") or with enzymes which catalyze removal of N-linked sugar groups from glycosylated proteins. The $\alpha_1$-subunit has a molecular weight of about 150 to about 170 kD when analyzed by sodium dodecylsulfate ("SDS")-polyacrylamide gel electrophoresis ("PAGE") after isolation from mammalian muscle tissue and has specific binding sites for various 1,4-dihydropyridines ("DHPs") and phenylalkylamines.

The $\alpha_2$-subunit is somewhat less well characterized than the $\alpha_1$-subunit, although recent work by Ellis et al. (see PCT Application No. WO 89/09834 and *Science*, 241, 1661–1664 (1988)), has provided a great deal of additional information concerning this subunit. The molecular weight of the $\alpha_2$-subunit is at least about 130–150 kD, as determined by SDS-PAGE analysis in the presence of DTT after isolation from mammalian muscle tissue. However, in SDS-PAGE under non-reducing conditions (in the presence of N-ethylmaleimide), the $\alpha_2$-subunit migrates with a band of about 160–190 kD. It is presently believed that the smaller fragment (of about 30 kD), which appears to be released upon reduction of the $\alpha_2$-subunit, is the carboxy terminus of the primary translation product of the $\alpha$2-subunit mRNA. Regardless, however, of whether the two fragments are different subunits of the calcium channel or whether both fragments are products of the same gene (and, consequently, the $\alpha_2$-subunit is about 160–190 kD and is split into (at least) two fragments upon reduction), there is evidence that the $\alpha_2$-subunit, whatever its size, and the corresponding fragment produced under reducing conditions, whether part of the $\alpha_2$-subunit or not, are glycosylated with at least N-linked sugars. In addition there is evidence that the $\alpha$2-subunit and the corresponding fragment produced under reducing conditions do not have specified binding sites for 1,4-dihydropyridines and phenylalkylamines, which species are known to bind to the $\alpha_1$-subunit.

The $\beta$-subunit of the calcium channel has only recently been characterized as having an apparent molecular mass of 52–65 kD (as determined by SDS-PAGE analysis). It is comprised of consensus phosphorylation sites and has been shown by biochemical methods to be phosphorylated. This subunit is insensitive to reducing conditions.

The $\gamma$-subunit of the calcium channel has not been observed in all purified preparations, depending on the source of material analyzed, the investigating laboratory, and so on. Because of its irregular appearance in the hands of some investigators, this particular subunit also remains relatively poorly characterized. The native material appears to be a glycoprotein with an apparent molecular mass of 30–33 kD, as determined by SDS-PAGE analysis. The native protein is believed to be glycosylated since its apparent molecular mass decreases after digestion with neuraminidase followed by endoglycosidase F.

Reference herein to the precursor of an $\alpha_1$-subunit means the protein with the amino acid sequence corresponding to the sequence of the full-length mRNA which, upon translation, results, ultimately, in $\alpha_1$-subunit resident as part of a calcium channel in a cell membrane. The precursor protein is converted by various, not presently well understood, processing steps to produce the $\alpha_1$-subunit.

Similarly, reference herein to the precursor of an $\alpha_2$-subunit means the protein with the amino acid sequence corresponding to the sequence of the full-length mRNA which, upon translation, results, ultimately, in $\alpha_2$-subunit resident as part of a calcium channel in a cell membrane. The precursor protein is converted by various processing steps into the $\alpha_2$-subunit. As with the $\alpha_1$-subunit, the details of the processing between the precursor and the mature $\alpha_2$-subunit are not clear, but the processing presumably involves at least removal of a leader sequence (i.e., a signal peptide), glycosylation, and cleavage to yield what is now thought to be $\delta$-subunit of the calcium channel.

Similarly, reference herein to the precursor of a $\beta$-subunit means the protein with the amino acid sequence corresponding to the sequence of the full-length mRNA which, upon translation, results ultimately, in $\beta$-subunit resident as part of a calcium channel in a cell membrane. The precursor protein is converted by various, not presently well understood, processing steps into the $\beta$-subunit.

Similarly, reference herein to the precursor of a $\gamma$-subunit means the protein with the amino acid sequence corresponding to the sequence of the full-length mRNA which, upon translation, results ultimately, in $\gamma$-subunit resident as part of a calcium channel in a cell membrane. The precursor protein is converted by various, not presently well understood, processing steps into the $\gamma$-subunit.

The cDNA and corresponding amino acid sequence of the $\alpha_1$-subunit precursor of a rabbit back skeletal muscle calcium channel has been reported. See Tanabe et al., *Nature* 328, 313–318 (1987).

The cDNA and corresponding amino acid sequences of the $\alpha_2$-subunit precursor of a rabbit back skeletal muscle calcium channel and a human neuronal calcium channel have also been reported. See Ellis, et al., PCT Application No. WO 89/09834 (1989) and *Science* 241, 1661–1664 (1988).

The cDNA and corresponding amino acid sequence of the $\beta$-subunit precursor of a rabbit back skeletal muscle calcium channel has also been reported. See Ruth et al., *Science* 245, 1115–1118 (1989).

Up to now, however, the cDNA and corresponding amino acid sequence of the $\gamma$-subunit precursor of a calcium channel have not been reported in the literature.

Calcium channel activity, measured electrophysiologically by voltage-clamp techniques, has been induced in *Xenopus laevis* oocytes when total mRNA isolated from mammalian brain or cardiac muscle is injected into the oocytes. Also, it has been reported that calcium channel-containing preparations, when reconstituted into lipid bilayers, confer voltage-dependent calcium channel activity on the bilayers.

However, there is no evidence that any one of the calcium channel subunits alone provides a natively functional calcium channel in oocytes, lipid bilayers or any other situation. It has been recently reported by Hofmann, et al., *Trends in Pharmacology. Sci.* 8, 393–398 (1987) that mRNA prepared using the cDNA of $\alpha_1$-subunit obtained by Tanabe, et al. was unable to induce calcium channel activity in *Xenopus laevis* oocytes.

SUMMARY OF THE INVENTION

In accordance with the present invention, there is provided the cDNA and corresponding amino acid sequence of the $\gamma$-subunit precursor of a calcium channel.

There are now available well-characterized cDNA clones encoding each of the four calcium channel subunits, thus enabling one to incorporate various combinations of such cDNAs into recombinant expression systems. In this way, one can assess the contribution of the various calcium channel subunits to the transport and regulation of calcium ions.

A method for the production of the $\gamma$-subunit of an animal calcium channel by transforming a eukaryotic cell with heterologous DNA encoding the $\gamma$-subunit of a mammalian calcium channel transformed and expressing the heterologous DNA is provided.

The method for the production of the $\gamma$-subunit of an animal calcium channel in that the $\gamma$-subunit is rabbit skeletal muscle subunit as well as the method in that the $\gamma$-subunit that has the amino acid sequence set forth in FIG. 1, is also provided.

A eukaryotic cell with an heterologous calcium channel, that is prepared by administering to the cell a first composition containing a first RNA or cDNA that is translatable in said cell into the precursor of the γ-subunit of a calcium channel of an animal of a first species, and at least one of a second composition selected from among:

- a second composition containing RNA or cDNA that is translatable in the cell into the precursor of the α₁-subunit of a calcium channel of an animal of a second species,
- a third compositions containing RNA or cDNA that is translatable in the cell into the precursor of the α₂-subunit of a calcium channel of an animal of a third species,
- a fourth RNA or cDNA that is translatable in the cell into the precursor of the β-subunit of a calcium channel of an animal of a fourth species, in which the first, second, third and fourth species can be the same or different are provided.

In particular, such cells in which the α₁-subunit is of a mammal of a first species, the α₂-subunit is of a mammal of a second species, the β-subunit is of a mammal of a third species, and the γ-subunit is of a mammal of a fourth species, and wherein the first, second, third and fourth species are the same or different are provided. Also provided are cells in which the first, second, third and fourth species are the same, and cells in which the α₁-subunit is of a skeletal muscle, cardiac or neuronal calcium channel, the α₂-subunit is of a skeletal muscle, cardiac or neuronal calcium channel, the β-subunit is of a skeletal muscle, cardiac or neuronal calcium channel, and the γ-subunit is of a skeletal muscle, cardiac or neuronal calcium channel.

A method for the production of a heterologous calcium channel by administering to a eukaryotic cell a first composition containing a first RNA or cDNA that is translatable in the cell into the precursor of the γ-subunit of a calcium channel of an animal of a first species, and at least one of a second composition selected from among:

- a second composition containing RNA or cDNA that is translatable in the cell into the precursor of the α₁-subunit of a calcium channel of an animal of a second species,
- a third composition containing RNA or cDNA that is translatable in the cell into the precursor of the α₂-subunit of a calcium channel of an animal of a third species, and
- a fourth composition containing RNA or cDNA that is translatable in the cell into the precursor of the β-subunit of a calcium channel of an animal of a fourth species; and thereafter expressing the RNA or cDNA.

Also provided, is this method in which the cell is an oocyte of *Xenopus laevis*, and also this method in which the α₁-subunit is of a mammal of a first species, the α₂-subunit is of a mammal of a second species, the β-subunit is of a mammal of a third species, and the γ-subunit is of a mammal of a fourth species. The first, second, third and fourth species are the same or different. The method in which the first, second, third and fourth species are the same, and the method in which the α₁-subunit is of a skeletal muscle, cardiac or neuronal calcium channel, the α₂-subunit is of a skeletal muscle, cardiac or neuronal calcium channel, the β-subunit is of a skeletal muscle, cardiac or neuronal calcium channel, and the γ-subunit is of a skeletal muscle, cardiac or neuronal calcium channel are also provided.

A method for preparing an heterologous calcium channel, by transforming a eukaryotic cell with a first cDNA that codes for the precursor of the γ-subunit of a calcium channel of an animal of a first species, and at least one of a second cDNA selected from among

- a second cDNA that codes for the precursor of the α₁-subunit of a calcium channel of an animal of a second species,
- a third cDNA that codes for the precursor of the α₂-subunit of a calcium channel of an animal of a third species,
- a fourth cDNA that codes for the precursor of the β-subunit of a calcium channel of an animal of a fourth species, and thereafter expressing the DNA encoding the subunits. The first, second, third and fourth species can be the same or different, with the proviso that at least one of the precursors of the α₁-subunit, α₂-subunit, β-subunit and γ-subunit is foreign to the cell.

This method in which the cell is a yeast cell, in particular, *P. pastoris* or *S. cerevisiae*, or is a mammalian cell, is also provided. Such methods in which the α₁-subunit is of a mammal of a first species, the α₂-subunit is of a mammal of a second species, the β-subunit is of a mammal of a third species, and the γ-subunit is of a mammal of a fourth species are also provided. The first, second, third and fourth species are the same or different. In particular, methods in which each of the first, second, third and fourth mammals are rabbit or human and methods in which each of the α₁-subunit, α₂-subunit, β-subunit and γ-subunit are derived from skeletal muscle calcium channel are provided.

Substantially pure γ-subunits of animal calcium channels, particularly mammalian calcium channels, are also provided. Such subunits that are a subunit of a skeletal muscle calcium channel, particularly a rabbit skeletal muscle calcium channel are provided.

Such substantially pure subunits that are made by expressing, in a eukaryotic cell, DNA encoding a protein that has the acid sequence set forth in FIG. 1, particularly amino acids 1–222, are provided. The eukaryotic cells include cells, such as yeast cells and mammalian cells.

BRIEF DESCRIPTION OF THE FIGURES

FIGS. 1(a)-1, 1(a)-2, and 1(b) provide the cDNA nucleotide sequence and the amino acid sequence for the γ-subunit of a calcium channel.

FIG. 2 is a restriction map of a cDNA sequence which encodes the β-subunit of a calcium channel, and shows the orientation of various cDNAs encoding the β-subunit sequence.

FIG. 3 is a restriction map of a cDNA sequence which encodes the γ-subunit of a calcium channel, and shows the orientation of various cDNAs encoding the γ-subunit sequence.

FIGS. 4(a)-1, 4(a)-2, 4(b)-1, 4(b)-2, 4(c)-1, and 4(c)-2 provide the amino acid sequence for, and a nucleotide sequence encoding the β-subunit of a calcium channel.

FIGS. 5A to 5J provide raw data from which the amino acid sequence for the first nine residues at the N-terminus of the γ-subunit of a calcium channel was ascertained.

FIGS. 8(a)-1 and -2 to 8(i)-1 and -2, and 8(j) provide the amino acid sequence for, and a nucleotide sequence encoding the α₁-subunit of a calcium channel.

FIGS. 9(a)-1 and -2 to 9(f)-1 and -2 provides the amino acid sequence for, and a nucleotide sequence encoding the α₂-subunit of a calcium channel.

DETAILED DESCRIPTION OF THE INVENTION

Figure 5A:
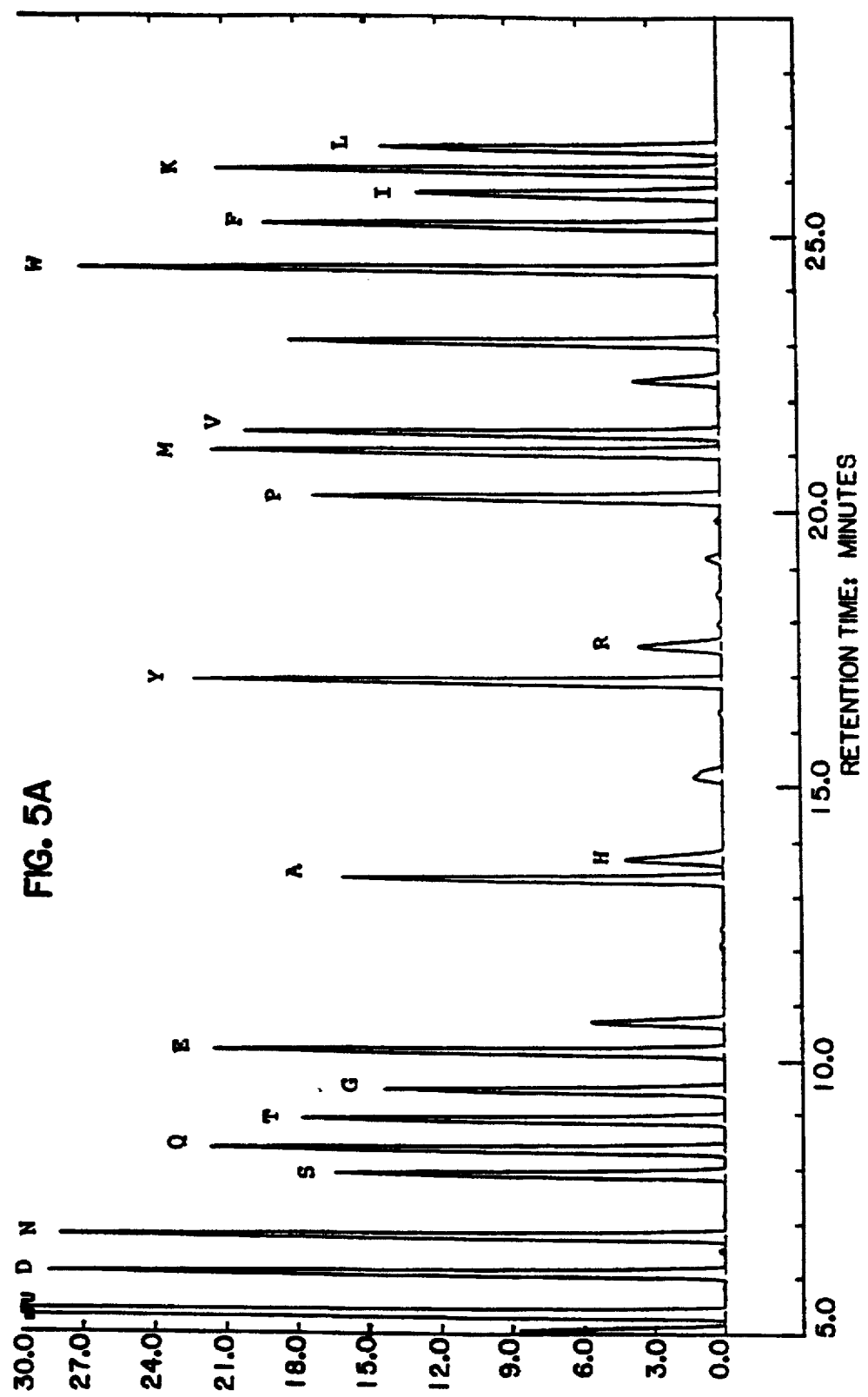
Figure 5B:
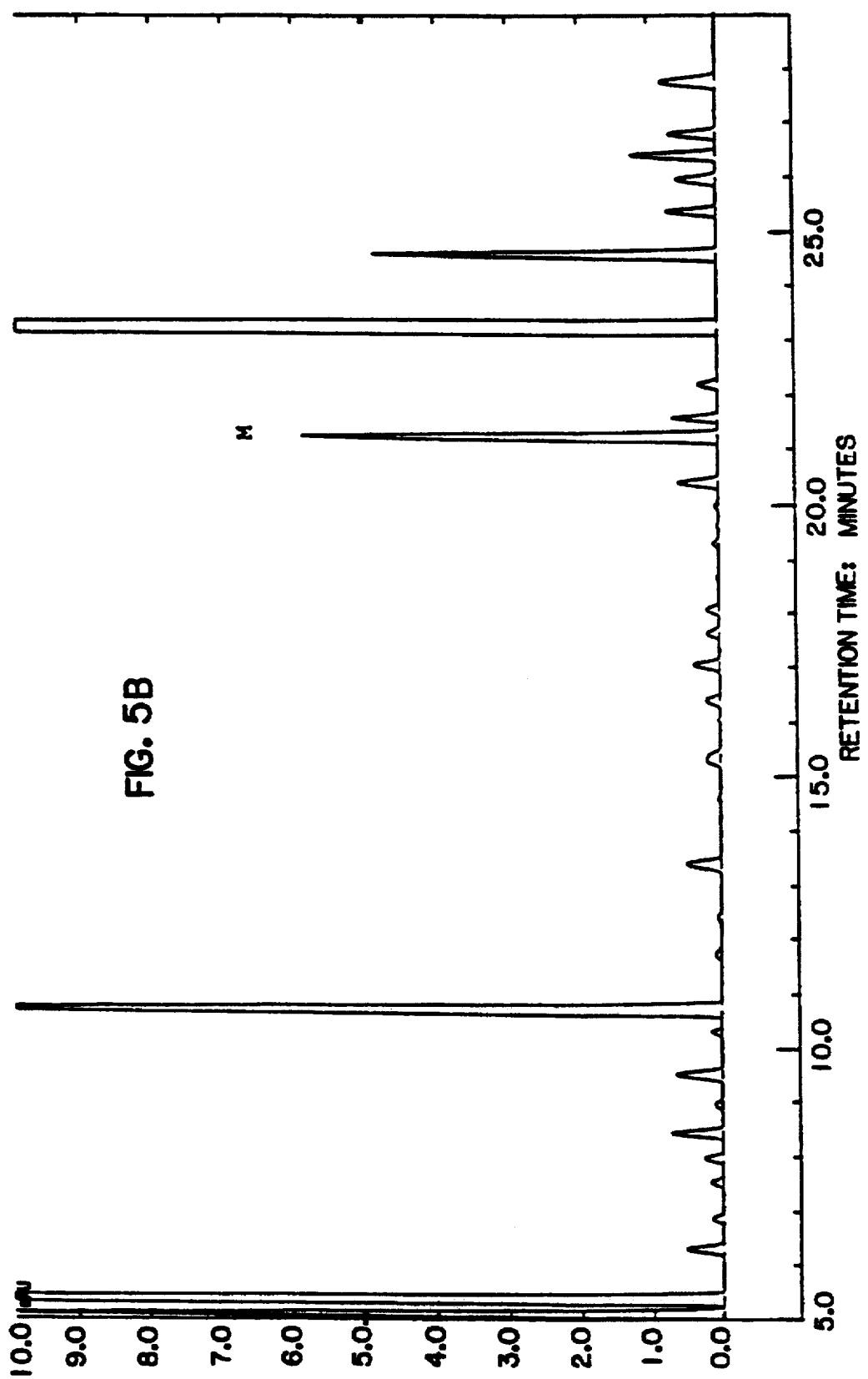
Figure 5C:
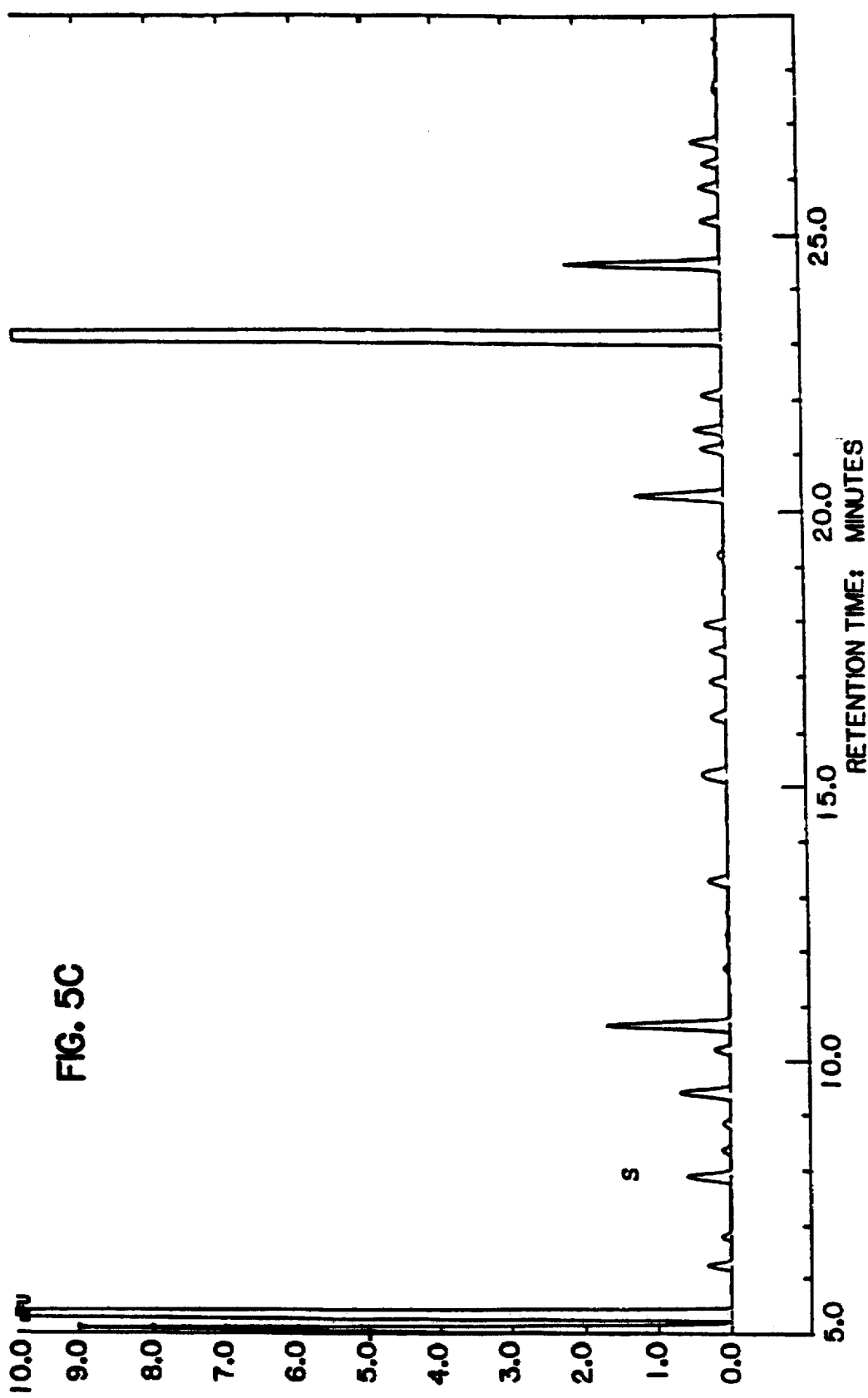
Figure 5E:
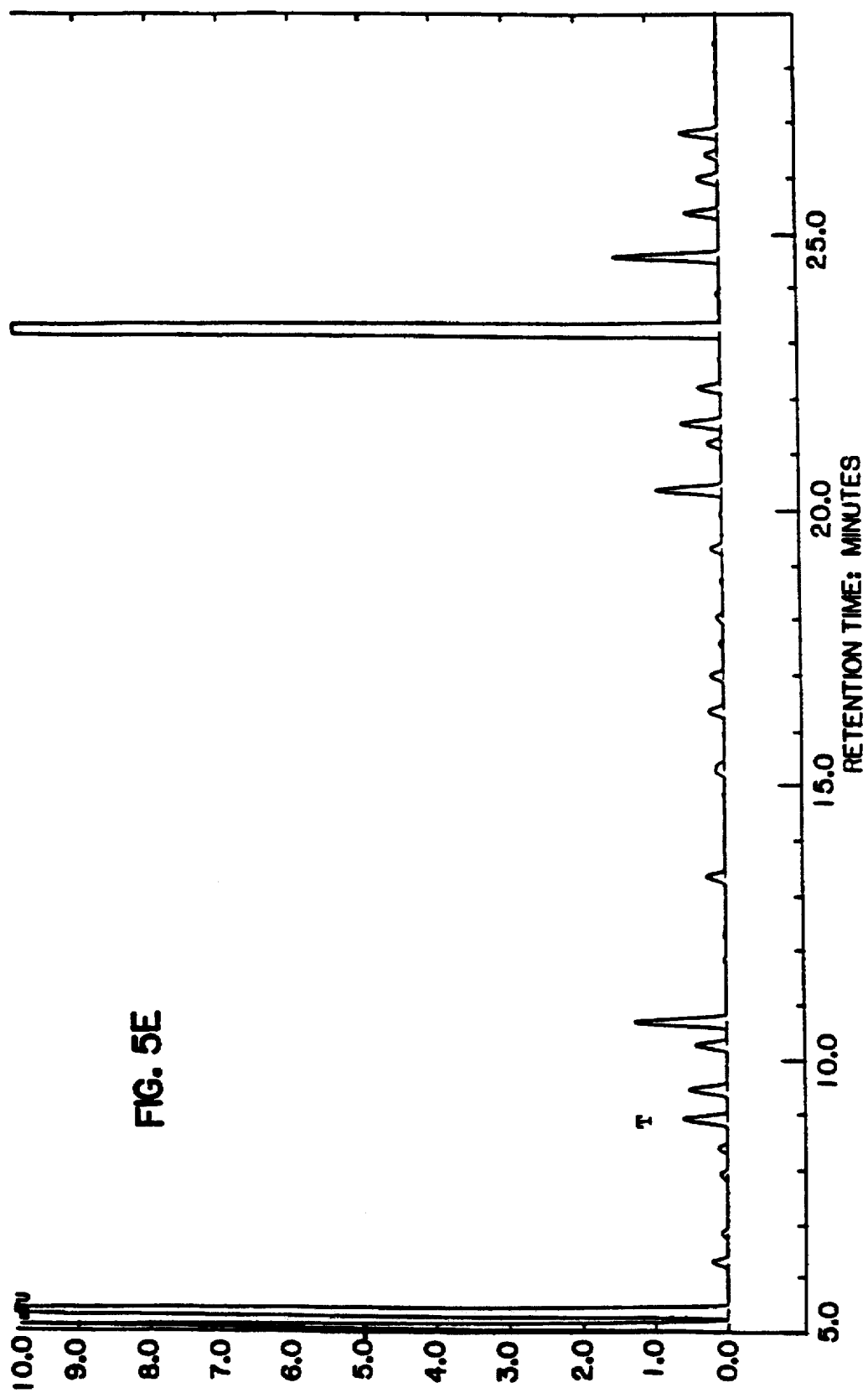
Figure 5F:
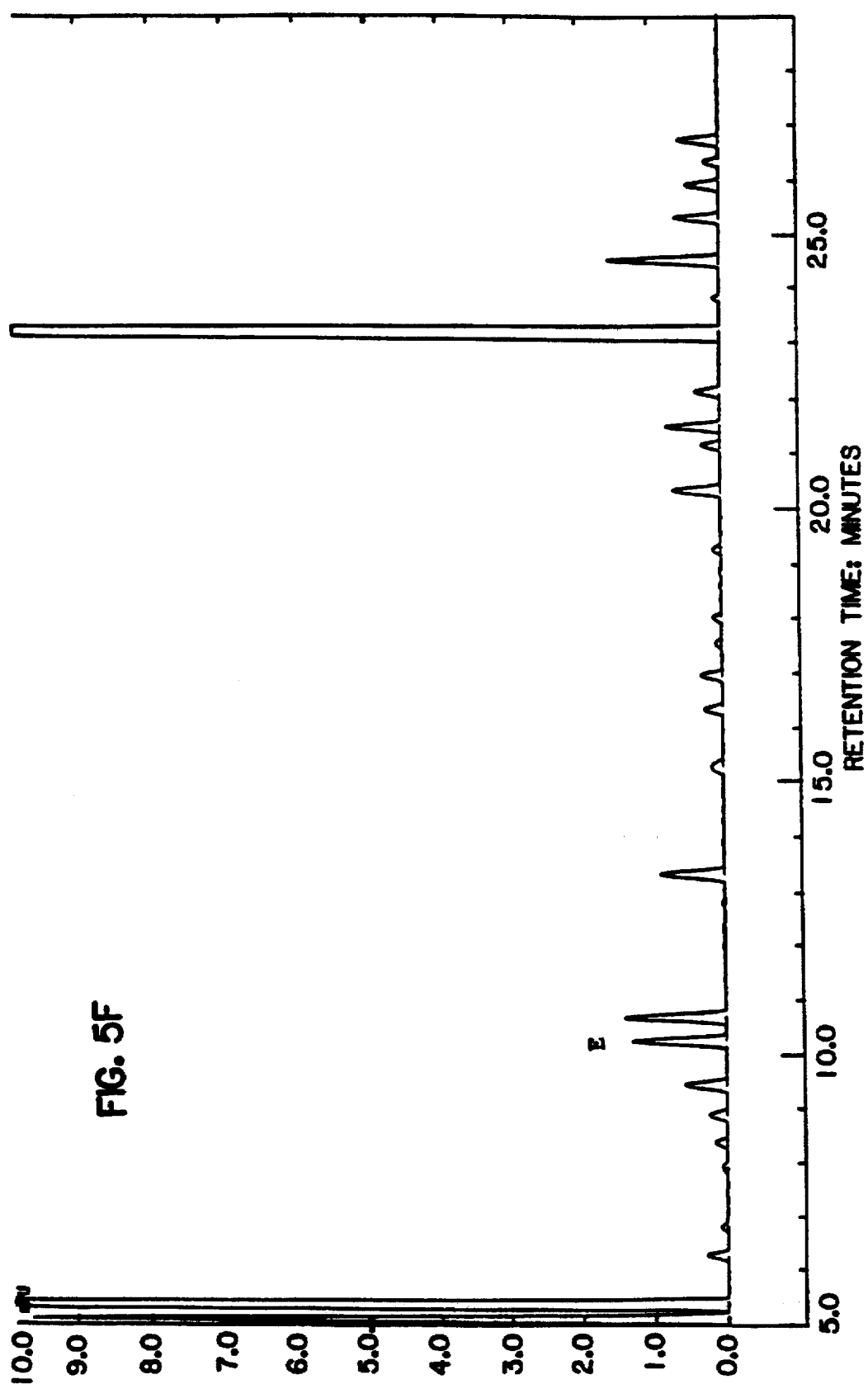
Figure 5G:
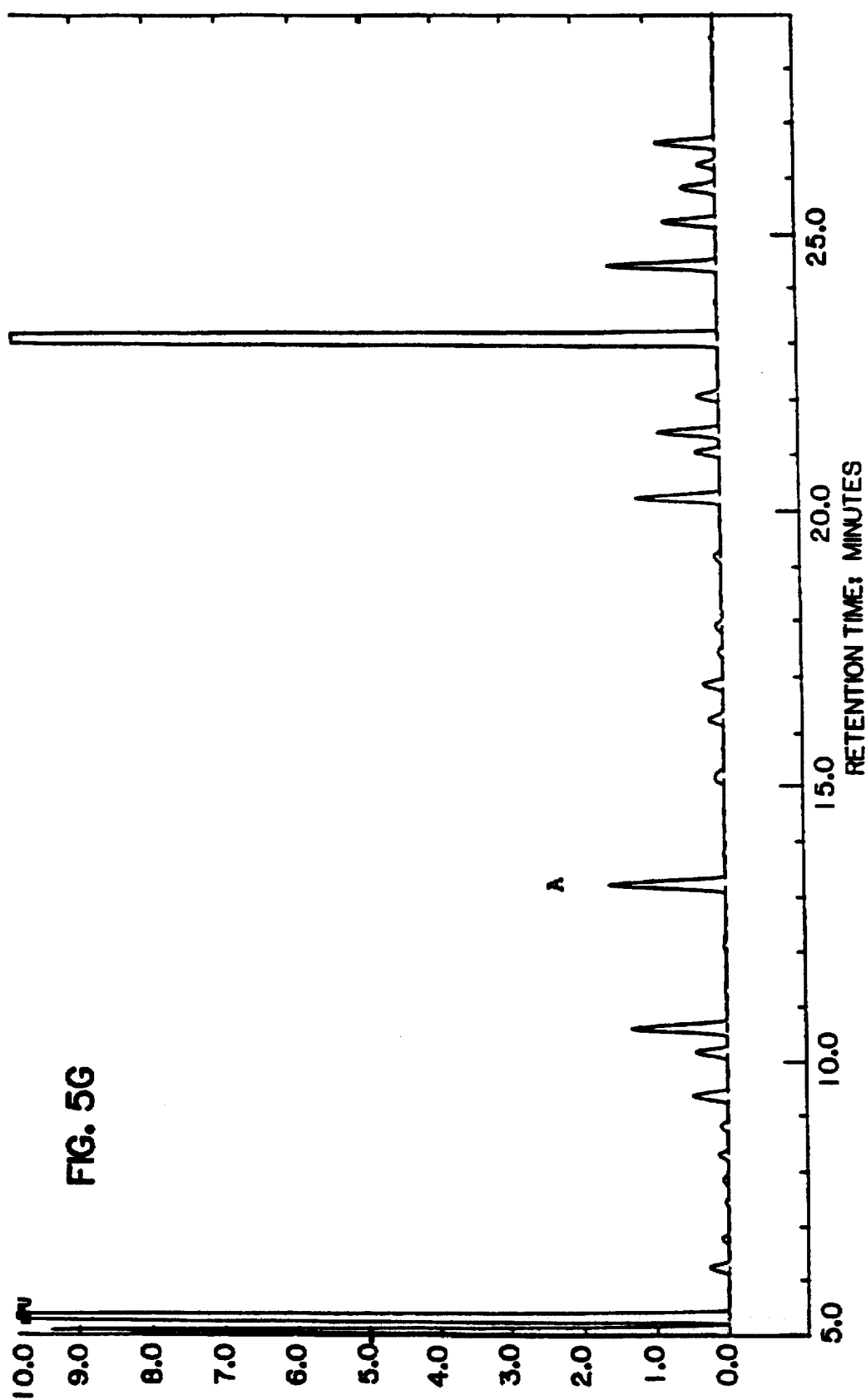
Figure 5H:
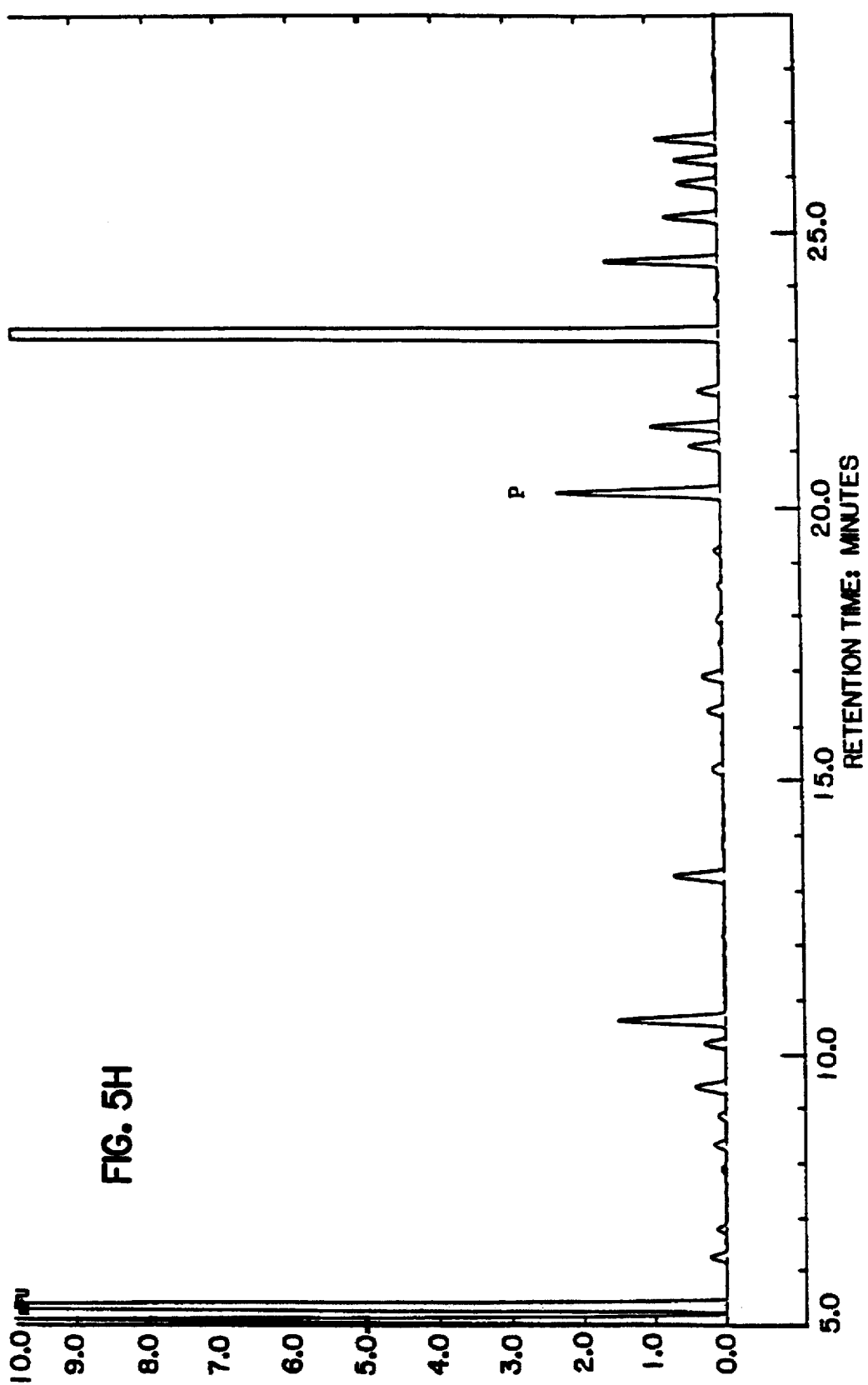
Figure 51:
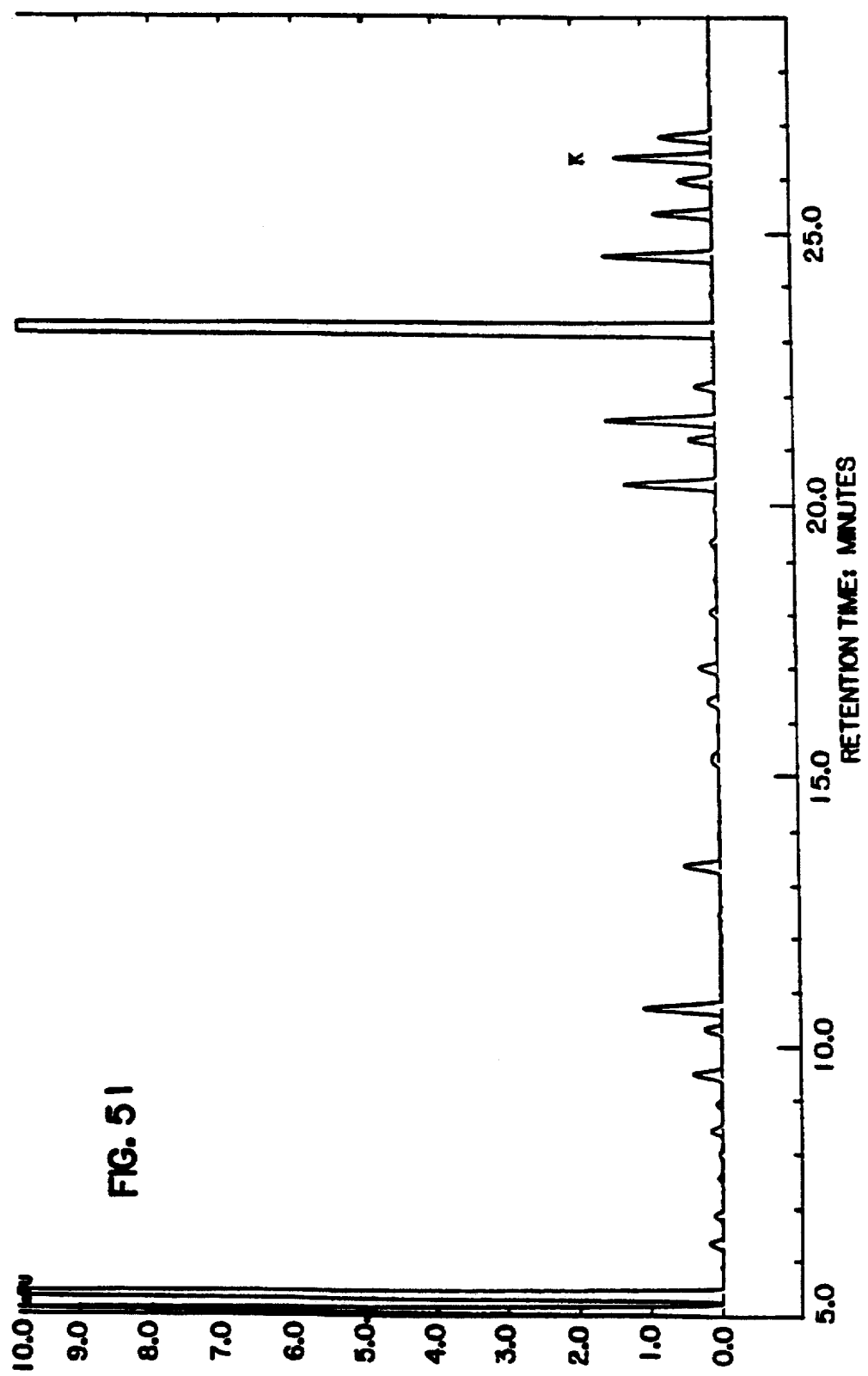
Figure 5J:
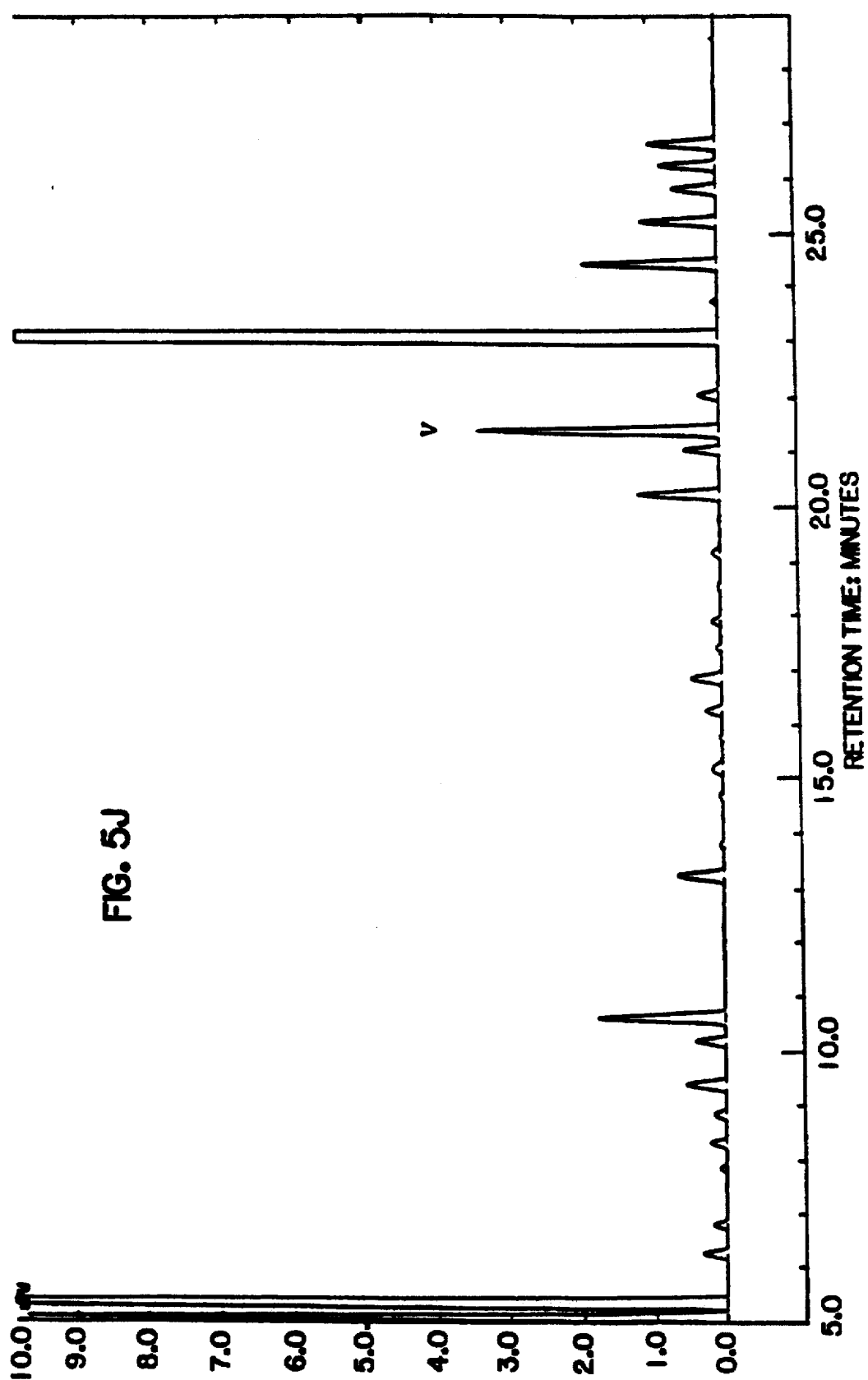

In accordance with the present invention, we have discovered a cDNA which codes for the γ-subunit of an animal calcium channel (see Sequence ID NO. 1).

Thus in one of its aspects, the invention is a DNA fragment which comprises a cDNA which codes for the γ-subunit of an animal calcium channel, and the RNA, coding for such a subunit, made upon transcription of such a DNA according to the invention.

In another of its aspects, the invention is a substantially pure γ-subunit of an animal calcium channel.

By a "substantially pure" subunit or protein is meant a subunit or protein that is sufficiently free of other polypeptide contaminants to be considered homogeneous by SDS-PAGE or to be unambiguously sequenced.

In another of its aspects, the invention entails an eukaryotic cell with an heterologous calcium channel, said cell made by a process comprising administering to said cell a first composition, which consists essentially of a first RNA or cDNA which is translatable in said cell into the precursor of the γ-subunit of a calcium channel of an animal of a first species, and at least one of a second composition selected from the group consisting essentially of a second RNA or cDNA which is translatable in said cell into the precursor of the α₁-subunit of a calcium channel of an animal of a second species, a third RNA or cDNA which is translatable in said cell into the precursor of the α₂-subunit of a calcium channel of an animal of a third species, and a fourth RNA or cDNA which is translatable in said cell into the precursor of the β-subunit of a calcium channel of an animal of a fourth species, wherein said first, second, third and fourth species can be the same or different. Preferred cells for this purpose are *Xenopus laevis* oocytes.

In yet another of its aspects, the present invention entails a method for preparing an heterologous calcium channel by expressing the RNA or cDNA administered to the above-described eukaryotic cells.

In another of its aspects, the invention entails a method for assaying a compound for calcium channel agonist or antagonist activity which comprises electrophysiologically measuring the calcium channel activity of an RNA- or cDNA-containing eukaryotic cell prepared as described above when such cell is exposed to a solution of the compound being tested for such activity. For similar methods applied with *Xenopus laevis* oocytes and acetylcholine receptors, see e.g., Mishina et al. *Nature* 313, 364 (1985) and, with such oocytes and sodium channels, see Noda et al., *Nature* 322, 826–828 (1986).

In a further of its aspects, the invention is an eukaryotic cell containing a DNA which comprises a cDNA which can be expressed to make the γ-subunit of a calcium channel. Such a cell according to the invention can also contain at least one of the following additional DNA fragments selected from the group consisting essentially of:

a second cDNA which codes for the precursor of the α₁-subunit of a calcium channel of an animal of a second species, a third cDNA which codes for the precursor of the α₂-subunit of a calcium channel of an animal of a third species, and a fourth cDNA which codes for the precursor of the β-subunit of a calcium channel of an animal of a fourth species, wherein said first, second, third and fourth species can be the same or different. Preferably, the α₁-subunit, the α₂-subunit, the β-subunit or the γ-subunit made from such cDNA in such a cell will be foreign to the cell, i.e., will have an amino acid sequence which differs from that of any calcium channel α₁-subunit, α₂-subunit, β-subunit or γ-subunit which occurs in a cell of the same type which does not contain a DNA from which the α₁-subunit, the α₂-subunit, the β-subunit or the γ-subunit encoded by such a cDNA is expressed. Preferred among such cells are those of mammalian origin, such as COS cells, NIH3T3 cells, mouse L cells or the like, or those of yeast such as *S. cerevisiae*, *P. pastoris*, or *C. tropicalis*. Methods of making such cells of the invention, i.e., by transforming cells with suitable heterologous DNAs, to be maintained in the cell as episomes or integrated into chromosomal DNA of the cell, and then culturing transformants or subculturing (or passaging, in the case of mammalian cells) from such a culture or a subculture thereof, are well known to those of ordinary skill in the art.

In yet another aspect of the present invention, there is provided a method for the production of the γ-subunit of a calcium channel, comprising expressing the cDNAs contained in the eukaryotic cells as described above.

Among such cDNA-containing cells of the invention, the invention entails also an eukaryotic cell with an heterologous calcium channel, said calcium channel made by a process comprising expression of a first cDNA, which codes for the precursor of the γ-subunit of a calcium channel of an animal of a first species, and at least one of the following additional DNA fragments selected from the group consisting essentially of:

a second cDNA which codes for the precursor of the α₁-subunit of a calcium channel of an animal of a second species, a third cDNA which codes for the precursor of the α₂-subunit of a calcium channel of an animal of a third species, and a fourth cDNA which codes for the precursor of the β-subunit of a calcium channel of an animal of a fourth species, wherein said first, second, third and fourth species can be the same or different. Usually at least one of said precursors of said α₁-subunit, α₂-subunit, β-subunit and γ-subunit is foreign to said cell. Again, preferred among such cells are those of mammalian origin or those of yeast such as *S. cerevisiae*, *P. pastoris* or *C. tropicalis*. In a preferred embodiment, such a cell will also contain another heterologous gene, which comprises a transcriptional control element (e.g., a promoter or promoter/enhancer combination), which is active in said cell and the transcriptional activity of which responds, either directly or indirectly, to an ion or molecule capable of entering said cell through a functional calcium channel (e.g., $Ca^{++}$, $Ba^{++}$, $Ca^{++}$ ionophores), linked operatively for expression to a structural gene for an indicator protein, such as chloramphenicol acetyltransferase, luciferase or β-galactosidase.

In a further aspect of the present invention, there is provided a method to identify compounds which are agonists or antagonists of mammalian calcium channels whereby an eukaryotic cell with an heterologous calcium channel, prepared as described above, is contacted with the compound to be tested, and the effect of the compound to be tested on the calcium concentration in the cell is then measured, either directly or indirectly.

These cells of the invention, which have functional, foreign calcium channels (i.e., functional calcium channels wherein at least one of the calcium channel subunits is not native to the cell) will be useful for, among other purposes, assaying a compound for calcium channel agonist or antagonist activity. First, such a cell can be employed to measure the affinity of such a compound for the functional calcium channel. Secondly, such a cell can be employed to measure electrophysiologically the calcium channel activity in the presence of the compound being tested as well as an ion or molecule, such as $Ca^{++}$ or $Ba^{++}$, which is known to be capable of entering the cell through the functional channel. For similar studies which have been carried out with the acetylcholine receptor, see Claudio et al. *Science* 238 1688–1694 (1987). These methods for assaying a compound for calcium channel agonist or antagonist activity are also part of the present invention.

In a still further embodiment of the present invention, there is provided a method for the production of functional, foreign calcium channels by expressing the cDNA-containing cells as described above.

Such cells according to the invention, in the preferred embodiment, wherein the cell also contains an heterologous gene with a transcriptional control element, which is active in the cell and responsive, either directly or indirectly, to an ion or molecule capable of entering the cell through a functional calcium channel and is linked operatively for expression to a structural gene for an indicator protein, can also be employed, in another method according to the invention for assaying a compound for calcium channel agonist or antagonist activity. This method comprises exposing a culture of such cells to a solution of a compound being tested for such activity, together with an ion or molecule which is capable of entering the cells through a functional calcium channel and affecting, either directly or indirectly, the activity of the transcriptional control element controlling transcription of the gene for the indicator protein, and comparing the level of expression, in the cells of the culture, of the gene for the indicator protein with the level of such expression in the cells of another, control culture of such cells.

A "control culture," as clearly understood by those of skill in the art, will be a culture that is, and is treated, substantially the same as the culture exposed to the compound being assayed, except that the control culture is not exposed to the compound being assayed. Alternatively, a control culture will be a culture that is exposed to the compound being assayed, but has not been transformed with calcium channel subunit encoding sequences, but is otherwise treated substantially the same as the test culture. Levels of expression of the genes for the indicator proteins are ascertained readily by the skilled by known methods, which involve measurements of the concentration of indicator protein via assays for detectable compounds produced in reactions catalyzed by the indicator protein.

As indicated above, indicator proteins are enzymes which are active in the cells of the invention and catalyze production of readily detectable compounds, e.g., chromogens, fluorescent compounds, radioactively labeled compounds, and the like.

The invention entails also a labeled (e.g., $^{32}P$ or a biotinylated) RNA or single-stranded DNA of at least 14 (preferably at least 30) bases in length in a sequence which comprises a sequence of at least 14 (preferably at least 30) contiguous bases between bases 1 and 1171, inclusive, in Sequence ID NO. 1, which encodes rabbit skeletal muscle γ-subunit. The use of such DNAs and RNAs as probes, to identify and isolate cDNAs coding calcium channel γ-subunits or to identify tissue in which γ-subunit mRNA is made, is clear to those skilled in the art. In this regard, see, e.g., Example 4.

The primary strategy for cloning cDNAs encoding the γ polypeptide subunit of the DHP-sensitive calcium channel from rabbit skeletal muscle was to screen rabbit back skeletal muscle cDNA expression libraries with an antibody probe specific to the protein. See generally Ausubel et al., *Current Protocols in Molecular Biology*, Wiley-Interscience, New York (1987); Davis et al., *Basic Methods in Molecular Biology*, Elsevier Science Publishing Co., New York (1986).

Polyclonal antisera for the γ polypeptide subunit were prepared in guinea pigs as described by Sharp and Campbell, *J. Biol. Chem.* 264, 2816–2825 (1989). The γ-specific polyclonal antisera were used for screening of approximately $1.0 \times 10^6$ plaques of recombinant phages of a random-primed lambda gt11 cDNA library.

In an initial screen with the guinea pig γ-specific polyclonal antisera, two cDNA clones were isolated and identified as J6 and J10. These clones were shown to be related to each other by partial sequencing and restriction digestion analysis. These cDNAs were used to screen an oligo dT-primed lambda gt11 cDNA library to isolate overlapping cDNA clones. Three clones were isolated from this screen, and were identified as G2, G10 and G11. One of these clones (G10) was partially sequenced. The insert from clone G10 was then oriented with respect to the inserts from clones J6 and J10. The cDNA insert from clone J10 was then used to screen pooled recombinants from a rabbit skeletal muscle cDNA library [MacLennan et al, *Nature* 316, 696 (1985)] constructed according to Okayama and Berg [*Mol. Cell Biol.* 3, 280–289 (1983)]. Of the positive clones identified from this screening, clone G4-3 was found to encompass and extend the cDNA inserts in clones J6, J10 and G10.

The cDNA clones were then analyzed to establish the coding DNA sequence of the γ-subunit of the calcium channel. Approximately 1171 nucleotides of γ-subunit cDNA was cloned, which is consistent with an estimated 1200 nucleotide γ-subunit mRNA.

Sequence ID NO. 1 represents the 1,171 nucleotides of the cDNA sequence encoding the γ-subunit and its precursor, including 48 nucleotides of 5' untranslated sequence, a 666 nucleotide open reading frame, and 457 nucleotides of 3' untranslated sequence.

The 1171-nucleotide cDNA sequence set forth in Sequence ID NO. 1 contains a 666-nt open reading frame coding for 222 amino acids. The deduced amino acid sequence yields a calculated molecular weight of 25,058 Dalton, which is in approximate agreement to the observed molecular mass of 32 kD for the glycosylated (1–3) and 20 kD for the chemically de-glycosylated forms of the γ-subunit, as determined by SDS-polyacrylamide gel electrophoresis. The deduced amino acid sequence is also in agreement with the authentic $NH_2$-terminus of the γ-subunit as determined by protein sequence analysis on the purified skeletal muscle protein (see Example 5).

The present invention makes available well-characterized cDNA clones encoding each of the four subunits of the rabbit skeletal muscle DHP-sensitive $Ca^{2+}$ channel. It is, therefore, now possible to incorporate various combinations of these, cDNAs into recombinant DNA expression systems to make functional calcium channels and to assess the relative contribution of each subunit to the formation of functional Ca$^{2+}$ channels.

The present invention will now be described in greater detail by reference to the following non-limiting examples.

EXAMPLE 1

Preparation of β and γ Antibody Probes

The DHP receptor was extracted from heavy microsomes and triads of rabbit skeletal muscle, and then purified, following the procedures described in Sharp, et al. (1987), *J. Biol. Chem.* 262, 12309–12315. Individual components of the receptor were separated by SDS-PAGE on a 5–16% acrylamide gradient gel in the absence (nonreducing condition) or presence (reducing condition) of 1% 2-mercaptoethanol in the sample buffer. The gels were stained for 5–10 min with Coomassie Blue stain in 10% acetic acid, 25% isopropanol, and then destained in distilled water. Individual bands were visualized. The complex contains at least four subunits: α1 (170,000 Da), α2 (175,000 Da non-reduced/150,000 Da reduced), β (52,000 Da) and γ (32,000 Da), which appear to be present roughly in a 1:1:1:1 stoichiometric ratio. The purified complex or individual subunits present in sliced gel bands were then used to immunize experimental animals to induce the production of polyclonal antibodies as described below.

A. β-enriched Antiserum

One sheep, identified as Anti-DHPR#1, was immunized subcutaneously with 500 μg of the purified DHPR protein (not gel separated) in Freund's Complete Adjuvant. Eight weeks post immunization, a subcutaneous boost of 500 μg purified DHPR protein in Freund's Complete Adjuvant was given. A serum sample was collected one week later. A second boost, identical to the first, was given one month after the first bleed, and a second bleed was performed one week after the second boost.

Aliquots of the two bleeds, and aliquots of a pre-immunized serum sample, were characterized for titer and reactivity to the DHPR subunit proteins. Two to five μg of DHPR subunit proteins purified as described above were applied to nitrocellulose, and reacted with 10-fold serial dilutions of the three serum samples. Primary antibody was detected using a peroxidase-labeled secondary antibody and 1-chloro-4-naphthol as a development substrate. The aliquot of serum from the second bleed demonstrated the highest titer of β-specific antisera (>1:1000), and was used in the affinity purification procedure.

B. γ-specific Antiserum

The γ polyclonal serum were prepared in guinea pigs as previously described [Sharp and Campbell, (1989), *J. Biol. Chem.* 264, 2816–2825]. Briefly, guinea pig #16 was immunized at the intervals described in Sharp and Campbell ibid. with a single, homogenized 5 mm×15 mm gel band corresponding to the 32 KD γ subunit (γ content of the gel band was approximately 2 μg). The collected ascites was characterized by Immunoblot analysis as described in (A), above. Samples with titers >1:1000 for the γ subunit were used for further analysis.

C. Affinity Purification

Antibodies raised against the β and γ subunit proteins were affinity purified from serum of injected sheep and guinea pigs, respectively, following the protocol of Sharp and Campbell (1989), *J. Biol. Chem.* 264, 2816–2825, using Immobilon strips. In brief, 200 μg of purified rabbit dihydropyridine receptor were separated by preparative SDS-PAGE and electrophoretically transferred to Immobilon-P membranes (Millipore; resolving gel size =12.5 cm×13 cm). Two vertical strips were cut from the edge of the membrane and stained with the reversible stain Pounceau S to visualize the immobilized protein. The membranes were then separately reacted with 10 ml of a 1:1000 dilution of one of the two polyclonal serum to identify the bands corresponding to the DHP subunits, i.e., one membrane was reacted with anti-β and the other was reacted with anti-γ. Peroxidase-conjugated second antibody was used to colorimetrically detect the cross-reacting bands. The sheep antiserum reacted with the α$_1$ and β subunits; the guinea pig antiserum reacted with the γ subunit only.

Using the stained vertical strip as a guide, horizontal strips corresponding to the β and γ subunit proteins were cut from the immunoblot. To block non-specific binding sites on the nitrocellulose, the strips were incubated with BLOTTO (Bovine Lacto Transfer Technique Optimizer; 50 mM NaH$_2$PO$_4$, 150 mM NaCl, pH 7.4, 5% Nonfat dry milk) for 1 hour at 22° C. The filters were then incubated overnight at 4° C. with 2 ml of either the β or γ polyclonal serum diluted with 8 ml of TBS-BSA (50 mM Tris.HCl 7.4, 150 mM NaCl, 3% BSA). The strips were then washed three times for 15 min each time in 500 mM NaCl, 50 mM Tris.HCl (7.4), followed by three sequential 15 min washes in 100 mM NaCl, 10 mM Tris.HCl (7.4). The bound antibody was eluted with 5 ml of acid (50 mM glycine HCl, pH 2.5) at a temperature of about 22° C. The pH of the eluted antibody wash was neutralized to 7.4 by the addition of 1.0M Tris.HCl, pH 8.0.

The affinity-purified antisera were characterized similarly to the polyclonal sera, and selection for sensitivity and subunit selectivity was done for antibody titer greater than 1:40. The β-specific antisera was called Affi-β, and the γ-specific antisera was called Affi-γ.

EXAMPLE 2

ANTIBODY SCREENING OF A RANDOM-PRIMED RABBIT SKELETAL MUSCLE cDNA LIBRARY AND CLONE CHARACTERIZATION

A. Library Screening

A rabbit skeletal muscle cDNA library was prepared in λgt11, as described by Ellis, et al. (1988), *Science* 241, 1661–1664, using random primers [pd(N)$_6$ hexamers (Pharmacia, Inc., Piscataway, N.J.)] rather than oligo-d(T) to prime single-strand cDNA synthesis. Two sets of duplicate filters of the library, each containing 720,000 plaques, were made and screened for clones containing phage with inserts coding for all or part of the β and γ -subunits of the rabbit skeletal muscle calcium channel. Each filter was screened using either the β- or γ-specific antibody as follows. BLOTTO was used for blocking of the nitrocellulose filters, dilution of the antibodies, and filter washes. Detection involved horseradish peroxidase-linked rabbit anti-sheep secondary antibody and development proceeded using 4-chloro-1-naphthol as a substrate.

The λgt11 library was plated on Y1090 in LB agar and 50 μg/ml ampicillin. A Y1090 culture was grown overnight in 15 ml of LB, 0.2% maltose and 50 μg/ml ampicillin. The cells were pelleted and resuspended in 3 ml of 10 mM MgSO$_4$. Each of six plates was prepared by absorbing ~120,000 phage of the λgt11 cDNA library to 300 μl of the 3 ml cell solution and then pouring onto an LB agar plate in 10 ml soft agar containing 50 µg/ml ampicillin.

The plates were grown at 42° C. for 3.5 hours and then overlayed with IPTG-treated filters which were soaked in 10 mM IPTG (Boehringer Mannheim Biochemicals, Indianapolis, Ind.). The filters were dried until just moist, laid in the plates and incubated for 3.5 hours at 37° C. After the incubation, the filter was oriented, removed, and a second, identical IPTG-treated filter was applied to the agar plate for an additional four hours at 37° C. The orientation of this second filter was identified and marked identically to the first filter.

Two sets of six plates were prepared. One set of filters was used to screen for β-subunit encoding clones and the other set was used to screen for γ-subunit encoding clones. After incubation, one-half microgram of purified DHP receptor was spotted on one filter of each set as a positive control. The filters were washed for 30 min at room temperature with BLOTTO. One set of duplicate filters was then incubated with affinity purified sheep anti-β-subunit polyclonal antibody, and the other set was incubated with affinity purified guinea pig anti-γ-subunit polyclonal antibody. The filters were incubated with their respective antibody overnight in BLOTTO at 4° C. They were then washed three times, for 10 min each time, in BLOTTO.

The filters were then incubated for one hour with BLOTTO containing an appropriate second antibody: HRP-goat anti-sheep IgG (for β); or HRP-goat anti-guinea pig (for γ)|.

The filters were washed as described above for the first antibody, and rinsed with ddH$_2$O to remove BLOTTO.

The positive clones were developed using about 40 ml/plate of 4-chloro-1-naphthol reagent, which is made by dissolving 60 mg of said developer in 20 ml of ice cold MeOH and mixing 4-chloro-1-naphthol (Aldrich Chemical Company, Milwaukee, Wis.) into 100 ml of TBS containing 60 µl of 30% H$_2$O$_2$.

Five positives were identified on both duplicate filters probed with the β antibody and two positives were identified on both filters probed with the γ antibody. Of the five putative β clones originally identified, two were characterized and used further: K5 and K6. Both of the γ clones were characterized: J6 and J10. The four clones were plaque-purified by replating and rescreening with the appropriate antibody using the same conditions as before, until a single, well-isolated plaque was identified for each clone.

B. Characterization of Putative β- and γ-Specific Inserts

The inserts of the putative β and γ clones were characterized by gel sizing, screening with antibody probes, restriction enzyme mapping, and partial sequencing.

1. Gel Sizing

A mini-phage prep was made of each positive clone and the DNA was digested with EcoRI following manufacturer's instructions. The digests were then separated on a 1% agarose gel using the TAE buffer system (Maniatis, 1982), and HindIII digests of control λ DNA as size standards. Bands were visualized using ethidium bromide and u.v. illumination. Based on the results of gel analyses, the approximate size of the inserts were found to be as follows:

| K5 | 500 bp | J6 | 800 bp |
| K6 | 900 bp | J10 | 500 bp |

2. Restriction Enzyme Mapping

To further characterize the inserts of the putative β and γ clones, the inserts were restriction mapped. The EcoRI inserts were subcloned into EcoRI-cut, bovine alkaline phosphatase (BAP)-treated modified pUC19 plasmid. The modified pUC19 plasmid was made by digesting pUC19 with HincII and SmaI and ligating the blunt ends. The resultant plasmid was 17 bp shorter than pUC19 and lacked several restriction sites, i.e., SmaI, XmaI, BamHI, XbaI, HincII, AccI, and SalI. Ten micrograms of the ligation reaction were used to transform DH5α cells. AmpR colonies were selected. Plasmid preps were made from the amp$^R$ colonies and aliquots of the DNA were separately digested with selected restriction enzymes. The maps of inserts of the β and γ clones are shown in FIGS. 1 and 2, respectively.

3. Antibody Probes Screen

Plasmid-containing bacteria were grown overnight on ampicillin plates (having a colony density of about 100 colonies per plate). Replicate lifts were made using dry untreated nitrocellulose filters. The replicate lifts were then incubated for 3 hours at 37° C. on filter paper wetted with LB Media plus 10 mM IPTG. Incubation was carried out with filters maintained in an inverted position to induce the production of fusion proteins.

Cells were lysed by exposing the filters to chloroform saturated vapors for 5 minutes, followed by overnight incubation at 4° C. in BLOTTO containing 10 mg/ml lysozyme. The filters were then immunoblotted with the appropriate antibodies using the methods described above.

a. β-specific Clones

Both clones tested positive with the affinity-purified antisera Affi-β. Additionally, only clone K5 tested positive with β-specific monoclonal antibody VD21 [Leung, et al, *J. Biol. Chem.* 263, 994–1001 (1988)].

b. γ-specific Clones

Neither of the two γ-specific clones reacted with antisera specific for the $α_1$-, $α_2$-, β-, or δ-specific antisera.

4. Partial Sequencing a. β-specific inserts

A large scale plasmid prep of K5 was prepared, and 2 µg of the DNA per reaction was sequenced according to the procedure provided by United States Biochemical Corporation (Cleveland, Ohio; Sequenase DNA Sequencing Kit). The M13 reverse sequencing primer and the M13 sequencing primer (New England Biolabs, Inc. Beverly, Mass.) were used to prime the sequencing reactions.

Partial sequence of K6 was obtained by isolating two clones comprised of the K6 insert in the modified pUC19 vector in both orientations. The ends of the insert were sequenced using the reverse and forward M13 primers as described for K5. Then, using the SacI site 255 bp from the 5' end of K6 and the HindIII site 444 bp from the 3' end of the insert, in combination with the same restriction sites in the polylinker, deletions in K6 were generated and internal sequence was determined. For each restriction site there are two possible orientations and, thus, two deletions that could be generated. For example, the 255 bp SacI fragment can be released and the remaining DNA religated in order to generate sequence beginning 255 bp in from the 5' end. With the fragment in the opposite orientation, the remaining 684 bp SacI fragment can be released and sequence can then be generated beginning 684 bp in from the 3' end. Each of these deletions was generated (two for the SacI site and two for the HindIII site) and the entire K6 fragment was sequenced.

Analysis of the sequence data revealed a 167 bp overlap between clones K5 and K6, as well as predicted restriction enzyme recognition sites. The K6 insert was predicted to have at least one internal restriction site for the enzymes HindIII, SacI, and PstI. A single open reading frame is encoded by these two overlapping clones. No initiating ATG triplet or translation stop codon was identified. Based on the β-subunit size of 52 kDa and a predicted coding region of at least 1400 bp, the isolated inserts were at least 150 bp short of being complete.

b. γ-specific Insert

The 484 bp EcoRI insert fragment was isolated from a large-scale preparation of J10 and subcloned into pGEM-3 (Promega Corp., Madison, Wis. 53711). pGEM-3 contains both the T7 and SP6 polymerase binding sites positioned on opposite ends of the polylinker sequence. Oligonucleotide primers specific for these polymerase binding sites were purchased from New England Biolabs, Inc. (Beverly, Mass. 01915). The J10 insert sequence was determined by sequencing in from each end of the insert directly out of the plasmid DNA. The Sequenase Kit was used as described above. Overlapping sequence at the center of the insert was observed, thus, the sequence of the entire insert was complete.

The J6 insert contains an internal EcoRI restriction site that divides the insert into two fragments, a ~740 bp fragment and a ~230 bp fragment. Initially, the larger, 740 bp fragment was subcloned into the modified pUC19 vector. The ends of the insert were sequenced using the universal and reverse primers described above, and J6 was positioned relative to J10 based on the determined sequence.

Oligonucleotide primers were synthesized based on the terminal sequences of J10. Internal J6 sequence was determined using the γ-specific oligonucleotide primer based on the 5' end of J10. This determined sequence combined with the J10 sequence, completed the sequencing of the 740 bp J6 fragment and provided 819 nts of continuous sequence.

To characterize the remaining sequence, the ~230 bp J6 EcoRI fragment was subcloned into pGEM-3 and sequenced.

EXAMPLE 3

SCREENING OF OLIGO dT-PRIMED RABBIT SKELETAL MUSCLE cDNA LIBRARY AND CLONE CHARACTERIZATION

A. Screening

In an attempt to isolate inserts encoding the full length β- and γ-specific cDNA, or at least to isolate inserts encoding β- and γ-specific cDNA sequences that could be spliced to inserts from clones K5 and K6, and J6 and J10 to construct full length β- and γ-specific cDNAs, respectively, the inserts from clones K5 and K6, and J6 and J10 were used to screen two pairs of duplicate lifts of an oligo dT-primed rabbit skeletal muscle λgt11 cDNA library (Ellis, et al., Supra) under non-stringent conditions. Hybridization: 20% formamide, 5X Denhardts, 6X SSPE, 0.2% SDS, at 42° C. Wash: 0.2X SSPE, 0.2% SDS, 45° C.

Screening with the β inserts yielded four positives on duplicate filters. The γ insert screening yielded three positives on duplicate filters. The seven clones were plaque-purified and remained positive in subsequent screenings.

B. Characterization

The inserts from the positive clones were removed by EcoRI digestion as described previously and sized. The clone names and insert sizes are as follows:

| βB | 1800 | G2  | 2300 |
|----|------|-----|------|
| βC | 1500 | G11 | 2000 |
| βD | 1500 | G10 | 650  |
| βE | 2100 |     |      |

The inserts listed above were subcloned into pUC19, modified as before, and restriction mapped and partially sequenced. The restriction maps allowed the various β and γ clones to be oriented [as shown in FIGS. 2 and 3].

The DNA sequence of insert βD was determined directly out of the plasmid using the M13 primers as described previously. Insert βD is 1293bp. It extends 218 nts 5' of K5 and ends 176 nts short of the 3' end of K6 (See FIG. 2).

The sequence of the βE insert at the 3' end was determined by sequencing the plasmid DNA priming with the universal primer (sequencing through the polyA tail) and priming internal sequence using an oligo synthesized based on the 3' end of K6. Overlapping sequence was determined, thus completing a continuous 1769 nt sequence from the 5' end of βD to the 3' end of βE.

The sequence at the 3' end of βB was determined as described above. The sequence primed with the internal oligo matches the sequence determined for βE. Sequence adjacent to the polyA tail was obscured and not determined. Even though individual nucleotides cannot be determined in this sequencing reaction, one can see from the general pattern that the sequence matches the sequence determined for βE.

Sequence ID NO. 2 shows the complete DNA sequence and deduced amino acid sequence of the cloned β-subunit transcript. This sequence is a compilation of the DNA sequence determined by us and that reported by Ruth et al., Science 245, 1115 (1989). Ambiguities in the sequence determined by us were resolved by comparison of the sequence to that reported by Ruth et al. The amino acid residue through these regions are shown circled.

The termini of clone G10 were sequenced as described above and G10 was positioned relative to J6 and J10. A polyA tail was identified at the 3' end. Overlapping sequence was completed by priming G10 sequence internally using an oligonucleotide primer based on the 3' end of J10. The combined, determined sequence of J10, J6, and G10 was 1139 nt.

EXAMPLE 4

SCREENING OF OKAYAMA-BERG RABBIT SKELETAL MUSCLE cDNA LIBRARY FOR γ-SUBUNIT INSERTS AND CLONE CHARACTERIZATION

A rabbit skeletal muscle cDNA library (MacLennan et al., 1985, Nature 316, 696) constructed according to Okayama and Berg was screened for γ clones. Approximately 2×10⁶ recombinants were transformed into *E. coli* by standard methods. The transformation mix was divided into ten aliquots and each was separately inoculated into 100 mls of broth media. The transformed *E. coli* were grown to stationary phase and the plasmid DNA in each of the ten cultures was recovered by a standard plasmid prep procedure that was scaled down to 100 mls. Digestion of the pools with BamHI or XhoI released the insert from the Okayama-Berg vector pcD-X. The digest was probed with the J10 insert fragment. A series of fragments, the largest and most abundant fragment being ~1.5 kb for XhoI and ~1.4 Kb for BamHI were identified. These insert sizes are consistent with an ~1200 nt transcript (see below) after additional sequence contributed by the Okayama-Berg vector, ~250 nt for XhoI and ~150 nt for BamHI, is subtracted. These fragments were present in both pool 8 and pool 10.

An aliquot of pool 8 was transformed into *E. coli* and ~600,000 recombinants were probed with the J10 fragment. Approximately ~50 to 75 duplicate positives were identified. Nine were chosen for further characterization. The insert size was identified in two clones: G4-3 and G6-1, ~1275 nts and ~1075 nts, respectively. The internal EcoRI site was mapped in each clone. G4-3 extends ~475 nt 5' of the EcoRI site and 6-1 extends ~275 nts 5' of the site. Further characterization of G4-3 by subcloning into M13 and DNA sequencing showed that G4-3 encoded the complete γ-subunit coding sequence in addition to 48 nt of 5' untranslated sequence and 457 nt of 3' untranslated sequence. The γ-subunit cDNA sequence and the determined amino acid sequence are shown in Sequence ID NO. 1.

EXAMPLE 5

SEQUENCE OF THE γ PROTEIN ISOLATED FROM RABBIT SKELETAL MUSCLE TISSUE

The γ-subunit protein was electrophoresed and blotted onto immobilon by the method of Matsudaira [J. Biol. Chem. 262, 10035–10038 (1987)]. The portion of the blot that contained the γ-subunit was excised from the immobilon membrane and analyzed for protein sequence. The stained immobilon pieces were placed into a sequencing reaction chamber above a biobrene-treated glass fiber filter. The Applied Biosystems 470 Gas Phase Protein Sequencer, with online phenylthiohydantoin analyzer, was run as described previously [Hunkapillar, M. W. and Hood, L. E. (1983), Science 219, 650; Hewick, R. M. et al., *J. Biol. Chem.* 256, 7990 (1981)], and the following sequence was determined:

```
1           5           9
M—S—P—T—E—A—P—K—V
```

The raw data for this sequencing analysis is presented in FIG. 5A–5J.

EXAMPLE 6

DEVELOPMENT OF CALCIUM CHANNEL SUBUNIT-EXPRESSING MAMMALIAN CELLS

A. Transient Transfection Protocol

The host cells transfected with calcium channel subunit-encoding DNAs, transfection selection plasmids, and marker construct plasmid were developed using the following protocol.

Approximately 24 hr prior to transfection, host cells are plated in 10 cm plates at a density of 2.5×10⁶ cells/plate and incubated at 37° C. (5% $CO_2$). One to eight hours prior to transfection, the cells are fed 9 ml of media [500 ml Dulbecco's Modified Eagle Medium; 4500 mg/L D-glucose; L-glutamine; 55 ml calf serum; 5 ml penicillin/streptomycin (100X: 10,000 U/ml/10,000 µg/ml) ].

The DNAs are prepared by combining 5 µg of each subunit-encoding expression plasmid to be transfected with water to a final volume of 440 µl. The water-DNA solution is mixed, and 60 µl of 2M $CaCl_2$ is added and mixed. This is called Solution B. Solution A is 500 µl of 2X HBS (2X=10 g/L Hepes, 16 g/L NaCl; autoclaved; pH=7.10±0.05) mixed with 10 µl of 100X $PO_4$ (1:1 mixture of 70 mM $Na_2HPO_4$ and 70 mM $NaH_2PO_4$. A DNA precipitate is made by dripping Solution B into Solution A, while bubbling sterile air through Solution A for mixing. The precipitate is allowed to form during the next 30±10 min.

The plated cells were transfected by adding, dropwise, ~1 ml of precipitate to each plate containing cells and media and mixing well by swirling. The treated cells were returned to the incubator (37° C.; 5% $CO_2$) for five hr.

A glycerol shock is then applied to the transfected cells by removing the DNA precipitate and media and adding 2 ml of media containing 10% glycerol. After three minutes, the glycerol media is diluted with 5 ml PBS and mixed. The PBS-diluted media is aspirated off and the 5 ml PBS wash is repeated two more times. After the third PBS wash is aspirated off, the cells are fed 9 ml media and incubated at 37° C. (5% $CO_2$) for 24 to 72 hr.

The transfected cells can be analyzed 24–72 hours after DNA addition. Analysis can include 1) selection of transfectants, 2) northern analysis, 3) western analysis, 4) ligand binding studies, 5) functional analysis using a marker construct, and 6) electrophysiological measurements.

B. Mammalian Host Cells

The preferred cells for use as host for transfection with DNAs of the invention are Ltk-cells (ATCC CCL1.3).

C. Eukaryotic Expression Vectors Encoding Calcium Channel Subunit-Encoding DNAs

The calcium channel subunit expression plasmids were constructed using the following parent plasmids: (1) modified pSV2dhfr [Subramani et al., (1981) *Mol. Cell. Biol.* 1:854–864; modified by cutting at the unique HindIII site and inserting a 5'—EcoRI—EcoRV—HindIII—3' polylinker], (2) pSV2 (plasmid pSV2dhfr was digested with HindIII and BglII, releasing the dhfr sequence, which was then replaced with a 5'—HindIII—EcoRV—EcoRI—BglII—3' adapter), and (3) pcD-X [Okayama, H. and Berg, P. (1983) *Mol. Cell. Biol.* 3:280–289].

Figure 6:
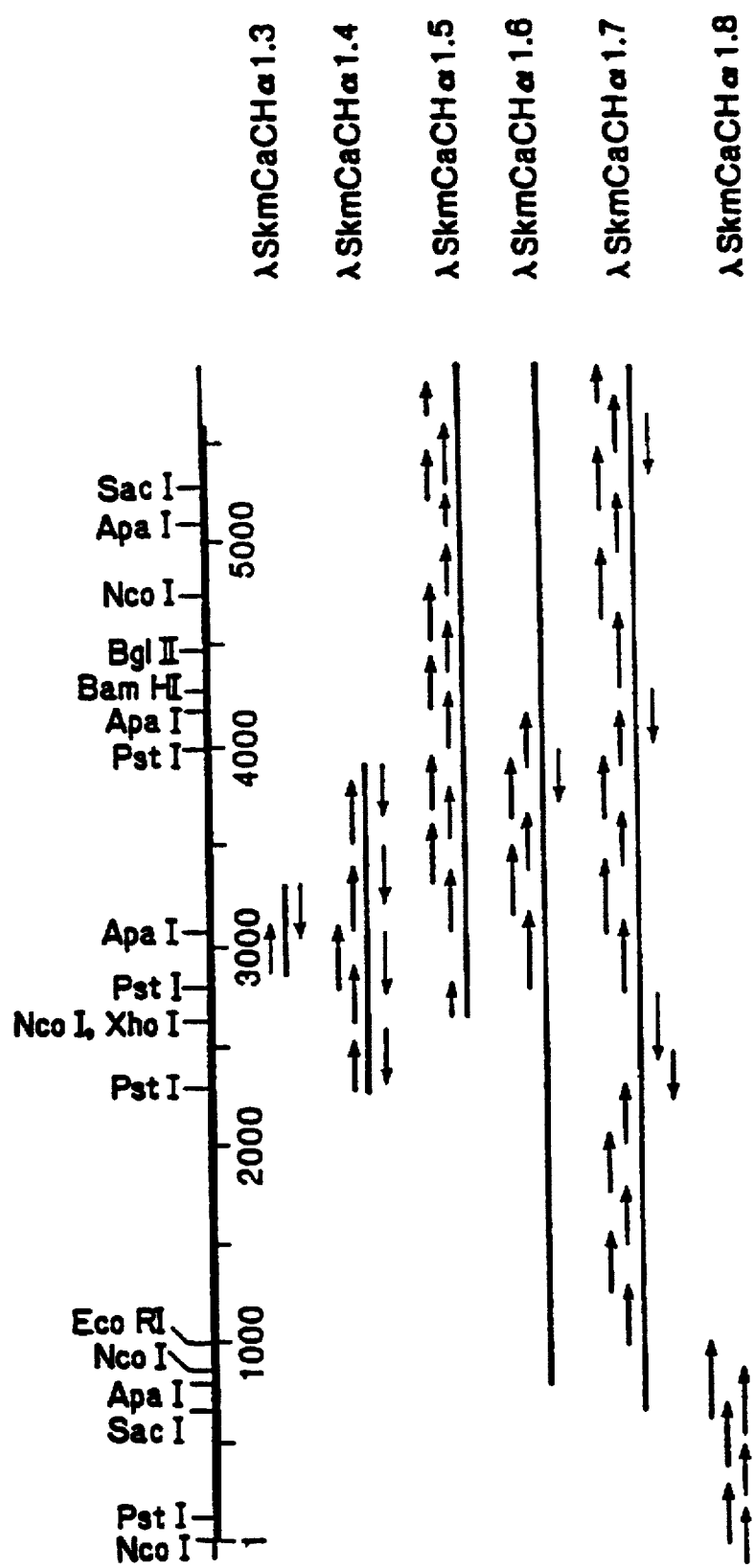
FIG. 6 is a restriction map of a cDNA sequence which encodes the α₁-subunit of a calcium channel, and shows the orientation of various cDNAs encoding the α₁-subunit sequence.
Figure 7:
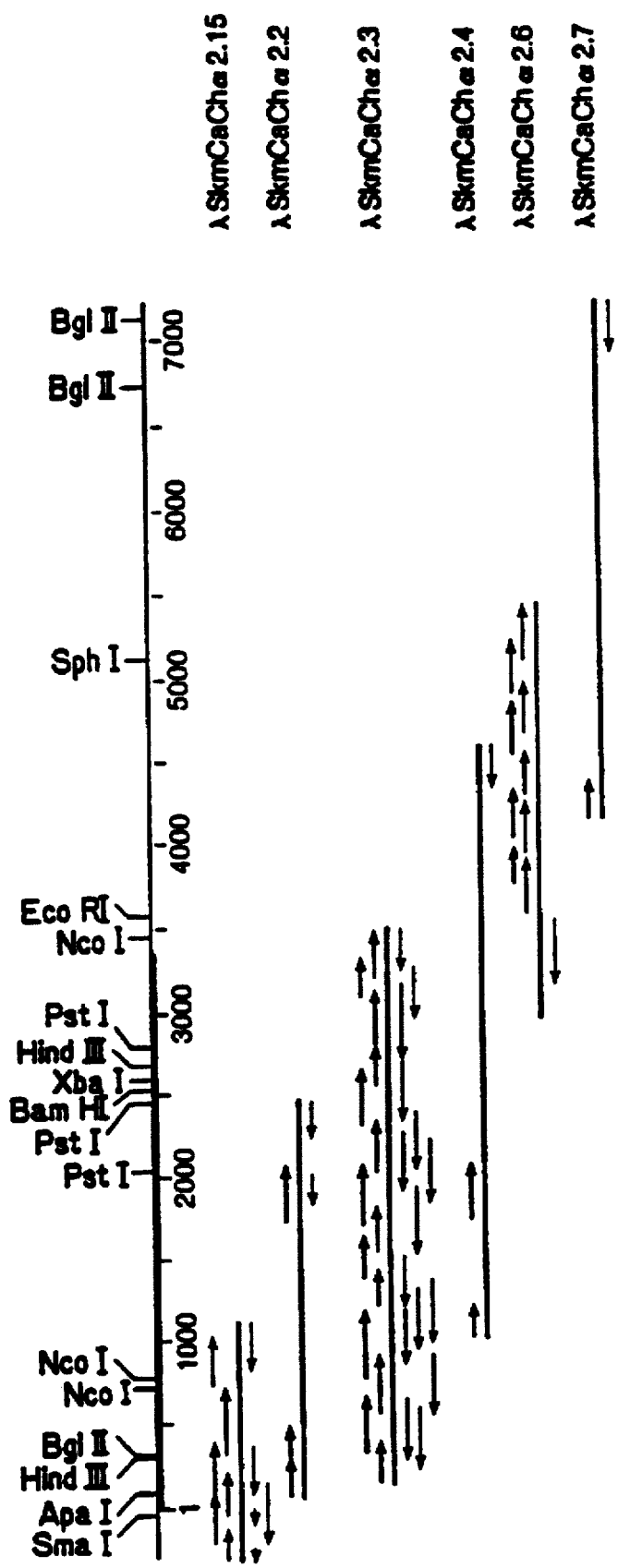
FIG. 7 is a restriction map of a cDNA sequence which encodes the α₂-subunit of a calcium channel, and shows the orientation of various cDNAs encoding the α₂-subunit sequence.

For each expression construct, the insert and vector were ligated at approximately a 2:1 insert-to-vector molar ratio, generally using 50 to 100 ng of vector. Restriction maps of the α1, α2 and β clone inserts, referred to in 1 and 2 below, are shown in FIGS. 6, 7 and 2, respectively.

1. pSKmCaCHα1pSV2dhfr

The 1.55 kb KpnI (polylinker sites) fragment from clone λSKmCaCHα1.8 [Ellis et al., (1988); *Science* 241:

1661–1664)] was inserted into a plasmid vector (e.g., pIBI24, pUC18, pUC19), and the KpnI—EcoRI fragment, encoding nucleotides –78 to 1006 of the α1 subunit, was gel purified.

The 4900 bp EcoRI-BamHI (BamHI site in pcD-X vector) fragment from clone pSKmCaCHα1.7 (Ellis et al., supra) was isolated and gel purified. The BamHI digest was a partial digest to avoid cutting at the internal BamHI site located at ~4300 bp. This fragment was subcloned into EcoRI—BamHI-digested pIBI24 (International Biotechnologies, Inc.; New Haven, Conn.), and the ~4900 nt 3' EcoRI—XbaI (XbaI polylinker site) fragment from that plasmid was gel purified.

The ~1085 nt fragment originating from λSKm-CaCHα1.8 was ligated to the ~4900 nt fragment originating from pSKmCaCHα1.7, and the ligation was cloned into KpnI—XbaI-digested pGEM3 (Promega Corp., Madison, Wis. 53711). An upstream ATG present in the ligated insert, contributed by the EcoRI—KpnI—NcoI adapter used to construct the library from which λSKmCaCHα1.8 was isolated, was removed as follows. The plasmid (pGEM3+ insert) was linearized with KpnI, and the linearized DNA was digested with T4 polymerase in the dCTP; this limits the digestion in both directions to the first C nucleotide. The ends were then made blunt by digestion with S1 nuclease. The linear DNA was ligated to itself and transformed into DH5α cells. The deletion was confirmed by sequencing. This clone was called pSKmCaCHα1.1ΔNcoI.

Modified vector pSV2dhfr was digested with EcoRI and HindIII. A partial EcoRI digest and a HindIII digest of clone pSKmCaChα1.1ΔNcoI was performed, and the ~5950 bp insert encoding the α1 subunit was isolated on a low percentage agarose gel. The vector and insert fragments were ligated together and transformed into DH5α cells. AmpR cells were selected. Correct plasmid was confirmed by restriction mapping and was called pSKmCaCHα1pSV2dhfr. It contains the coding sequence of the α1 subunit of the rabbit skeletal muscle calcium channel, preceded by approximately 78 nucleotides of 5' sequence and followed by the 3' untranslated sequence and a stretch of As.

2. pSKmCaCHα2pSV2

Equal molar amounts of the 650 bp KpnI—HindII fragment from λSKmCaCHα2.15 and the 2700 bp HindIII—XbaI fragment from λSKmCaCHα2.3 (both described in Ellis et al., supra) were ligated together with 50 ng of KpnI—XbaI-digested and dephosphorylated pIBI24. The ligation was transformed into competent NM522 cells (Stratagene, Inc., San Diego, Calif.) and AmpR colonies were selected. The correct clone was identified by restriction mapping and was called pα2.1. Clone pα2.1 was digested with XbaI and SphI (SphI site in vector) and dephosphorylated. A second three-way ligation was performed with the XbaI—SphI fragment from pα2.1 and the 750 bp XbaI—NcoI fragment from λSKmCaCHα2.3 and the 1800 bp NcoI—SphI fragment from λSKmCaCHα2.6. The ligation was transformed into NM522 cells and AmpR colonies were selected. Correct plasmid was identified by restriction digest mapping and was called pα2.15.

Vector pSV2 was digested with EcoRI and EcoRV and ligated to the ~3600 bp gel purified, SmaI—EcoRI fragment from pα2.15. The ligation was transformed into DH5α cells. AmpR cells were selected. Correct plasmid was identified by restriction digestion, and was called pSKmCaCHα2pSV2. It contains the coding sequence of the α2 subunit of the rabbit skeletal muscle calcium channel, preceded by approximately 56 nucleotides of 5' sequence and followed by ~300 nt of 3' untranslated sequence.

3. pSKmCaCHβpSV2

A full-length construct of the β-encoding sequence was made by ligating the 975 bp EcoRI—HindII fragment (5' end of β) from pβD (gel-purified) and the 775 bp HindIII—EcoRI fragment (3' end of β) from pβB (gel purified) together. The ligation was then digested with EcoRI and the 1700 bp EcoRI fragment was gel purified and ligated into EcoRI-digested and dephosphorylated pGEM3Z. The ligation was transformed into DH5α cells, and restriction mapping was performed to identify the correct clone. The 1700 bp insert of the correct clone was released by EcoRI digestion, gel purified, and ligated into EcoRI-digested and dephosphorylated vector pSV2. The ligation was transformed into DH5α cells. AmpR cells were selected. Correct plasmid was identified by restriction mapping and was called pSKmCaCHβpSV2. It contains the coding sequence of the β subunit of the rabbit skeletal muscle calcium channel, preceded by approximately 92 nucleotides of 5' sequence and followed by 3' untranslated sequence and a stretch of As.

4. pSKmCaCHγpcD-X

Clone G4-3, isolated from the Okayama-Berg library (see Example 4), was renamed pSKmCaCHγpcD-X. It contains the coding sequence of the γ subunit of the rabbit skeletal muscle calcium channel, preceded by approximately 48 nucleotides of 5' sequence and followed by 3' untranslated sequence and a stretch of As. The insert is contained in the pcD-X expression vector.

D. Development of Cell Line Containing Four Calcium Channel Subunit DNAs

Cells were developed to express all four subunits of a calcium channel by transfecting Ltk-cells with 5 μg each of plasmids pSKmCaCHα1pSV2dhfr (α1), pSKmCaCHα2pSV2 (α2), pSKmCaCHβpSV2 (γ), pDKmCaCHγpcD-X (β), and 1 μg of the selection plasmid pThx24 [Zipser et al. (1981); Proc. Natl. Acad. Sci. 78:6276–6280], following the protocol of (A). Positive transfectants were selected in HAT media (media in "A", plus 15 μg/ml hypoxanthine, 1 μg/ml aminopterin, 5 μg/ml thymidine) following standard procedures.

While the present invention has been described in detail herein, those of ordinary skill in the art will recognize numerous variations and modifications, in what is described, that are within the spirit of the invention. Such variations and modifications are within the scope of the invention as described and claimed herein.

That which is claimed is:

1. An isolated nonchromosomal DNA molecule comprising a sequence of nucleotides encoding a naturally-occurring γ-subunit of a mammalian calcium channel, wherein a DNA molecule having said sequence hybridizes under non-stringent conditions to the complement of a DNA molecule encoding the protein having the sequence of amino acids set forth in SEQ ID NO: 5, wherein:

non-stringent conditions are those that result in hybrids that form in 20% formamide, 6X SSPE at 42° C. and remain when washed with 0.2X SSPE at 45° C.; and the isolated DNA molecule is fully complementary to an mRNA transcript native to a mammalian cell.

2. The DNA molecule of claim 1, wherein the γ-subunit is a skeletal muscle calcium channel.

3. A eukaryotic cell, comprising the DNA molecule of claim 2 wherein the DNA molecule is heterologous to the cell.

4. A eukaryotic cell, comprising the DNA molecule of claim 1, wherein the DNA molecule is heterologous to the cell.

5. A method for the production of the γ-subunit of a mammalian calcium channel, comprising the step of causing the eukaryotic cell of claim 4 to express the heterologous DNA, whereby a γ-subunit is produced.

6. An isolated DNA molecule of claim 1, comprising a sequence of nucleotides that hybridizes under non-stringent conditions to the DNA set forth in Sequence ID No. 1.

7. The nucleic acid molecule of claim 1 that is mRNA.

8. Isolated RNA encoded by the DNA molecule of claim 1.

9. A eukaryotic cell with a heterologous calcium channel, wherein:

the calcium channel comprises a γ-subunit encoded by a DNA molecule of claim 1; and the only heterologous ion channels are calcium channels.

10. A method for preparing a cell expressing a heterologous calcium channel, comprising the steps of:

providing a eukaryotic cell capable of expressing a mammalian calcium channel;

transforming the cell with a DNA molecule of claim 1; and causing the cell to express the DNA, whereby a calcium channel that contains a heterologous γ-subunit is expressed.

11. The method of claim 10, wherein the cell is selected from the group consisting of a yeast cell and a mammalian cell.

12. The method of claim 11, wherein the γ-subunit is a neuronal calcium channel subunit.

13. The method of claim 10, wherein the γ-subunit is a skeletal muscle, cardiac or neuronal calcium channel subunit.

14. The method of claim 10, wherein the γ-subunit comprises the sequence of amino acids set forth in Sequence ID No. 5.

15. An isolated nonchromosomal nucleic acid molecule comprising a sequence of nucleotides or ribonucleotides that encodes a naturally-occurring γ-subunit of a mammalian voltage-dependent calcium channel.

16. A eukaryotic cell comprising the nucleic acid molecule of claim 15, wherein the nucleic acid molecule is heterologous to the cell.

17. The nucleic acid molecule of claim 15 that is DNA.

18. An isolated eukaryotic cell comprising the nucleic acid molecule of claim 15.

19. An isolated single-stranded nucleic acid molecule comprising (a) at least 14 contiguous bases between bases 1 and 1171 as set forth in SEQ ID NO: 1, or (b) the complement of a sequence of at least 14 contiguous bases between bases 1 and 1171 as set forth in SEQ ID NO: 1, with the proviso that if the molecule is RNA, then the thymidine bases in SEQ ID NO: 1 are replaced with uracil bases;

wherein the nucleic acid molecule is capable of hybridizing under non-stringent conditions to a DNA molecule encoding a naturally occurring mammalian calcium channel γ-subunit protein, wherein non-stringent conditions are those that result in hybrids that form in 20% formamide, 6X SSPE at 42° C. and remain when washed with 0.2X SSPE at 45° C.

20. The labeled RNA or DNA molecule of claim 19, wherein the label is $^{32}$P.

21. An RNA or DNA molecule of claim 19, comprising 30 contiguous bases between bases 1 and 1171 set forth in Sequence ID No. 1, or the complement of 30 contiguous bases between bases 1 and 1171 set forth in Sequence ID No. 1.

22. The labeled RNA or DNA molecule of claim 21, wherein the label is $^{32}$P.

23. A method for the identification of DNA molecules that encode the γ-subunit protein of a naturally-occurring mammalian calcium channel, comprising:

screening a library of mammalian nucleic acid molecules with a single-stranded nucleic acid molecule of claim 19, wherein:

screening is effected by hybridizing the molecule under non-stringent conditions;

non-stringent conditions are those that result in hybrids that form in 20% formamide, 6X SSPE at 42° C. and remain when washed with 0.2X SSPE at 45° C.; and identifying DNA molecules in the library that hybridize to the single-stranded nucleic acid molecule.

24. A eukaryotic cell comprising a heterologous calcium channel, wherein said cell is made by a process comprising (1) administering to a suitable cell:

a first composition comprising a first RNA or cDNA molecule which is translatable in said cell into the γ-subunit of a calcium channel native to a first mammalian species, and a second composition comprising a second RNA or cDNA molecule which is translatable in said cell into the $\alpha_1$-subunit of a calcium channel native to a second mammalian species, a third RNA or cDNA which is translatable in said cell into the $\alpha_2$-subunit of a calcium channel native to a third mammalian species, and a fourth RNA or cDNA which is translatable in said cell into the $\beta$-subunit of a calcium channel native to a fourth mammalian species, wherein the $\delta$-subunit-encoding first RNA or cDNA molecule comprises the sequence of a nucleic acid molecule that:

(a) encodes a $\gamma$-subunit of a mammalian calcium channel and hybridizes under non-stringent conditions to the complement of a DNA molecule encoding the amino acid sequence set forth in SEQ ID NO: 5, (b) encodes a $\gamma$-subunit of a mammalian calcium channel and hybridizes under non-stringent conditions to the complement of a DNA molecule having the nucleotide sequence set forth in SEQ ID NO: 1, or (c) a nucleic acid molecule degenerate with the molecule of (a) or (b);

non-stringent conditions are those that result in hybrids that form in 20% formamide, 6X SSPE at 42° C. and remain when washed with 0.2X SSPE at 45° C; and (2) culturing the cell under conditions which cause said RNA or cDNA molecules to be transcribed, wherein the only heterologous ion channels are calcium channels.

25. A cell of claim 24, wherein said cell is an amphibian oöcyte, and the compositions are administered by microinjection.

26. A cell of claim 25, wherein said cell is a *Xenopus laevis* oöcyte.

27. A cell of claim 24, wherein the $\alpha_2$-subunit is a skeletal muscle, cardiac or neuronal calcium channel subunit and the $\gamma$-subunit is of a skeletal muscle, cardiac or neuronal calcium channel subunit.

28. A cell of claim 27 wherein the $\gamma$-subunit is a human calcium channel subunit.

29. A cell of claim 27, wherein the $\gamma$-subunit is a neuronal or skeletal muscle calcium channel subunit.

30. A cell of claim 27, wherein the RNA or cDNA molecule of the first composition encodes a protein comprising the sequence of amino acids set forth in Sequence ID No. 5, and the RNA or cDNA molecule of the second composition encodes a protein comprising the sequence of amino acids set forth in Sequence ID No. 8.

31. A eukaryotic cell comprising a naturally-occurring $\gamma$-subunit of a calcium channel, wherein:

the cell is made by a process comprising administering to the cell a composition comprising RNA or cDNA that encodes the $\gamma$-subunit of a naturally-occurring mammalian voltage-dependent calcium channel and causing the RNA or cDNA to be expressed;

the only heterologous ion channels in the cell expressing the RNA or cDNA are calcium channels; and the $\gamma$-subunit is heterologous to the cell.

32. A cell of claim 31, wherein:

the cell is an amphibian oöcyte; and the composition is administered by microinjection.

33. A cell of claim 32, wherein the cell is an oöcyte of *Xenopus laevis*.

34. A cell of claim 31, wherein the $\gamma$-subunit is a skeletal muscle, cardiac or neuronal calcium channel subunit.

35. A cell of claim 34, wherein $\gamma$-subunit is a human calcium channel $\gamma$-subunit.

36. A cell of claim 35, wherein the $\gamma$-subunit is a neuronal calcium channel subunit.

37. A method for the production of a eukaryotic cell that comprises a heterologous calcium channel, comprising the steps of:

administering to a eukaryotic cell capable of expressing a mammalian calcium channel a first composition comprising a first RNA or cDNA molecule which is translatable in said cell into a mammalian calcium channel $\gamma$-subunit and a second composition comprising an RNA or cDNA molecule which is translatable in said cell into the $\alpha_2$-subunit of a mammalian calcium channel native to a second mammalian species, and thereafter causing the cell to express the RNA or cDNA molecules, wherein the $\gamma$-subunit-encoding first RNA or cDNA molecule comprises the sequence of a nucleic acid molecule that:

(a) encodes a $\gamma$-subunit of a mammalian calcium channel and hybridizes under non-stringent conditions to the complement of a DNA molecule encoding the amino acid sequence set forth in Sequence ID No. 5, (b) encodes a $\gamma$-subunit of a mammalian calcium channel and hybridizes under non-stringent conditions to the complement of a DNA molecule having the nucleotide sequence set forth in Sequence ID No. 1, or (c) a nucleic acid molecule degenerate with the molecule of (a) or (b); and non-stringent conditions are those that result in hybrids that form in 20% formamide, 6X SSPE at 42° C. and remain when washed with 0.2X SSPE at 45° C.

38. The method of claim 37, wherein the cell is an amphibian oöcyte, and wherein, in the process of making the cell, the compositions are administered to the cell by microinjection.

39. The method of claim 38, wherein the cell is an oöcyte of *Xenopus laevis*.

40. A method of claim 37, wherein: the $\alpha_2$-subunit is a skeletal muscle, cardiac or neuronal calcium channel subunit and the $\gamma$-subunit is a skeletal muscle, cardiac or neuronal calcium channel subunit.

41. The method of claim 40, wherein the subunits are rabbit or human calcium channel subunits.

42. The method of claim 41, wherein the $\gamma$-subunit is a neuronal or skeletal muscle calcium channel subunit.

43. The method of claim 40, wherein the first composition comprises a molecule having a sequence of ribonucleotides that encodes a peptide with the amino acid sequence set forth in Sequence ID No. 5, and the second composition comprises a molecule having a sequence of ribonucleotides that encodes a protein having the amino acid sequence set forth in Sequence ID No. 8.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1171 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( i x ) FEATURE:
        ( A ) NAME/KEY: CDS
        ( B ) LOCATION: 49..717
        ( D ) OTHER INFORMATION: /product="Gamma subunit of animal calcium channel"

( x i ) SEQUENCE DESCRIPTION: SEQ ID NO:1:

```
GCGCCGCCGC CAGACCCTAC CTGGAGCACC CACCCTCTG CAGCCGCC ATG TCC CCG                57
                                                      Met Ser Pro
                                                        1

ACG GAA GCC CCA AAG GTC CGC GTG ACC CTC TTC TGC ATC CTG GTG GGC               105
Thr Glu Ala Pro Lys Val Arg Val Thr Leu Phe Cys Ile Leu Val Gly
      5              10                  15

ATC GTG CTG GCC ATG ACG GCC GTG GTG AGC GAC CAC TGG GCC GTG CTG               153
Ile Val Leu Ala Met Thr Ala Val Val Ser Asp His Trp Ala Val Leu
 20              25                  30                  35

AGC CCC CAC ATG GAG AAC CAC AAC ACC ACC TGC GAG GCC GCC CAC TTC               201
Ser Pro His Met Glu Asn His Asn Thr Thr Cys Glu Ala Ala His Phe
                40                  45                  50

GGC CTG TGG CGG ATT TGC ACC AAG CGC ATC GCC CTG GGC GAG GAC AGG               249
Gly Leu Trp Arg Ile Cys Thr Lys Arg Ile Ala Leu Gly Glu Asp Arg
            55                  60                  65

AGC TGC GGA CCC ATC ACC CTG CCT GGG GAG AAG AAC TGC TCC TAC TTC               297
Ser Cys Gly Pro Ile Thr Leu Pro Gly Glu Lys Asn Cys Ser Tyr Phe
        70                  75                  80

CGG CAT TTT AAC CCA GGC GAG AGC TCG GAG ATC TTC GAA TTC ACC ACG               345
Arg His Phe Asn Pro Gly Glu Ser Ser Glu Ile Phe Glu Phe Thr Thr
    85                  90                  95

CAG AAG GAG TAC AGC ATC TCG GCG GCC GCC ATC AGC GTC TTC AGC CTG               393
Gln Lys Glu Tyr Ser Ile Ser Ala Ala Ala Ile Ser Val Phe Ser Leu
100                 105                 110                 115

GGC TTC CTC ATC ATG GGC ACC ATC TGC GCG CTC ATG GCC TTC AGG AAG               441
Gly Phe Leu Ile Met Gly Thr Ile Cys Ala Leu Met Ala Phe Arg Lys
                120                 125                 130

AAG CGG GAT TAC CTG CTG CGG CCG GCG TCC ATG TTC TAC GTC TTT GCA               489
Lys Arg Asp Tyr Leu Leu Arg Pro Ala Ser Met Phe Tyr Val Phe Ala
            135                 140                 145

GGC CTC TGC CTC TTC GTG TCA CTG GAG GTA ATG CGG CAG TCG GTG AAA               537
Gly Leu Cys Leu Phe Val Ser Leu Glu Val Met Arg Gln Ser Val Lys
        150                 155                 160

CGC ATG ATC GAC AGC GAG GAC ACC GTC TGG ATC GAG TAC TAT TAC TCC               585
Arg Met Ile Asp Ser Glu Asp Thr Val Trp Ile Glu Tyr Tyr Tyr Ser
    165                 170                 175

TGG TCC TTT GCC TGC GCC TGC GCC GCC TTC GTC CTC CTC TTC CTC GGG               633
Trp Ser Phe Ala Cys Ala Cys Ala Ala Phe Val Leu Leu Phe Leu Gly
180                 185                 190                 195

GGT ATC TCC CTG CTG CTC TTC TCC CTG CCT CGA ATG CCC CAG AAC CCC               681
Gly Ile Ser Leu Leu Leu Phe Ser Leu Pro Arg Met Pro Gln Asn Pro
```

```
                        200                      205                        210
TGG  GAG  TCC  TGC  ATG  GAC  GCC  GAA  CCC  GAG  CAT  TAG  CCCTCCTGGG              727
Trp  Glu  Ser  Cys  Met  Asp  Ala  Glu  Pro  Glu  His   *
               215                      220

GCGCCCAGGG  AGCCTCGGCC  CAGAACCTTC  CAGAAGGGAG  GCAGGAATTG  CAAACCTGCC              787

CTGTTCCCAT  CTGCCTCACC  CCGCGACTGC  TTCCCTTCCG  TGGCTCTGAC  GGAGCTCCTC              847

TGCTCACAGG  GCAAATGGAC  GCGAGCCCAG  CCCTGTCCTG  GTTGACGAG   GTGGGCAGGT              907

GGTTGGAGGG  GCCCGGCCTT  CCACTGAGGC  TCAAAGCCGT  CCCTGCTGTG  CCGGTTCTCC              967

TTGGGAAGCT  GGGCCCTGGT  AAACCTGGTA  AACCTCCCAG  GAGCACCCCG  TGCGCGCATG             1027

CCGGTGCTGG  GTGCCCCCTG  TGTGAAAAGC  CGGCCCCTCT  GTCTTCCCAG  CCACCAGAAC             1087

CTTCGTTGCC  TCCCGGAGCT  CTGGGAATCA  GCATTTTCCA  CCAGGGAGTA  TCTGACTGTG             1147

GTTTGAAATA  AAAGCGCTCA  GAAC                                                      1171

( 2 ) INFORMATION FOR SEQ ID NO:2:

( i ) SEQUENCE CHARACTERISTICS:
              ( A ) LENGTH: 1772 base pairs
              ( B ) TYPE: nucleic acid
              ( C ) STRANDEDNESS: Not Relevant
              ( D ) TOPOLOGY: Not Relevant ( i i ) MOLECULE TYPE: Genomic DNA ( i x ) FEATURE:
              ( A ) NAME/KEY: Coding Sequence
              ( B ) LOCATION: 93...1667
              ( D ) OTHER INFORMATION: product="Beta subunit of animal calci
                    channel"

( x i ) SEQUENCE DESCRIPTION: SEQ ID NO:2:

GGCTGCGCTG  CGCCGCCCTC  GGCTCCGACG  GGCTTCTCCC  ATGCGCTGAG  GGCGCCGGCG               60

GGGCGTGGCG  GCCGGAGGAG  AGGCTCCCCT  CC  ATG  GTC  CAG  AAG  ACC  AGC  ATG           113
                                        Met  Val  Gln  Lys  Thr  Ser  Met
                                         1                  5

TCC  CGG  GGT  CCT  TAC  CCA  CCC  TCC  CAG  GAG  ATC  CCC  ATG  GAG  GTC  TTC     161
Ser  Arg  Gly  Pro  Tyr  Pro  Pro  Ser  Gln  Glu  Ile  Pro  Met  Glu  Val  Phe
          10                       15                       20

GAC  CCC  AGC  CCG  CAG  GGC  AAA  TAC  AGC  AAG  AGA  AAA  GGG  CGC  TTC  AAA     209
Asp  Pro  Ser  Pro  Gln  Gly  Lys  Tyr  Ser  Lys  Arg  Lys  Gly  Arg  Phe  Lys
 25                       30                       35

CGG  TCC  GAC  GGG  AGC  ACC  TCC  TCA  GAT  ACA  ACA  TCC  AAC  AGC  TTT  GTG     257
Arg  Ser  Asp  Gly  Ser  Thr  Ser  Ser  Asp  Thr  Thr  Ser  Asn  Ser  Phe  Val
 40                       45                       50                       55

CGC  CAG  GGC  TCT  GCC  GAG  TCC  TAC  ACC  AGC  CGT  CCG  TCG  GAC  TCT  GAT     305
Arg  Gln  Gly  Ser  Ala  Glu  Ser  Tyr  Thr  Ser  Arg  Pro  Ser  Asp  Ser  Asp
                60                       65                       70

GTC  TCC  CTG  GAG  GAG  GAC  CGG  GAA  GCC  TTA  AGG  AAG  GAA  GCA  GAG  CGC     353
Val  Ser  Leu  Glu  Glu  Asp  Arg  Glu  Ala  Leu  Arg  Lys  Glu  Ala  Glu  Arg
           75                       80                       85

CAG  GCA  TTA  GCC  CAG  CTT  GAG  AAA  GCC  AAG  ACC  AAG  CCA  GTA  GCA  TTT     401
Gln  Ala  Leu  Ala  Gln  Leu  Glu  Lys  Ala  Lys  Thr  Lys  Pro  Val  Ala  Phe
           90                       95                      100

GCC  GTG  CGG  ACA  AAT  GTC  GGC  TAC  AAT  CCA  TCT  CCA  GGG  GAT  GAG  GTG     449
Ala  Val  Arg  Thr  Asn  Val  Gly  Tyr  Asn  Pro  Ser  Pro  Gly  Asp  Glu  Val
          105                      110                      115

CCT  GTG  GAG  GGA  GTG  GCC  ATC  ACC  TTT  GAG  CCC  AAG  GAC  TTC  CTG  CAC     497
Pro  Val  Glu  Gly  Val  Ala  Ile  Thr  Phe  Glu  Pro  Lys  Asp  Phe  Leu  His
120                      125                      130                      135

ATC  AAG  GAG  AAA  TAC  AAC  AAT  GAC  TGG  TGG  ATT  GGG  CGG  CTG  GTG  AAG     545
```

|     |     |     |     |     |     |     |     |     |     |     |     |     |     |     |      |
|-----|-----|-----|-----|-----|-----|-----|-----|-----|-----|-----|-----|-----|-----|-----|------|
| Ile | Lys | Glu | Lys | Tyr | Asn | Asn | Asp | Trp | Trp | Ile | Gly | Arg | Leu | Val | Lys  |
|     |     |     |     | 140 |     |     |     |     | 145 |     |     |     |     | 150 |      |

| GAG | GGC | TGC | GAG | GTT | GGC | TTC | ATC | CCC | AGC | CCC | GTC | AAA | CTG | GAC | AGC | 593 |
|-----|-----|-----|-----|-----|-----|-----|-----|-----|-----|-----|-----|-----|-----|-----|-----|-----|
| Glu | Gly | Cys | Glu | Val | Gly | Phe | Ile | Pro | Ser | Pro | Val | Lys | Leu | Asp | Ser |     |
|     |     | 155 |     |     |     |     | 160 |     |     |     |     | 165 |     |     |     |     |

| CTG | CGC | CTG | CTG | CAG | GAA | CAG | AAG | CTG | CTG | CAG | AGC | CGC | CTC | AGC | TCC | 641 |
|-----|-----|-----|-----|-----|-----|-----|-----|-----|-----|-----|-----|-----|-----|-----|-----|-----|
| Leu | Arg | Leu | Leu | Gln | Glu | Gln | Lys | Leu | Leu | Gln | Ser | Arg | Leu | Ser | Ser |     |
|     |     | 170 |     |     |     |     | 175 |     |     |     |     | 180 |     |     |     |     |

| AGC | AAA | TCA | GGC | GAC | AAC | TCC | AGC | TCC | AGT | CTG | GGT | GAC | GTA | GTG | ACT | 689 |
|-----|-----|-----|-----|-----|-----|-----|-----|-----|-----|-----|-----|-----|-----|-----|-----|-----|
| Ser | Lys | Ser | Gly | Asp | Asn | Ser | Ser | Ser | Ser | Leu | Gly | Asp | Val | Val | Thr |     |
|     | 185 |     |     |     |     | 190 |     |     |     |     | 195 |     |     |     |     |     |

| GGC | ACG | CGC | CGC | CCC | ACA | CCC | CCT | GCC | AGT | GGT | AAC | GAG | ATG | ACT | AAC | 737 |
|-----|-----|-----|-----|-----|-----|-----|-----|-----|-----|-----|-----|-----|-----|-----|-----|-----|
| Gly | Thr | Arg | Arg | Pro | Thr | Pro | Pro | Ala | Ser | Gly | Asn | Glu | Met | Thr | Asn |     |
| 200 |     |     |     |     | 205 |     |     |     |     | 210 |     |     |     |     | 215 |     |

| TTA | GCC | TTT | GAA | CTA | GAG | CCC | TTA | GAC | TTA | GAG | GAG | GAC | GAG | GCA | GAG | 785 |
|-----|-----|-----|-----|-----|-----|-----|-----|-----|-----|-----|-----|-----|-----|-----|-----|-----|
| Leu | Ala | Phe | Glu | Leu | Glu | Pro | Leu | Asp | Leu | Glu | Glu | Asp | Glu | Ala | Glu |     |
|     |     |     |     | 220 |     |     |     |     | 225 |     |     |     |     | 230 |     |     |

| CTC | GGT | GAG | CAG | AGC | GGC | TCT | GCC | AAG | ACT | AGC | GTT | AGC | AGT | GTC | ACC | 833 |
|-----|-----|-----|-----|-----|-----|-----|-----|-----|-----|-----|-----|-----|-----|-----|-----|-----|
| Leu | Gly | Glu | Gln | Ser | Gly | Ser | Ala | Lys | Thr | Ser | Val | Ser | Ser | Val | Thr |     |
|     |     |     | 235 |     |     |     |     | 240 |     |     |     |     | 245 |     |     |     |

| ACC | CCG | CCA | CCC | CAC | GGC | ACA | CGC | ATC | CCC | TTC | TTT | AAG | AAG | ACA | GAG | 881 |
|-----|-----|-----|-----|-----|-----|-----|-----|-----|-----|-----|-----|-----|-----|-----|-----|-----|
| Thr | Pro | Pro | Pro | His | Gly | Thr | Arg | Ile | Pro | Phe | Phe | Lys | Lys | Thr | Glu |     |
|     |     | 250 |     |     |     |     | 255 |     |     |     |     | 260 |     |     |     |     |

| CAC | GTG | CCC | CCC | TAT | GAC | GTG | GTG | CCT | TCC | ATG | AGG | CCC | ATC | ATC | CTG | 929 |
|-----|-----|-----|-----|-----|-----|-----|-----|-----|-----|-----|-----|-----|-----|-----|-----|-----|
| His | Val | Pro | Pro | Tyr | Asp | Val | Val | Pro | Ser | Met | Arg | Pro | Ile | Ile | Leu |     |
|     | 265 |     |     |     |     | 270 |     |     |     |     | 275 |     |     |     |     |     |

| GTG | GGA | CCG | TCG | CTC | AAG | GGC | TAT | GAG | GTG | ACA | GAC | ATG | ATG | CAG | AAA | 977 |
|-----|-----|-----|-----|-----|-----|-----|-----|-----|-----|-----|-----|-----|-----|-----|-----|-----|
| Val | Gly | Pro | Ser | Leu | Lys | Gly | Tyr | Glu | Val | Thr | Asp | Met | Met | Gln | Lys |     |
| 280 |     |     |     |     | 285 |     |     |     |     | 290 |     |     |     |     | 295 |     |

| GCT | TTG | TTT | GAC | TTC | CTG | AAG | CAT | CGG | TTT | GAT | GGC | AGG | ATC | TCC | ATC | 1025 |
|-----|-----|-----|-----|-----|-----|-----|-----|-----|-----|-----|-----|-----|-----|-----|-----|------|
| Ala | Leu | Phe | Asp | Phe | Leu | Lys | His | Arg | Phe | Asp | Gly | Arg | Ile | Ser | Ile |      |
|     |     |     |     | 300 |     |     |     |     | 305 |     |     |     |     | 310 |     |      |

| ACG | CGG | GTG | ACA | GCC | GAC | ATC | TCC | CTG | GCT | AAG | CGC | TCA | GTC | CTC | AAC | 1073 |
|-----|-----|-----|-----|-----|-----|-----|-----|-----|-----|-----|-----|-----|-----|-----|-----|------|
| Thr | Arg | Val | Thr | Ala | Asp | Ile | Ser | Leu | Ala | Lys | Arg | Ser | Val | Leu | Asn |      |
|     |     |     | 315 |     |     |     |     | 320 |     |     |     |     | 325 |     |     |      |

| AAC | CCC | AGC | AAG | CAC | ATC | ATC | ATC | GAG | CGC | TCC | AAC | ACA | CGC | TCC | AGC | 1121 |
|-----|-----|-----|-----|-----|-----|-----|-----|-----|-----|-----|-----|-----|-----|-----|-----|------|
| Asn | Pro | Ser | Lys | His | Ile | Ile | Ile | Glu | Arg | Ser | Asn | Thr | Arg | Ser | Ser |      |
|     |     | 330 |     |     |     |     | 335 |     |     |     |     | 340 |     |     |     |      |

| CTG | GCT | GAG | GTG | CAG | AGT | GAG | ATT | GAA | CGA | ATC | TTC | GAG | CTG | GCC | CGG | 1169 |
|-----|-----|-----|-----|-----|-----|-----|-----|-----|-----|-----|-----|-----|-----|-----|-----|------|
| Leu | Ala | Glu | Val | Gln | Ser | Glu | Ile | Glu | Arg | Ile | Phe | Glu | Leu | Ala | Arg |      |
| 345 |     |     |     |     | 350 |     |     |     |     | 355 |     |     |     |     |     |      |

| ACC | CTC | CAG | CTG | GTC | GCT | CTG | GAC | GCG | GAC | ACC | ATC | AAC | CAC | CCT | GCC | 1217 |
|-----|-----|-----|-----|-----|-----|-----|-----|-----|-----|-----|-----|-----|-----|-----|-----|------|
| Thr | Leu | Gln | Leu | Val | Ala | Leu | Asp | Ala | Asp | Thr | Ile | Asn | His | Pro | Ala |      |
| 360 |     |     |     |     | 365 |     |     |     |     | 370 |     |     |     |     | 375 |      |

| CAG | CTC | TCC | AAG | ACC | TCA | CTG | GCG | CCC | ATC | ATT | GTT | TAC | ATC | AAG | ATC | 1265 |
|-----|-----|-----|-----|-----|-----|-----|-----|-----|-----|-----|-----|-----|-----|-----|-----|------|
| Gln | Leu | Ser | Lys | Thr | Ser | Leu | Ala | Pro | Ile | Ile | Val | Tyr | Ile | Lys | Ile |      |
|     |     |     |     | 380 |     |     |     |     | 385 |     |     |     |     | 390 |     |      |

| ACC | TCC | CCC | AAG | GTA | CTT | CAG | AGG | CTC | ATC | AAG | TCC | CGG | GGG | AAG | TCT | 1313 |
|-----|-----|-----|-----|-----|-----|-----|-----|-----|-----|-----|-----|-----|-----|-----|-----|------|
| Thr | Ser | Pro | Lys | Val | Leu | Gln | Arg | Leu | Ile | Lys | Ser | Arg | Gly | Lys | Ser |      |
|     |     |     | 395 |     |     |     |     | 400 |     |     |     |     | 405 |     |     |      |

| CAG | TCC | AAA | CAC | CTC | AAC | GTC | CAG | ATA | GCA | GCC | TCG | GAG | AAG | CTG | GCG | 1361 |
|-----|-----|-----|-----|-----|-----|-----|-----|-----|-----|-----|-----|-----|-----|-----|-----|------|
| Gln | Ser | Lys | His | Leu | Asn | Val | Gln | Ile | Ala | Ala | Ser | Glu | Lys | Leu | Ala |      |
|     |     | 410 |     |     |     |     | 415 |     |     |     |     | 420 |     |     |     |      |

| CAG | TGT | CCG | CCC | GAA | ATG | TTT | GAC | ATC | ATC | CTG | GAC | GAG | AAC | CAA | TTG | 1409 |
|-----|-----|-----|-----|-----|-----|-----|-----|-----|-----|-----|-----|-----|-----|-----|-----|------|
| Gln | Cys | Pro | Pro | Glu | Met | Phe | Asp | Ile | Ile | Leu | Asp | Glu | Asn | Gln | Leu |      |
|     | 425 |     |     |     |     | 430 |     |     |     |     | 435 |     |     |     |     |      |

| GAG | GAT | GCC | TGC | GAG | CAC | CTG | GCC | GAG | TAC | TTG | GAA | GCC | TAC | TGG | AAG | 1457 |
|-----|-----|-----|-----|-----|-----|-----|-----|-----|-----|-----|-----|-----|-----|-----|-----|------|
| Glu | Asp | Ala | Cys | Glu | His | Leu | Ala | Glu | Tyr | Leu | Glu | Ala | Tyr | Trp | Lys |      |
| 440 |     |     |     |     | 445 |     |     |     |     | 450 |     |     |     |     | 455 |      |

| GCC | ACA | CAC | CCG | CCC | AGC | AGC | ACA | CCG | CCC | AAT | CCG | CTG | CTG | AAC | CGC | 1505 |

-continued

| Ala | Thr | His | Pro | Pro | Ser | Ser | Thr | Pro | Pro | Asn | Pro | Leu | Leu | Asn | Arg |
|---|---|---|---|---|---|---|---|---|---|---|---|---|---|---|---|
|   |   |   |   | 460 |   |   |   |   | 465 |   |   |   |   | 470 |   |

```
ACC ATG GCC ACC GCA GCC CTG GCC GCC AGC CCT GCC CCT GTC TCC AAC      1553
Thr Met Ala Thr Ala Ala Leu Ala Ala Ser Pro Ala Pro Val Ser Asn
            475                     480                 485

CTC CAG GTA CAG GTG CTC ACC TCG CTC AGG AGA AAC CTC AGC TTC TGG      1601
Leu Gln Val Gln Val Leu Thr Ser Leu Arg Arg Asn Leu Ser Phe Trp
        490                     495                 500

GGC GGG CTG GAG ACC TCC CAG CGG GGC GGC GGT GCG GTG CCC CAA CAG      1649
Gly Gly Leu Glu Thr Ser Gln Arg Gly Gly Gly Ala Val Pro Gln Gln
    505                     510                 515

CAG GAG CAC GCC ATG TAG CGGGGGACCG CCCGTCTTCC CTCCGCCCAG GGCGTGGAA   1706
Gln Glu His Ala Met *
520

CTGGAGTGCA GGGAACATGG GCAAGGAAGG GAAGAGCTTT ATTTTGTAAA AAACGTGGTG   1766

AGCGGC                                                                1772
```

( 2 ) INFORMATION FOR SEQ ID NO:3:

( i ) SEQUENCE CHARACTERISTICS:
        ( A ) LENGTH: 5975 base pairs
        ( B ) TYPE: nucleic acid
        ( C ) STRANDEDNESS: Not Relevant
        ( D ) TOPOLOGY: Not Relevant ( i i ) MOLECULE TYPE: Genomic DNA ( i x ) FEATURE:
        ( A ) NAME/KEY: Coding Sequence
        ( B ) LOCATION: 79...5700
        ( D ) OTHER INFORMATION: product="Alpha-1 subunit of animal
            calcium channel"

( x i ) SEQUENCE DESCRIPTION: SEQ ID NO:3:

```
GCGGGGAACA CTGGGGACGC AGGGAAGAGA GGGCCGCGGG GTGGGGGAGC AGCAGGAAGC      60

GCCGTGGCCA GGGAAGCC ATG GAG CCA TCC TCA CCC CAG GAT GAG GGC CTG      111
                    Met Glu Pro Ser Ser Pro Gln Asp Glu Gly Leu
                     1               5                   10

AGG AAG AAA CAG CCC AAG AAG CCC CTG CCC GAG GTC CTG CCC AGG CCG      159
Arg Lys Lys Gln Pro Lys Lys Pro Leu Pro Glu Val Leu Pro Arg Pro
                15                  20                  25

CCG CGG GCT CTG TTC TGC CTG ACC CTG CAG AAC CCG CTG AGG AAG GCG      207
Pro Arg Ala Leu Phe Cys Leu Thr Leu Gln Asn Pro Leu Arg Lys Ala
        30                      35                  40

TGC ATC AGC ATC GTG GAA TGG AAA CCC TTC GAG ACC ATC ATC CTG CTC      255
Cys Ile Ser Ile Val Glu Trp Lys Pro Phe Glu Thr Ile Ile Leu Leu
    45                  50                  55

ACC ATC TTT GCC AAC TGT GTG GCC CTG GCC GTG TAC CTG CCC ATG CCC      303
Thr Ile Phe Ala Asn Cys Val Ala Leu Ala Val Tyr Leu Pro Met Pro
60                  65                  70                  75

GAG GAT GAC AAC AAC TCC CTG AAC CTG GGC CTG GAG AAG CTG GAG TAC      351
Glu Asp Asp Asn Asn Ser Leu Asn Leu Gly Leu Glu Lys Leu Glu Tyr
                    80                  85                  90

TTC TTC CTC ACC GTC TTC TCC ATC GAA GCC GCC ATG AAG ATC ATC GCC      399
Phe Phe Leu Thr Val Phe Ser Ile Glu Ala Ala Met Lys Ile Ile Ala
                95                  100                 105

TAC GGC TTC CTG TTC CAC CAG GAC GCC TAC CTG CGC AGC GGC TGG AAC      447
Tyr Gly Phe Leu Phe His Gln Asp Ala Tyr Leu Arg Ser Gly Trp Asn
        110                     115                 120

GTG CTG GAC TTC ATC ATC GTC TTC CTG GGG GTC TTC ACG GCG ATT CTG      495
Val Leu Asp Phe Ile Ile Val Phe Leu Gly Val Phe Thr Ala Ile Leu
    125                     130                 135
```

| | | | | | | | | | | | | | | | | |
|---|---|---|---|---|---|---|---|---|---|---|---|---|---|---|---|---|
| GAA | CAG | GTC | AAC | GTC | ATC | CAG | AGC | AAC | ACG | GCC | CCG | ATG | AGC | AGC | AAA | 543 |
| Glu 140 | Gln | Val | Asn | Val | Ile 145 | Gln | Ser | Asn | Thr 150 | Ala | Pro | Met | Ser | Ser 155 | Lys | |
| GGA | GCC | GGC | CTG | GAC | GTC | AAG | GCC | CTG | AGG | GCC | TTC | CGT | GTG | CTC | AGA | 591 |
| Gly | Ala | Gly | Leu | Asp 160 | Val | Lys | Ala | Leu | Arg 165 | Ala | Phe | Arg | Val | Leu 170 | Arg | |
| CCC | CTC | CGG | CTG | GTG | TCG | GGG | GTG | CCT | AGT | TTG | CAG | GTG | GTC | CTC | AAC | 639 |
| Pro | Leu | Arg | Leu 175 | Val | Ser | Gly | Val | Pro 180 | Ser | Leu | Gln | Val | Val 185 | Leu | Asn | |
| TCC | ATC | TTC | AAG | GCC | ATG | CTC | CCC | CTG | TTC | CAC | ATC | GCC | CTG | CTC | GTC | 687 |
| Ser | Ile | Phe 190 | Lys | Ala | Met | Leu | Pro 195 | Leu | Phe | His | Ile | Ala 200 | Leu | Leu | Val | |
| CTC | TTC | ATG | GTC | ATC | ATC | TAC | GCC | ATC | ATC | GGG | CTG | GAG | CTC | TTC | AAG | 735 |
| Leu | Phe 205 | Met | Val | Ile | Ile | Tyr 210 | Ala | Ile | Ile | Gly | Leu 215 | Glu | Leu | Phe | Lys | |
| GGC | AAG | ATG | CAC | AAG | ACC | TGC | TAC | TAC | ATC | GGG | ACA | GAC | ATC | GTG | GCC | 783 |
| Gly 220 | Lys | Met | His | Lys | Thr 225 | Cys | Tyr | Tyr | Ile | Gly 230 | Thr | Asp | Ile | Val | Ala 235 | |
| ACA | GTG | GAG | AAT | GAG | AAG | CCC | TCG | CCC | TGC | GCT | AGG | ACG | GGC | TCG | GGG | 831 |
| Thr | Val | Glu | Asn 240 | Glu | Lys | Pro | Ser | Pro 245 | Cys | Ala | Arg | Thr | Gly 250 | Ser | Gly | |
| CGC | CCC | TGC | ACC | ATC | AAC | GGC | AGC | GAG | TGC | CGG | GGC | GGC | TGG | CCG | GGG | 879 |
| Arg | Pro | Cys | Thr 255 | Ile | Asn | Gly | Ser | Glu 260 | Cys | Arg | Gly | Gly | Trp 265 | Pro | Gly | |
| CCC | AAC | CAC | GGC | ATC | ACG | CAC | TTC | GAC | AAC | TTC | GGC | TTC | TCC | ATG | CTC | 927 |
| Pro | Asn | His 270 | Gly | Ile | Thr | His | Phe 275 | Asp | Asn | Phe | Gly | Phe 280 | Ser | Met | Leu | |
| ACC | GTG | TAC | CAG | TGC | ATC | ACC | ATG | GAG | GGC | TGG | ACA | GAT | GTC | CTC | TAC | 975 |
| Thr | Val 285 | Tyr | Gln | Cys | Ile | Thr 290 | Met | Glu | Gly | Trp | Thr 295 | Asp | Val | Leu | Tyr | |
| TGG | GTC | AAC | GAT | GCC | ATC | GGG | AAC | GAG | TGG | CCC | TGG | ATC | TAC | TTT | GTC | 1023 |
| Trp 300 | Val | Asn | Asp | Ala | Ile 305 | Gly | Asn | Glu | Trp | Pro 310 | Trp | Ile | Tyr | Phe | Val 315 | |
| ACT | CTC | ATC | CTG | CTG | GGG | TCC | TTC | TTC | ATC | CTC | AAC | CTG | GTG | CTG | GGC | 1071 |
| Thr | Leu | Ile | Leu | Leu 320 | Gly | Ser | Phe | Phe | Ile 325 | Leu | Asn | Leu | Val | Leu 330 | Gly | |
| GTC | CTG | AGT | GGG | GAA | TTC | ACC | AAG | GAG | CGG | GAG | AAG | GCC | AAG | TCC | AGG | 1119 |
| Val | Leu | Ser | Gly 335 | Glu | Phe | Thr | Lys | Glu 340 | Arg | Glu | Lys | Ala | Lys 345 | Ser | Arg | |
| GGA | ACC | TTC | CAG | AAG | CTG | CGG | GAG | AAG | CAG | CAG | CTG | GAG | GAG | GAC | CTT | 1167 |
| Gly | Thr | Phe 350 | Gln | Lys | Leu | Arg | Glu 355 | Lys | Gln | Gln | Leu | Glu 360 | Glu | Asp | Leu | |
| CGG | GGC | TAC | ATG | AGC | TGG | ATC | ACG | CAG | GGC | GAG | GTC | ATG | GAC | GTG | GAG | 1215 |
| Arg | Gly 365 | Tyr | Met | Ser | Trp | Ile 370 | Thr | Gln | Gly | Glu | Val 375 | Met | Asp | Val | Glu | |
| GAC | CTG | AGA | GAA | GGA | AAG | CTG | TCC | TTG | GAA | GAG | GGA | GGC | TCC | GAC | ACG | 1263 |
| Asp 380 | Leu | Arg | Glu | Gly | Lys 385 | Leu | Ser | Leu | Glu | Glu 390 | Gly | Gly | Ser | Asp | Thr 395 | |
| GAA | AGC | CTG | TAC | GAA | ATC | GAG | GGC | TTG | AAC | AAA | ATC | ATC | CAG | TTC | ATC | 1311 |
| Glu | Ser | Leu | Tyr | Glu 400 | Ile | Glu | Gly | Leu | Asn 405 | Lys | Ile | Ile | Gln | Phe 410 | Ile | |
| CGA | CAC | TGG | AGG | CAG | TGG | AAC | CGT | GTC | TTT | CGC | TGG | AAG | TGC | CAT | GAC | 1359 |
| Arg | His | Trp | Arg 415 | Gln | Trp | Asn | Arg | Val 420 | Phe | Arg | Trp | Lys | Cys 425 | His | Asp | |
| CTG | GTG | AAG | TCG | AGA | GTG | TTC | TAC | TGG | CTG | GTC | ATC | CTG | ATC | GTG | GCC | 1407 |
| Leu | Val | Lys | Ser | Arg 430 | Val | Phe | Tyr | Trp | Leu 435 | Val | Ile | Leu | Ile | Val 440 | Ala | |
| CTC | AAC | ACC | CTG | TCC | ATC | GCC | TCG | GAG | CAC | CAC | AAC | CAG | CCG | CTC | TGG | 1455 |
| Leu | Asn | Thr | Leu 445 | Ser | Ile | Ala | Ser | Glu 450 | His | His | Asn | Gln | Pro 455 | Leu | Trp | |

| | | | | | | | | | | | | | | | |
|---|---|---|---|---|---|---|---|---|---|---|---|---|---|---|---|
| CTG | ACC | CAC | TTG | CAA | GAC | ACT | GCC | AAT | CGA | GTG | CTG | CTG | TCA | CTC | TTC | 1503 |
| Leu | Thr | His | Leu | Gln | Asp | Thr | Ala | Asn | Arg | Val | Leu | Leu | Ser | Leu | Phe | |
| 460 | | | | 465 | | | | | 470 | | | | | 475 | | |
| ACC | ATC | GAG | ATG | CTG | CTG | AAG | ATG | TAC | GGG | CTG | GGC | CTG | CGC | CAG | TAC | 1551 |
| Thr | Ile | Glu | Met | Leu | Leu | Lys | Met | Tyr | Gly | Leu | Gly | Leu | Arg | Gln | Tyr | |
| | | | | 480 | | | | 485 | | | | | 490 | | | |
| TTC | ATG | TCC | ATC | TTC | AAC | CGC | TTC | GAC | TGC | TTC | GTG | GTG | TGC | AGC | GGC | 1599 |
| Phe | Met | Ser | Ile | Phe | Asn | Arg | Phe | Asp | Cys | Phe | Val | Val | Cys | Ser | Gly | |
| | | | 495 | | | | | 500 | | | | | 505 | | | |
| ATC | CTG | GAG | CTG | CTG | CTG | GTG | GAG | TCG | GGC | GCC | ATG | ACG | CCG | CTG | GGC | 1647 |
| Ile | Leu | Glu | Leu | Leu | Leu | Val | Glu | Ser | Gly | Ala | Met | Thr | Pro | Leu | Gly | |
| | | 510 | | | | | 515 | | | | | 520 | | | | |
| ATC | TCC | GTG | TTG | CGC | TGC | ATC | CGC | CTC | CTG | AGG | CTC | TTC | AAG | ATC | ACC | 1695 |
| Ile | Ser | Val | Leu | Arg | Cys | Ile | Arg | Leu | Leu | Arg | Leu | Phe | Lys | Ile | Thr | |
| | | 525 | | | | 530 | | | | | 535 | | | | | |
| AAG | TAC | TGG | ACG | TCG | CTC | AGC | AAC | CTG | GTG | GCC | TCC | CTG | CTC | AAC | TCC | 1743 |
| Lys | Tyr | Trp | Thr | Ser | Leu | Ser | Asn | Leu | Val | Ala | Ser | Leu | Leu | Asn | Ser | |
| 540 | | | | | 545 | | | | | 550 | | | | | 555 | |
| ATC | CGC | TCC | ATC | GCC | TCG | CTG | CTG | CTG | CTC | TTC | CTC | TTC | ATC | ATC | | 1791 |
| Ile | Arg | Ser | Ile | Ala | Ser | Leu | Leu | Leu | Leu | Phe | Leu | Phe | Ile | Ile | | |
| | | | | 560 | | | | | 565 | | | | | 570 | | |
| ATC | TTC | GCC | CTG | CTG | GGC | ATC | CAG | CTC | TTC | GGG | GGG | CGG | TAC | GAC | TTC | 1839 |
| Ile | Phe | Ala | Leu | Leu | Gly | Ile | Gln | Leu | Phe | Gly | Gly | Arg | Tyr | Asp | Phe | |
| | | | 575 | | | | | 580 | | | | | 585 | | | |
| GAG | GAC | ACG | GAA | GTG | CGA | CGC | AGC | AAC | TTC | GAC | AAC | TTC | CCC | CAG | GCC | 1887 |
| Glu | Asp | Thr | Glu | Val | Arg | Arg | Ser | Asn | Phe | Asp | Asn | Phe | Pro | Gln | Ala | |
| | | 590 | | | | | 595 | | | | | 600 | | | | |
| CTC | ATC | AGC | GTC | TTC | CAG | GTG | CTG | ACG | GGT | GAG | GAC | TGG | AAC | TCC | GTG | 1935 |
| Leu | Ile | Ser | Val | Phe | Gln | Val | Leu | Thr | Gly | Glu | Asp | Trp | Asn | Ser | Val | |
| | 605 | | | | | 610 | | | | | 615 | | | | | |
| ATG | TAC | AAC | GGG | ATC | ATG | GCC | TAC | GGA | GGC | CCG | TCC | TAC | CCG | GGC | GTT | 1983 |
| Met | Tyr | Asn | Gly | Ile | Met | Ala | Tyr | Gly | Gly | Pro | Ser | Tyr | Pro | Gly | Val | |
| 620 | | | | | 625 | | | | | 630 | | | | | 635 | |
| CTC | GTG | TGC | ATC | TAT | TTC | ATC | ATC | CTT | TTT | GTC | TGC | GGC | AAC | TAT | ATC | 2031 |
| Leu | Val | Cys | Ile | Tyr | Phe | Ile | Ile | Leu | Phe | Val | Cys | Gly | Asn | Tyr | Ile | |
| | | | | 640 | | | | | 645 | | | | | 650 | | |
| CTG | CTG | AAT | GTC | TTC | CTG | GCC | ATC | GCC | GTG | GAC | AAC | CTG | GCC | GAG | GCC | 2079 |
| Leu | Leu | Asn | Val | Phe | Leu | Ala | Ile | Ala | Val | Asp | Asn | Leu | Ala | Glu | Ala | |
| | | | 655 | | | | | 660 | | | | | 665 | | | |
| GAG | AGC | CTG | ACT | TCC | GCG | CAA | AAG | GCC | AAG | GCC | GAG | GAG | AGG | AAA | CGT | 2127 |
| Glu | Ser | Leu | Thr | Ser | Ala | Gln | Lys | Ala | Lys | Ala | Glu | Glu | Arg | Lys | Arg | |
| | | 670 | | | | | 675 | | | | | 680 | | | | |
| AGG | AAG | ATG | TCC | AGG | GGT | CTC | CCT | GAC | AAG | ACG | GAG | GAG | GAG | AAG | TCT | 2175 |
| Arg | Lys | Met | Ser | Arg | Gly | Leu | Pro | Asp | Lys | Thr | Glu | Glu | Glu | Lys | Ser | |
| | 685 | | | | | 690 | | | | | 695 | | | | | |
| GTG | ATG | GCC | AAG | AAG | CTG | GAG | CAG | AAG | CCC | AAG | GGG | GAG | GGC | ATC | CCC | 2223 |
| Val | Met | Ala | Lys | Lys | Leu | Glu | Gln | Lys | Pro | Lys | Gly | Glu | Gly | Ile | Pro | |
| 700 | | | | | 705 | | | | | 710 | | | | | 715 | |
| ACC | ACT | GCC | AAG | CTC | AAG | GTC | GAT | GAG | TTC | GAA | TCT | AAC | GTC | AAC | GAG | 2271 |
| Thr | Thr | Ala | Lys | Leu | Lys | Val | Asp | Glu | Phe | Glu | Ser | Asn | Val | Asn | Glu | |
| | | | | 720 | | | | | 725 | | | | | 730 | | |
| GTG | AAG | GAC | CCC | TAC | CCT | TCA | GCT | GAC | TTC | CCA | GGG | GAT | GAT | GAG | GAG | 2319 |
| Val | Lys | Asp | Pro | Tyr | Pro | Ser | Ala | Asp | Phe | Pro | Gly | Asp | Asp | Glu | Glu | |
| | | | 735 | | | | | 740 | | | | | 745 | | | |
| GAC | GAG | CCT | GAG | ATC | CCA | GTG | AGC | CCC | CGA | CCG | CGC | CCG | CTG | GCC | GAG | 2367 |
| Asp | Glu | Pro | Glu | Ile | Pro | Val | Ser | Pro | Arg | Pro | Arg | Pro | Leu | Ala | Glu | |
| | | | | 750 | | | | | 755 | | | | | 760 | | |
| CTG | CAG | CTC | AAA | GAG | AAG | GCA | GTG | CCC | ATC | CCG | GAA | GCC | AGC | TCC | TTC | 2415 |
| Leu | Gln | Leu | Lys | Glu | Lys | Ala | Val | Pro | Ile | Pro | Glu | Ala | Ser | Ser | Phe | |
| | | 765 | | | | | 770 | | | | | 775 | | | | |

| | | | | | | | | | | | | | | | | |
|---|---|---|---|---|---|---|---|---|---|---|---|---|---|---|---|---|
| TTC | ATC | TTC | AGT | CCC | ACC | AAT | AAG | GTC | CGT | GTC | CTG | TGT | CAC | CGC | ATC | 2463 |
| Phe 780 | Ile | Phe | Ser | Pro 785 | Thr | Asn | Lys | Val 790 | Arg | Val | Leu | Cys | His | Arg | Ile 795 | |
| GTC | AAC | GCC | ACC | TGG | TTC | ACC | AAC | TTC | ATC | CTG | CTC | TTC | ATC | CTG | CTC | 2511 |
| Val | Asn | Ala | Thr | Trp 800 | Phe | Thr | Asn | Phe 805 | Ile | Leu | Leu | Phe | Ile 810 | Leu | Leu | |
| AGC | AGT | GCT | GCG | CTG | GCC | GCC | GAG | GAC | CCC | ATC | CGG | GCG | GAG | TCC | GTG | 2559 |
| Ser | Ser | Ala | Ala 815 | Leu | Ala | Ala | Glu | Asp 820 | Pro | Ile | Arg | Ala | Glu 825 | Ser | Val | |
| AGG | AAT | CAG | ATC | CTT | GGA | TAT | TTT | GAT | ATT | GCC | TTC | ACC | TCT | GTC | TTC | 2607 |
| Arg | Asn | Gln 830 | Ile | Leu | Gly | Tyr | Phe 835 | Asp | Ile | Ala | Phe | Thr 840 | Ser | Val | Phe | |
| ACT | GTG | GAG | ATT | GTC | CTC | AAG | ATG | ACA | ACC | TAC | GGC | GCC | TTC | CTG | CAC | 2655 |
| Thr | Val | Glu 845 | Ile | Val | Leu | Lys | Met 850 | Thr | Thr | Tyr | Gly | Ala 855 | Phe | Leu | His | |
| AAG | GGC | TCC | TTC | TGC | CGC | AAC | TAC | TTC | AAC | ATC | CTG | GAC | CTG | CTG | GTG | 2703 |
| Lys | Gly 860 | Ser | Phe | Cys | Arg 865 | Asn | Tyr | Phe | Asn | Ile 870 | Leu | Asp | Leu | Leu | Val 875 | |
| GTG | GCC | GTG | TCT | CTC | ATC | TCC | ATG | GGT | CTC | GAG | TCC | AGC | ACC | ATC | TCC | 2751 |
| Val | Ala | Val | Ser | Leu 880 | Ile | Ser | Met | Gly | Leu 885 | Glu | Ser | Ser | Thr | Ile 890 | Ser | |
| GTG | GTA | AAG | ATC | CTG | AGA | GTG | CTA | AGG | GTG | CTC | CGG | CCC | CTG | CGA | GCC | 2799 |
| Val | Val | Lys | Ile 895 | Leu | Arg | Val | Leu | Arg 900 | Val | Leu | Arg | Pro | Leu 905 | Arg | Ala | |
| ATC | AAC | AGA | GCC | AAA | GGG | TTG | AAG | CAC | GTG | GTC | CAG | TGC | GTG | TTC | GTG | 2847 |
| Ile | Asn | Arg | Ala | Lys 910 | Gly | Leu | Lys | His | Val 915 | Val | Gln | Cys | Val 920 | Phe | Val | |
| GCC | ATC | CGC | ACC | ATC | GGG | AAT | ATC | GTC | CTG | GTC | ACC | ACG | CTC | CTG | CAG | 2895 |
| Ala | Ile 925 | Arg | Thr | Ile | Gly | Asn 930 | Ile | Val | Leu | Val | Thr 935 | Thr | Leu | Leu | Gln | |
| TTC | ATG | TTC | GCC | TGC | ATC | GGT | GTC | CAG | CTC | TTC | AAG | GGC | AAG | TTC | TTC | 2943 |
| Phe | Met 940 | Phe | Ala | Cys | Ile | Gly 945 | Val | Gln | Leu | Phe | Lys 950 | Gly | Lys | Phe | Phe 955 | |
| AGC | TGC | AAT | GAC | CTA | TCC | AAG | ATG | ACA | GAA | GAG | GAG | TGC | AGG | GGC | TAC | 2991 |
| Ser | Cys | Asn | Asp | Leu 960 | Ser | Lys | Met | Thr | Glu 965 | Glu | Glu | Cys | Arg | Gly 970 | Tyr | |
| TAC | TAT | GTG | TAC | AAG | GAC | GGG | GAC | CCC | ACG | CAG | ATG | GAG | CTG | CGC | CCC | 3039 |
| Tyr | Tyr | Val | Tyr 975 | Lys | Asp | Gly | Asp | Pro 980 | Thr | Gln | Met | Glu | Leu 985 | Arg | Pro | |
| CGC | CAG | TGG | ATA | CAC | AAT | GAC | TTC | CAC | TTT | GAC | AAC | GTG | CTG | TCG | GCC | 3087 |
| Arg | Gln | Trp 990 | Ile | His | Asn | Asp | Phe 995 | His | Phe | Asp | Asn | Val 1000 | Leu | Ser | Ala | |
| ATG | ATG | TCG | CTC | TTC | ACG | GTG | TCC | ACC | TTC | GAG | GGA | TGG | CCC | CAG | CTG | 3135 |
| Met | Met 1005 | Ser | Leu | Phe | Thr | Val 1010 | Ser | Thr | Phe | Glu | Gly 1015 | Trp | Pro | Gln | Leu | |
| CTG | TAC | AGG | GCC | ATA | GAC | TCC | AAC | GAG | GAG | GAC | ATG | GGC | CCC | GTT | TAC | 3183 |
| Leu 1020 | Tyr | Arg | Ala | Ile | Asp 1025 | Ser | Asn | Glu | Glu | Asp 1030 | Met | Gly | Pro | Val | Tyr 1035 | |
| AAC | AAC | CGA | GTG | GAG | ATG | GCC | ATC | TTC | TTC | ATC | ATC | TAC | ATC | ATC | CTC | 3231 |
| Asn | Asn | Arg | Val | Glu 1040 | Met | Ala | Ile | Phe | Phe 1045 | Ile | Ile | Tyr | Ile | Ile 1050 | Leu | |
| ATT | GCC | TTC | TTC | ATG | ATG | AAC | ATC | TTT | GTG | GGC | TTT | GTC | ATC | GTC | ACC | 3279 |
| Ile | Ala | Phe | Phe 1055 | Met | Met | Asn | Ile | Phe 1060 | Val | Gly | Phe | Val | Ile 1065 | Val | Thr | |
| TTC | CAG | GAG | CAG | GGG | GAG | ACG | GAG | TAC | AAG | AAC | TGC | GAG | CTG | GAC | AAG | 3327 |
| Phe | Gln | Glu | Gln 1070 | Gly | Glu | Thr | Glu | Tyr 1075 | Lys | Asn | Cys | Glu | Leu 1080 | Asp | Lys | |
| AAC | CAG | CGC | CAG | TGT | GTG | CAG | TAT | GCC | CTG | AAG | GCC | CGC | CCA | CTT | CGG | 3375 |
| Asn | Gln | Arg | Gln 1085 | Cys | Val | Gln | Tyr | Ala 1090 | Leu | Lys | Ala | Arg | Pro 1095 | Leu | Arg | |

```
TCG TAC ATC CCC AAG AAC CCA TAC CAG TAC CAG GTG TGG TAC GTC GTC    3423
Ser Tyr Ile Pro Lys Asn Pro Tyr Gln Tyr Gln Val Trp Tyr Val Val
1100            1105                1110                1115

ACC TCC TCC TAC TTT GAA TAC CTG ATG TTC GCC CTC ATC ATG CTC AAC    3471
Thr Ser Ser Tyr Phe Glu Tyr Leu Met Phe Ala Leu Ile Met Leu Asn
                1120                1125                1130

ACC ATC TGC CTG GGC ATG CAG CAC TAC CAC CAG TCG GAG GAG ATG AAC    3519
Thr Ile Cys Leu Gly Met Gln His Tyr His Gln Ser Glu Glu Met Asn
            1135                1140                1145

CAC ATC TCA GAC ATC CTC AAT GTG GCC TTC ACC ATC ATC TTC ACG CTG    3567
His Ile Ser Asp Ile Leu Asn Val Ala Phe Thr Ile Ile Phe Thr Leu
        1150                1155                1160

GAG ATG ATT CTC AAG CTC TTG GCG TTC AAG GCC AGG GGC TAT TTC GGA    3615
Glu Met Ile Leu Lys Leu Leu Ala Phe Lys Ala Arg Gly Tyr Phe Gly
    1165                1170                1175

GAC CCC TGG AAT GTG TTC GAC TTC CTG ATC GTC ATC CGC AGC ATC ATT    3663
Asp Pro Trp Asn Val Phe Asp Phe Leu Ile Val Ile Arg Ser Ile Ile
1180                1185                1190                1195

GAC GTC ATC CTC AGC GAG ACT GAC ACT TTC CTG GCC TCC AGC GGG GGA    3711
Asp Val Ile Leu Ser Glu Thr Asp Thr Phe Leu Ala Ser Ser Gly Gly
                1200                1205                1210

CTG TAT TGC CTG GGT GGC GGC TGC GGG AAC GTT GAC CCA GAC GAG AGC    3759
Leu Tyr Cys Leu Gly Gly Gly Cys Gly Asn Val Asp Pro Asp Glu Ser
            1215                1220                1225

GCC CGC ATC TCC AGT GCC TTC TTC CGC CTG TTC CGG GTT ATG AGG CTG    3807
Ala Arg Ile Ser Ser Ala Phe Phe Arg Leu Phe Arg Val Met Arg Leu
        1230                1235                1240

ATC AAG CTG CTG AGT CGG GCC GAG GGC GTG CGC ACG CTG CTG TGG ACG    3855
Ile Lys Leu Leu Ser Arg Ala Glu Gly Val Arg Thr Leu Leu Trp Thr
    1245                1250                1255

TTC ATC AAG TCC TTC CAG GCC CTG CCC TAC GTG GCC CTG CTC ATC GTC    3903
Phe Ile Lys Ser Phe Gln Ala Leu Pro Tyr Val Ala Leu Leu Ile Val
1260                1265                1270                1275

ATG CTG TTC TTC ATC TAC GCC GTC ATC GGC ATG CAG ATG TTT GGA AAG    3951
Met Leu Phe Phe Ile Tyr Ala Val Ile Gly Met Gln Met Phe Gly Lys
                1280                1285                1290

ATC GCC CTG GTG GAC GGG ACC CAG ATC AAC CGC AAC AAC AAC TTC CAG    3999
Ile Ala Leu Val Asp Gly Thr Gln Ile Asn Arg Asn Asn Asn Phe Gln
            1295                1300                1305

ACC TTC CCG CAG GCC GTG CTG CTG CTC TTC AGG TGT GCG ACA GGG GAG    4047
Thr Phe Pro Gln Ala Val Leu Leu Leu Phe Arg Cys Ala Thr Gly Glu
        1310                1315                1320

GCG TGG CAA GAG ATC CTG CTG GCC TGC AGC TAC GGG AAG TTG TGC GAC    4095
Ala Trp Gln Glu Ile Leu Leu Ala Cys Ser Tyr Gly Lys Leu Cys Asp
    1325                1330                1335

CCA GAG TCA GAC TAC GCC CCG GGC GAG GAG TAC ACG TGT GGC ACC AAC    4143
Pro Glu Ser Asp Tyr Ala Pro Gly Glu Glu Tyr Thr Cys Gly Thr Asn
1340                1345                1350                1355

TTC GCC TAC TAC TAC TTC ATC AGC TTC TAC ATG CTC TGC GCC TTC CTG    4191
Phe Ala Tyr Tyr Tyr Phe Ile Ser Phe Tyr Met Leu Cys Ala Phe Leu
                1360                1365                1370

ATC ATC AAC CTC TTC GTG GCT GTC ATC ATG GAC AAC TTT GAC TAC CTG    4239
Ile Ile Asn Leu Phe Val Ala Val Ile Met Asp Asn Phe Asp Tyr Leu
            1375                1380                1385

ACA CGC GAC TGG TCC ATC CTG GGC CCT CAC CAC CTG GAC GAG TTC AAG    4287
Thr Arg Asp Trp Ser Ile Leu Gly Pro His His Leu Asp Glu Phe Lys
        1390                1395                1400

GCC ATC TGG GCA GAG TAT GAC CCA GAG GCC AAG GGG CGA ATC AAG CAC    4335
Ala Ile Trp Ala Glu Tyr Asp Pro Glu Ala Lys Gly Arg Ile Lys His
    1405                1410                1415
```

```
CTG  GAC  GTG  GTG  ACC  CTG  CTG  AGA  AGG  ATC  CAG  CCC  CCT  CTG  GGC  TTC   4383
Leu  Asp  Val  Val  Thr  Leu  Leu  Arg  Arg  Ile  Gln  Pro  Pro  Leu  Gly  Phe
1420                1425                1430                1435

GGG  AAG  TTC  TGT  CCA  CAC  CGG  GTG  GCC  TGT  AAG  CGC  CTG  GTG  GGC  ATG   4431
Gly  Lys  Phe  Cys  Pro  His  Arg  Val  Ala  Cys  Lys  Arg  Leu  Val  Gly  Met
          1440                1445                1450

AAC  ATG  CCC  CTG  AAC  AGT  GAC  GGC  ACG  GTC  ACC  TTC  AAT  GCC  ACG  CTC   4479
Asn  Met  Pro  Leu  Asn  Ser  Asp  Gly  Thr  Val  Thr  Phe  Asn  Ala  Thr  Leu
               1455                1460                1465

TTT  GCC  CTG  GTG  CGC  ACG  GCC  CTC  AAG  ATC  AAG  ACA  GAA  GGT  AAC  TTC   4527
Phe  Ala  Leu  Val  Arg  Thr  Ala  Leu  Lys  Ile  Lys  Thr  Glu  Gly  Asn  Phe
          1470                1475                1480

GAG  CAG  GCC  AAC  GAG  GAG  CTG  AGG  GCC  ATC  ATC  AAG  AAG  ATC  TGG  AAG   4575
Glu  Gln  Ala  Asn  Glu  Glu  Leu  Arg  Ala  Ile  Ile  Lys  Lys  Ile  Trp  Lys
1485                1490                1495

AGA  ACC  AGC  ATG  AAG  CTA  CTG  GAC  CAG  GTC  ATC  CCT  CCC  ATA  GGA  GAT   4623
Arg  Thr  Ser  Met  Lys  Leu  Leu  Asp  Gln  Val  Ile  Pro  Pro  Ile  Gly  Asp
1500                1505                1510                1515

GAC  GAG  GTG  ACC  GTG  GGG  AAG  TTC  TAC  GCC  ACA  TTC  CTC  ATC  CAG  GAG   4671
Asp  Glu  Val  Thr  Val  Gly  Lys  Phe  Tyr  Ala  Thr  Phe  Leu  Ile  Gln  Glu
               1520                1525                1530

CAC  TTC  CGG  AAG  TTC  ATG  AAG  CGC  CAG  GAG  GAA  TAT  TAT  GGG  TAT  CGG   4719
His  Phe  Arg  Lys  Phe  Met  Lys  Arg  Gln  Glu  Glu  Tyr  Tyr  Gly  Tyr  Arg
          1535                1540                1545

CCC  AAG  AAG  GAC  ACC  GTG  CAG  ATC  CAG  GCT  GGG  CTG  CGG  ACC  ATA  GAG   4767
Pro  Lys  Lys  Asp  Thr  Val  Gln  Ile  Gln  Ala  Gly  Leu  Arg  Thr  Ile  Glu
     1550                1555                1560

GAG  GAG  GCG  GCC  CCT  GAG  ATC  CGC  CGC  ACC  ATC  TCA  GGA  GAC  CTG  ACC   4815
Glu  Glu  Ala  Ala  Pro  Glu  Ile  Arg  Arg  Thr  Ile  Ser  Gly  Asp  Leu  Thr
1565                1570                1575

GCC  GAG  GAG  GAG  CTG  GAG  AGA  GCC  ATG  GTG  GAG  GCT  GCG  ATG  GAG  GAG   4863
Ala  Glu  Glu  Glu  Leu  Glu  Arg  Ala  Met  Val  Glu  Ala  Ala  Met  Glu  Glu
1580                1585                1590                1595

AGG  ATC  TTC  CGG  AGG  ACC  GGA  GGC  CTG  TTT  GGC  CAG  GTG  GAC  ACC  TTC   4911
Arg  Ile  Phe  Arg  Arg  Thr  Gly  Gly  Leu  Phe  Gly  Gln  Val  Asp  Thr  Phe
               1600                1605                1610

CTG  GAA  AGG  ACC  AAC  TCC  CTA  CCC  CCG  GTG  ATG  GCC  AAC  CAA  AGA  CCG   4959
Leu  Glu  Arg  Thr  Asn  Ser  Leu  Pro  Pro  Val  Met  Ala  Asn  Gln  Arg  Pro
          1615                1620                1625

CTC  CAG  TTT  GCT  GAG  ATA  GAA  ATG  GAA  GAG  CTT  GAG  TCG  CCT  GTC  TTC   5007
Leu  Gln  Phe  Ala  Glu  Ile  Glu  Met  Glu  Glu  Leu  Glu  Ser  Pro  Val  Phe
1630                1635                1640

TTG  GAG  GAC  TTC  CCT  CAA  GAC  GCA  AGA  ACC  AAC  CCT  CTC  GCT  CGT  GCC   5055
Leu  Glu  Asp  Phe  Pro  Gln  Asp  Ala  Arg  Thr  Asn  Pro  Leu  Ala  Arg  Ala
     1645                1650                1655

AAT  ACC  AAC  AAC  GCC  AAT  GCC  AAT  GTT  GCC  TAT  GGC  AAC  AGC  AAC  CAT   5103
Asn  Thr  Asn  Asn  Ala  Asn  Ala  Asn  Val  Ala  Tyr  Gly  Asn  Ser  Asn  His
1660                1665                1670                1675

AGC  AAC  AAC  CAG  ATG  TTT  TCC  AGC  GTC  CAC  TGT  GAA  AGG  GAG  TTC  CCG   5151
Ser  Asn  Asn  Gln  Met  Phe  Ser  Ser  Val  His  Cys  Glu  Arg  Glu  Phe  Pro
               1680                1685                1690

GGA  GAG  GCG  GAG  ACA  CCG  GCT  GCC  GGA  CGA  GGA  GCC  CTC  AGC  CAC  TCC   5199
Gly  Glu  Ala  Glu  Thr  Pro  Ala  Ala  Gly  Arg  Gly  Ala  Leu  Ser  His  Ser
          1695                1700                1705

CAC  AGG  GCC  CTG  GGA  CCT  CAC  AGC  AAG  CCC  TGT  GCT  GGA  AAA  CTG  AAT   5247
His  Arg  Ala  Leu  Gly  Pro  His  Ser  Lys  Pro  Cys  Ala  Gly  Lys  Leu  Asn
     1710                1715                1720

GGG  CAG  CTG  GTC  CAG  CCG  GGA  ATG  CCC  ATC  AAC  CAG  GCA  CCT  CCT  GCC   5295
Gly  Gln  Leu  Val  Gln  Pro  Gly  Met  Pro  Ile  Asn  Gln  Ala  Pro  Pro  Ala
1725                1730                1735
```

-continued

| CCC | TGC | CAG | CAG | CCT | AGC | ACA | GAT | CCC | CCA | GAG | CGC | GGG | CAG | AGG | AGG | 5343 |
| Pro | Cys | Gln | Gln | Pro | Ser | Thr | Asp | Pro | Pro | Glu | Arg | Gly | Gln | Arg | Arg | |
| 1740 | | | | 1745 | | | | | 1750 | | | | | 1755 | | |

| ACC | TCC | CTG | ACA | GGG | TCT | CTG | CAA | GAC | GAA | GCA | CCC | CAG | AGG | AGG | AGC | 5391 |
| Thr | Ser | Leu | Thr | Gly | Ser | Leu | Gln | Asp | Glu | Ala | Pro | Gln | Arg | Arg | Ser | |
| | | | | 1760 | | | | | 1765 | | | | | 1770 | | |

| TCC | GAG | GGG | AGC | ACC | CCC | AGG | CGC | CCG | GCT | CCT | GCT | ACA | GCT | CTG | CTG | 5439 |
| Ser | Glu | Gly | Ser | Thr | Pro | Arg | Arg | Pro | Ala | Pro | Ala | Thr | Ala | Leu | Leu | |
| | | | 1775 | | | | | 1780 | | | | | 1785 | | | |

| ATC | CAA | GAG | GCT | CTG | GTT | CGA | GGG | GGC | CTG | GAC | ACC | TTG | GCA | GCT | GAT | 5487 |
| Ile | Gln | Glu | Ala | Leu | Val | Arg | Gly | Gly | Leu | Asp | Thr | Leu | Ala | Ala | Asp | |
| | | 1790 | | | | | 1795 | | | | | 1800 | | | | |

| GCT | GGC | TTC | GTC | ATG | GCA | ACA | AGC | CAG | GCC | CTG | GTA | GAC | GCC | TGT | CAG | 5535 |
| Ala | Gly | Phe | Val | Met | Ala | Thr | Ser | Gln | Ala | Leu | Val | Asp | Ala | Cys | Gln | |
| | 1805 | | | | | 1810 | | | | | 1815 | | | | | |

| ATG | GAA | CCG | GAG | GAA | GTA | GAG | GTC | GCA | GCC | ACA | GAG | CTA | CTG | AAA | GAG | 5583 |
| Met | Glu | Pro | Glu | Glu | Val | Glu | Val | Ala | Ala | Thr | Glu | Leu | Leu | Lys | Glu | |
| 1820 | | | | 1825 | | | | | 1830 | | | | | 1835 | | |

| CGA | GAG | TCC | GTC | CAG | GGC | ATG | GCC | AGT | GTC | CCG | GGA | AGC | CTG | AGC | CGC | 5631 |
| Arg | Glu | Ser | Val | Gln | Gly | Met | Ala | Ser | Val | Pro | Gly | Ser | Leu | Ser | Arg | |
| | | | | 1840 | | | | | 1845 | | | | | 1850 | | |

| AGG | TCC | TCC | CTG | GGC | AGC | CTT | GAC | CAG | GTC | CAG | GGC | TCC | CAG | GAA | ACC | 5679 |
| Arg | Ser | Ser | Leu | Gly | Ser | Leu | Asp | Gln | Val | Gln | Gly | Ser | Gln | Glu | Thr | |
| | | | 1855 | | | | | 1860 | | | | | 1865 | | | |

| CTT | ATT | CCT | CCC | AGG | CCG | TGA | TGGCTGTGCA | GTGTCCACAT | GACCAAGGCG | AGGGG | 5735 |
| Leu | Ile | Pro | Pro | Arg | Pro | * | | | | | |
| | 1870 | | | | | | | | | | |

| GACAGTGCGT | GCAGAAGCTC | AGCCCTGCAT | GGCAGCCTCC | CTCTGTCTCA | GCCCTCCTGC | 5795 |
| TGAGCTGGGG | CGGTCTGGAA | CCGACCAGGA | AGCCAGGAGC | CTCCCCTGGC | CAGCAAGAGG | 5855 |
| CATGATTCTA | AAGCATCCAG | AAAGGCCTGG | TCAGTGCCAC | TCCCCAGCAG | GACATTAAAG | 5915 |
| TCTCTAGGTC | TGTGGCAAAA | AAAAAAAAAA | AAAAAAAAAA | AAAAAAAAAA | AAAAAAAAAA | 5975 |

( 2 ) INFORMATION FOR SEQ ID NO:4:

( i ) SEQUENCE CHARACTERISTICS:
        ( A ) LENGTH: 3802 base pairs
        ( B ) TYPE: nucleic acid
        ( C ) STRANDEDNESS: Not Relevant
        ( D ) TOPOLOGY: Not Relevant ( i i ) MOLECULE TYPE: Genomic DNA ( i x ) FEATURE:
        ( A ) NAME/KEY: Coding Sequence
        ( B ) LOCATION: 309...3629
        ( D ) OTHER INFORMATION: product="Alpha-2 subunit of animal ca
        channel"

( x i ) SEQUENCE DESCRIPTION: SEQ ID NO:4:

| AGAAGGGAGG | GCGAGCGTGG | TGTGTGCGCG | CTCGGGCGCC | GGCGGCACCG | CCGAGGTCTG | 60 |
| TTGGCAAAAG | TCGCCCTTGA | TGGCGGCGGA | GGCGAGGCAG | CCGCGGCGCC | GAACAGCCGA | 120 |
| CGCGCGCTAG | CGGGGTCCGC | CCGCCCCTTT | CCCAGAGCCC | AGCGCCGCCG | TTCGCCGCCG | 180 |
| CCGCCGCCCG | CCCGCGCGCC | GTTCGCCGCC | GCCGCCGCCC | GCGGGTGGCA | GCGCCGCTCG | 240 |
| GTCCCCGGCC | CCGGGGCCGG | CTGGGGGGCG | GTCGGGGCGT | GTGAGGGGCT | TGCTCCCAGC | 300 |

| TCGCGAAG | ATG | GCT | GCG | GGC | CGC | CCG | CTG | GCC | TGG | ACG | CTG | ACA | CTT | TGG | 350 |
| | Met | Ala | Ala | Gly | Arg | Pro | Leu | Ala | Trp | Thr | Leu | Thr | Leu | Trp | |
| | 1 | | | | 5 | | | | | 10 | | | | | |

| CAG | GCG | TGG | CTG | ATC | CTG | ATC | GGG | CCC | TCG | TCG | GAG | GAG | CCG | TTC | CCT | 398 |
| Gln | Ala | Trp | Leu | Ile | Leu | Ile | Gly | Pro | Ser | Ser | Glu | Glu | Pro | Phe | Pro | |
| 15 | | | | 20 | | | | | 25 | | | | | 30 | | |

| | | | | | | | | | | | | | | | | |
|---|---|---|---|---|---|---|---|---|---|---|---|---|---|---|---|---|
| TCA | GCC | GTC | ACT | ATC | AAG | TCA | TGG | GTG | GAT | AAG | ATG | CAA | GAA | GAC | CTG | 446 |
| Ser | Ala | Val | Thr | Ile 35 | Lys | Ser | Trp | Val 40 | Asp | Lys | Met | Gln | Glu | Asp 45 | Leu | |
| GTC | ACA | CTA | GCA | AAA | ACA | GCA | AGT | GGA | GTC | CAT | CAG | CTT | GTT | GAT | ATT | 494 |
| Val | Thr | Leu | Ala 50 | Lys | Thr | Ala | Ser | Gly 55 | Val | His | Gln | Leu | Val 60 | Asp | Ile | |
| TAT | GAG | AAA | TAT | CAA | GAT | TTG | TAT | ACT | GTG | GAA | CCA | AAT | AAT | GCA | CGT | 542 |
| Tyr | Glu | Lys 65 | Tyr | Gln | Asp | Leu | Tyr 70 | Thr | Val | Glu | Pro | Asn 75 | Asn | Ala | Arg | |
| CAG | CTG | GTG | GAA | ATT | GCA | GCC | AGA | GAC | ATT | GAG | AAG | CTT | CTC | AGC | AAC | 590 |
| Gln | Leu 80 | Val | Glu | Ile | Ala | Ala 85 | Arg | Asp | Ile | Glu | Lys 90 | Leu | Leu | Ser | Asn | |
| AGA | TCT | AAA | GCC | CTG | GTG | CGC | CTG | GCT | TTG | GAA | GCA | GAG | AAA | GTT | CAA | 638 |
| Arg 95 | Ser | Lys | Ala | Leu | Val 100 | Arg | Leu | Ala | Leu | Glu 105 | Ala | Glu | Lys | Val | Gln 110 | |
| GCA | GCC | CAC | CAA | TGG | AGG | GAA | GAT | TTT | GCA | AGC | AAT | GAA | GTT | GTC | TAC | 686 |
| Ala | Ala | His | Gln | Trp 115 | Arg | Glu | Asp | Phe | Ala 120 | Ser | Asn | Glu | Val | Val 125 | Tyr | |
| TAT | AAC | GCG | AAG | GAT | GAT | CTT | GAT | CCT | GAA | AAA | AAT | GAG | AGT | GAA | CCA | 734 |
| Tyr | Asn | Ala | Lys 130 | Asp | Asp | Leu | Asp | Pro 135 | Glu | Lys | Asn | Glu | Ser 140 | Glu | Pro | |
| GGC | AGC | CAG | AGG | ATC | AAA | CCT | GTT | TTC | ATT | GAC | GAT | GCT | AAC | TTT | AGA | 782 |
| Gly | Ser | Gln | Arg 145 | Ile | Lys | Pro | Val | Phe 150 | Ile | Asp | Asp | Ala | Asn 155 | Phe | Arg | |
| AGA | CAA | GTA | TCC | TAT | CAG | CAC | GCA | GCT | GTC | CAT | ATC | CCC | ACT | GAC | ATC | 830 |
| Arg | Gln 160 | Val | Ser | Tyr | Gln | His 165 | Ala | Ala | Val | His | Ile 170 | Pro | Thr | Asp | Ile | |
| TAT | GAA | GGA | TCG | ACA | ATC | GTG | TTA | AAC | GAA | CTC | AAC | TGG | ACA | AGT | GCC | 878 |
| Tyr 175 | Glu | Gly | Ser | Thr | Ile 180 | Val | Leu | Asn | Glu | Leu 185 | Asn | Trp | Thr | Ser | Ala 190 | |
| TTA | GAT | GAC | GTT | TTC | AAA | AAA | AAT | CGA | GAG | GAA | GAC | CCT | TCA | CTG | TTG | 926 |
| Leu | Asp | Asp | Val | Phe 195 | Lys | Lys | Asn | Arg | Glu 200 | Glu | Asp | Pro | Ser | Leu 205 | Leu | |
| TGG | CAG | GTG | TTT | GGC | AGT | GCC | ACT | GGC | CTG | GCC | CGG | TAT | TAC | CCA | GCT | 974 |
| Trp | Gln | Val | Phe 210 | Gly | Ser | Ala | Thr | Gly 215 | Leu | Ala | Arg | Tyr | Tyr 220 | Pro | Ala | |
| TCT | CCA | TGG | GTT | GAT | AAT | AGC | CGA | ACC | CCA | AAC | AAG | ATT | GAT | CTT | TAT | 1022 |
| Ser | Pro | Trp 225 | Val | Asp | Asn | Ser | Arg 230 | Thr | Pro | Asn | Lys | Ile 235 | Asp | Leu | Tyr | |
| GAT | GTA | CGC | AGA | AGA | CCA | TGG | TAC | ATC | CAA | GGT | GCT | GCA | TCC | CCT | AAA | 1070 |
| Asp | Val | Arg 240 | Arg | Arg | Pro | Trp | Tyr 245 | Ile | Gln | Gly | Ala | Ala 250 | Ser | Pro | Lys | |
| GAT | ATG | CTT | ATT | CTG | GTG | GAT | GTG | AGT | GGA | AGC | GTT | AGT | GGA | CTG | ACA | 1118 |
| Asp | Met | Leu | Ile 255 | Leu | Val | Asp | Val | Ser 260 | Gly | Ser | Val | Ser | Gly 265 | Leu | Thr 270 | |
| CTA | AAA | CTC | ATC | CGG | ACA | TCC | GTC | TCC | GAA | ATG | TTG | AAA | ACC | CTC | TCA | 1166 |
| Leu | Lys | Leu | Ile | Arg 275 | Thr | Ser | Val | Ser | Glu 280 | Met | Leu | Glu | Thr | Leu 285 | Ser | |
| GAT | GAT | GAT | TTT | GTG | AAC | GTG | GCT | TCA | TTT | AAC | AGC | AAT | GCT | CAG | GAT | 1214 |
| Asp | Asp | Asp | Phe 290 | Val | Asn | Val | Ala | Ser 295 | Phe | Asn | Ser | Asn | Ala 300 | Gln | Asp | |
| GTA | AGC | TGC | TTT | CAG | CAC | CTT | GTC | CAA | GCA | AAT | GTA | AGA | AAT | AAG | AAA | 1262 |
| Val | Ser | Cys 305 | Phe | Gln | His | Leu | Val 310 | Gln | Ala | Asn | Val | Arg 315 | Asn | Lys | Lys | |
| GTG | TTG | AAA | GAT | GCA | GTG | AAT | AAT | ATC | ACA | GCA | AAA | GGA | ATC | ACA | GAT | 1310 |
| Val | Leu | Lys | Asp 320 | Ala | Val | Asn | Asn | Ile 325 | Thr | Ala | Lys | Gly | Ile 330 | Thr | Asp | |
| TAT | AAG | AAG | GGC | TTT | AGT | TTT | GCT | TTT | GAG | CAG | CTG | CTT | AAT | TAT | AAT | 1358 |
| Tyr | Lys | Lys 335 | Gly | Phe | Ser | Phe 340 | Ala | Phe | Glu | Gln | Leu 345 | Leu | Asn | Tyr | Asn 350 | |

```
GTA TCC AGA GCC AAC TGC AAT AAG ATT ATC ATG TTG TTC ACG GAC GGA    1406
Val Ser Arg Ala Asn Cys Asn Lys Ile Ile Met Leu Phe Thr Asp Gly
            355                 360                 365

GGA GAA GAG AGA GCC CAG GAG ATA TTT GCC AAA TAC AAT AAA GAC AAG    1454
Gly Glu Glu Arg Ala Gln Glu Ile Phe Ala Lys Tyr Asn Lys Asp Lys
            370                 375                 380

AAA GTA CGT GTA TTC ACA TTC TCA GTT GGC CAA CAT AAT TAC GAC AGA    1502
Lys Val Arg Val Phe Thr Phe Ser Val Gly Gln His Asn Tyr Asp Arg
            385                 390                 395

GGA CCT ATT CAG TGG ATG GCT TGC GAA AAT AAA GGT TAT TAT TAT GAA    1550
Gly Pro Ile Gln Trp Met Ala Cys Glu Asn Lys Gly Tyr Tyr Tyr Glu
            400                 405                 410

ATT CCA TCC ATT GGA GCC ATA AGA ATT AAT ACT CAG GAA TAC CTA GAT    1598
Ile Pro Ser Ile Gly Ala Ile Arg Ile Asn Thr Gln Glu Tyr Leu Asp
415                 420                 425                 430

GTT CTG GGA AGA CCG ATG GTT TTA GCA GGA GAC AAA GCT AAG CAA GTC    1646
Val Leu Gly Arg Pro Met Val Leu Ala Gly Asp Lys Ala Lys Gln Val
            435                 440                 445

CAA TGG ACA AAT GTG TAC CTG GAT GCA CTG GAA CTG GGA CTT GTC ATT    1694
Gln Trp Thr Asn Val Tyr Leu Asp Ala Leu Glu Leu Gly Leu Val Ile
            450                 455                 460

ACT GGA ACT CTT CCG GTC TTC AAC ATA ACT GGC CAA TTT GAA AAT AAG    1742
Thr Gly Thr Leu Pro Val Phe Asn Ile Thr Gly Gln Phe Glu Asn Lys
            465                 470                 475

ACA AAC TTA AAG AAC CAG CTG ATT CTT GGA GTG ATG GGA GTT GAT GTG    1790
Thr Asn Leu Lys Asn Gln Leu Ile Leu Gly Val Met Gly Val Asp Val
            480                 485                 490

TCT TTG GAA GAT ATT AAA AGA CTG ACA CCA CGT TTT ACA CTC TGC CCC    1838
Ser Leu Glu Asp Ile Lys Arg Leu Thr Pro Arg Phe Thr Leu Cys Pro
495                 500                 505                 510

AAT GGC TAC TAT TTT GCA ATT GAT CCT AAT GGT TAT GTG TTA TTA CAT    1886
Asn Gly Tyr Tyr Phe Ala Ile Asp Pro Asn Gly Tyr Val Leu Leu His
            515                 520                 525

CCA AAT CTT CAG CCA AAG CCT ATT GGT GTA GGT ATA CCA ACA ATT AAT    1934
Pro Asn Leu Gln Pro Lys Pro Ile Gly Val Gly Ile Pro Thr Ile Asn
            530                 535                 540

TTG AGA AAA AGG AGA CCC AAT GTT CAG AAC CCC AAA TCT CAG GAG CCA    1982
Leu Arg Lys Arg Arg Pro Asn Val Gln Asn Pro Lys Ser Gln Glu Pro
            545                 550                 555

GTG ACA TTG GAT TTC CTC GAT GCA GAG TTG GAG AAT GAC ATT AAA GTG    2030
Val Thr Leu Asp Phe Leu Asp Ala Glu Leu Glu Asn Asp Ile Lys Val
            560                 565                 570

GAG ATT CGA AAT AAA ATG ATC GAT GGA GAA AGT GGA GAA AAA ACA TTC    2078
Glu Ile Arg Asn Lys Met Ile Asp Gly Glu Ser Gly Glu Lys Thr Phe
575                 580                 585                 590

AGA ACT CTG GTT AAA TCT CAA GAT GAG AGA TAT ATT GAC AAA GGA AAC    2126
Arg Thr Leu Val Lys Ser Gln Asp Glu Arg Tyr Ile Asp Lys Gly Asn
            595                 600                 605

AGG ACA TAC ACG TGG ACT CCT GTC AAC GGC ACA GAT TAT AGC AGT TTG    2174
Arg Thr Tyr Thr Trp Thr Pro Val Asn Gly Thr Asp Tyr Ser Ser Leu
            610                 615                 620

GCC TTG GTA TTA CCA ACC TAC AGT TTT TAC TAT ATA AAA GCC AAA ATA    2222
Ala Leu Val Leu Pro Thr Tyr Ser Phe Tyr Tyr Ile Lys Ala Lys Ile
            625                 630                 635

GAA GAG ACA ATA ACT CAG GCC AGA TAT TCA GAA ACA CTG AAA CCG GAT    2270
Glu Glu Thr Ile Thr Gln Ala Arg Tyr Ser Glu Thr Leu Lys Pro Asp
            640                 645                 650

AAT TTT GAA GAA TCC GGC TAC ACA TTC CTA GCA CCA AGA GAT TAC TGC    2318
Asn Phe Glu Glu Ser Gly Tyr Thr Phe Leu Ala Pro Arg Asp Tyr Cys
655                 660                 665                 670
```

```
AGT GAC CTT AAA CCT TCA GAT AAT AAC ACT GAA TTT CTT TTA AAT TTC    2366
Ser Asp Leu Lys Pro Ser Asp Asn Asn Thr Glu Phe Leu Leu Asn Phe
            675             680                 685

AAT GAG TTT ATT GAT AGA AAA ACT CCA AAC AAC CCA TCC TGT AAT ACA    2414
Asn Glu Phe Ile Asp Arg Lys Thr Pro Asn Asn Pro Ser Cys Asn Thr
            690             695             700

GAC TTG ATT AAT AGA GTC TTG CTG GAT GCA GGC TTT ACA AAT GAA CTT    2462
Asp Leu Ile Asn Arg Val Leu Leu Asp Ala Gly Phe Thr Asn Glu Leu
        705             710             715

GTT CAA AAT TAC TGG AGT AAG CAG AAG AAT ATC AAG GGA GTG AAA GCA    2510
Val Gln Asn Tyr Trp Ser Lys Gln Lys Asn Ile Lys Gly Val Lys Ala
    720             725             730

CGG TTT GTT GTG ACT GAT GGT GGG ATT ACC AGA GTT TAT CCC AAA GAG    2558
Arg Phe Val Val Thr Asp Gly Gly Ile Thr Arg Val Tyr Pro Lys Glu
735             740             745             750

GCT GGA GAA AAT TGG CAG GAA AAC CCA GAG ACA TAT GAA GAC AGC TTC    2606
Ala Gly Glu Asn Trp Gln Glu Asn Pro Glu Thr Tyr Glu Asp Ser Phe
            755             760             765

TAT AAA AGG AGC CTC GAT AAT GAT AAC TAC GTT TTC ACT GCT CCC TAC    2654
Tyr Lys Arg Ser Leu Asp Asn Asp Asn Tyr Val Phe Thr Ala Pro Tyr
            770             775             780

TTT AAC AAA AGT GGA CCT GGG GCC TAT GAG TCA GGC ATT ATG GTA AGC    2702
Phe Asn Lys Ser Gly Pro Gly Ala Tyr Glu Ser Gly Ile Met Val Ser
            785             790             795

AAA GCT GTA GAA ATA TAT ATC CAA GGA AAA CTT CTT AAA CCT GCA GTT    2750
Lys Ala Val Glu Ile Tyr Ile Gln Gly Lys Leu Leu Lys Pro Ala Val
800             805             810

GTT GGA ATT AAA ATT GAT GTA AAT TCT TGG ATA GAG AAT TTC ACC AAA    2798
Val Gly Ile Lys Ile Asp Val Asn Ser Trp Ile Glu Asn Phe Thr Lys
815             820             825             830

ACT TCA ATC AGG GAT CCG TGT GCT GGT CCA GTT TGT GAC TGC AAA CGA    2846
Thr Ser Ile Arg Asp Pro Cys Ala Gly Pro Val Cys Asp Cys Lys Arg
            835             840             845

AAC AGT GAT GTA ATG GAT TGT GTG ATT CTA GAT GAC GGT GGG TTT CTT    2894
Asn Ser Asp Val Met Asp Cys Val Ile Leu Asp Asp Gly Gly Phe Leu
            850             855             860

TTG ATG GCC AAC CAT GAT GAT TAT ACC AAT CAG ATT GGA AGA TTC TTT    2942
Leu Met Ala Asn His Asp Asp Tyr Thr Asn Gln Ile Gly Arg Phe Phe
            865             870             875

GGA GAG ATT GAT CCA AGC TTG ATG AGA CAC CTG GTC AAT ATA TCA GTT    2990
Gly Glu Ile Asp Pro Ser Leu Met Arg His Leu Val Asn Ile Ser Val
880             885             890

TAT GCC TTT AAC AAA TCT TAT GAT TAT CAG TCG GTG TGT GAA CCT GGT    3038
Tyr Ala Phe Asn Lys Ser Tyr Asp Tyr Gln Ser Val Cys Glu Pro Gly
895             900             905             910

GCT GCG CCA AAC CAG GGA GCA GGG CAC CGC TCG GCT TAT GTG CCA TCA    3086
Ala Ala Pro Asn Gln Gly Ala Gly His Arg Ser Ala Tyr Val Pro Ser
            915             920             925

ATA GCA GAC ATA CTG CAG ATT GGA TGG TGG GCC ACT GCT GCT GCC TGG    3134
Ile Ala Asp Ile Leu Gln Ile Gly Trp Trp Ala Thr Ala Ala Ala Trp
            930             935             940

TCT ATT CTT CAG CAG TTT CTG TTG AGT TTG ACT TTT CCA CGG CTC CTT    3182
Ser Ile Leu Gln Gln Phe Leu Leu Ser Leu Thr Phe Pro Arg Leu Leu
            945             950             955

GAG GCA GCT GAT ATG GAG GAT GAC GAC TTC ACT GCC TCC ATG TCA AAG    3230
Glu Ala Ala Asp Met Glu Asp Asp Asp Phe Thr Ala Ser Met Ser Lys
            960             965             970

CAG AGC TGC ATC ACT GAG CAA ACC CAG TAT TTC TTC GAT AAT GAC AGC    3278
Gln Ser Cys Ile Thr Glu Gln Thr Gln Tyr Phe Phe Asp Asn Asp Ser
975             980             985             990
```

```
AAA  TCG  TTC  AGT  GGG  GTA  TTA  GAC  TGT  GGG  AAT  TGT  TCC  AGA  ATC  TTT       3326
Lys  Ser  Phe  Ser  Gly  Val  Leu  Asp  Cys  Gly  Asn  Cys  Ser  Arg  Ile  Phe
               995                      1000                     1005

CAT  GTA  GAA  AAG  CTC  ATC  AAC  ACC  AAT  TTA  ATA  TTC  ATA  ATG  GTA  GAG       3374
His  Val  Glu  Lys  Leu  Ile  Asn  Thr  Asn  Leu  Ile  Phe  Ile  Met  Val  Glu
               1010                     1015                     1020

AGC  AAG  GGG  ACA  TGT  CCC  TGT  GAC  ACA  CGG  CTG  CTC  ATA  CAA  GCA  GAG       3422
Ser  Lys  Gly  Thr  Cys  Pro  Cys  Asp  Thr  Arg  Leu  Leu  Ile  Gln  Ala  Glu
               1025                     1030                     1035

CAA  ACT  TCT  GAT  GGA  CCA  GAT  CCT  TGT  GAT  ATG  GTT  AAG  CAA  CCC  AGA       3470
Gln  Thr  Ser  Asp  Gly  Pro  Asp  Pro  Cys  Asp  Met  Val  Lys  Gln  Pro  Arg
      1040                     1045                     1050

TAT  CGA  AAA  GGG  CCA  GAT  GTC  TGC  TTT  GAC  AAC  AAT  GTC  CTG  GAG  GAT       3518
Tyr  Arg  Lys  Gly  Pro  Asp  Val  Cys  Phe  Asp  Asn  Asn  Val  Leu  Glu  Asp
1055                     1060                     1065                     1070

TAT  ACT  GAC  TGC  GGT  GGG  GTC  TCT  GGA  TTA  AAT  CCT  TCC  CTG  TGG  TCC       3566
Tyr  Thr  Asp  Cys  Gly  Gly  Val  Ser  Gly  Leu  Asn  Pro  Ser  Leu  Trp  Ser
               1075                     1080                     1085

ATC  ATC  GGG  ATA  CAG  TTT  GTA  CTG  CTT  TGG  CTG  GTT  TCT  GGC  AGC  AGA       3614
Ile  Ile  Gly  Ile  Gln  Phe  Val  Leu  Leu  Trp  Leu  Val  Ser  Gly  Ser  Arg
               1090                     1095                     1100

CAC  TGC  CTG  TTA  TGA  CCTTCTAAAA  CCAAATCTCC  ATAATTAAAC  TCCAGACCCT  GC          3671
His  Cys  Leu  Leu   *
               1105

CACAACATGA  TCCCTCCGTT  ATGTTAAAGT  AGGGTCAACT  GTTAAATCAG  AACATTAGCT               3731

GGGCCTCTGC  CATGGCAGAG  CCCTAAGGCG  CAGACTCATC  AGGCACCCAC  TGGCTGCATG               3791

TCAGGGTCTC  C                                                                        3802
```

( 2 ) INFORMATION FOR SEQ ID NO:5:

( i ) SEQUENCE CHARACTERISTICS:
        ( A ) LENGTH: 222 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( v i ) ORIGINAL SOURCE:

( x i ) SEQUENCE DESCRIPTION: SEQ ID NO:5:

```
Met  Ser  Pro  Thr  Glu  Ala  Pro  Lys  Val  Arg  Val  Thr  Leu  Phe  Cys  Ile
 1              5                        10                       15

Leu  Val  Gly  Ile  Val  Leu  Ala  Met  Thr  Ala  Val  Val  Ser  Asp  His  Trp
               20                       25                       30

Ala  Val  Leu  Ser  Pro  His  Met  Glu  Asn  His  Asn  Thr  Thr  Cys  Glu  Ala
               35                       40                       45

Ala  His  Phe  Gly  Leu  Trp  Arg  Ile  Cys  Thr  Lys  Arg  Ile  Ala  Leu  Gly
      50                       55                       60

Glu  Asp  Arg  Ser  Cys  Gly  Pro  Ile  Thr  Leu  Pro  Gly  Glu  Lys  Asn  Cys
 65                       70                       75                       80

Ser  Tyr  Phe  Arg  His  Phe  Asn  Pro  Gly  Glu  Ser  Ser  Glu  Ile  Phe  Glu
                    85                       90                       95

Phe  Thr  Thr  Gln  Lys  Glu  Tyr  Ser  Ile  Ser  Ala  Ala  Ile  Ser  Val
                    100                      105                      110

Phe  Ser  Leu  Gly  Phe  Leu  Ile  Met  Gly  Thr  Ile  Cys  Ala  Leu  Met  Ala
               115                      120                      125
```

```
Phe  Arg  Lys  Lys  Arg  Asp  Tyr  Leu  Leu  Arg  Pro  Ala  Ser  Met  Phe  Tyr
     130                      135                      140

Val  Phe  Ala  Gly  Leu  Cys  Leu  Phe  Val  Ser  Leu  Glu  Val  Met  Arg  Gln
145                      150                      155                      160

Ser  Val  Lys  Arg  Met  Ile  Asp  Ser  Glu  Asp  Thr  Val  Trp  Ile  Glu  Tyr
               165                      170                      175

Tyr  Tyr  Ser  Trp  Ser  Phe  Ala  Cys  Ala  Cys  Ala  Ala  Phe  Val  Leu  Leu
               180                      185                      190

Phe  Leu  Gly  Gly  Ile  Ser  Leu  Leu  Leu  Phe  Ser  Leu  Pro  Arg  Met  Pro
          195                      200                      205

Gln  Asn  Pro  Trp  Glu  Ser  Cys  Met  Asp  Ala  Glu  Pro  Glu  His
     210                      215                      220
```

( 2 ) INFORMATION FOR SEQ ID NO:6:

( i ) SEQUENCE CHARACTERISTICS:
        ( A ) LENGTH: 524 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( v i ) ORIGINAL SOURCE:

( x i ) SEQUENCE DESCRIPTION: SEQ ID NO:6:

```
Met  Val  Gln  Lys  Thr  Ser  Met  Ser  Arg  Gly  Pro  Tyr  Pro  Pro  Ser  Gln
1                    5                    10                       15

Glu  Ile  Pro  Met  Glu  Val  Phe  Asp  Pro  Ser  Pro  Gln  Gly  Lys  Tyr  Ser
               20                       25                       30

Lys  Arg  Lys  Gly  Arg  Phe  Lys  Arg  Ser  Asp  Gly  Ser  Thr  Ser  Ser  Asp
          35                       40                       45

Thr  Thr  Ser  Asn  Ser  Phe  Val  Arg  Gln  Gly  Ser  Ala  Glu  Ser  Tyr  Thr
     50                       55                       60

Ser  Arg  Pro  Ser  Asp  Ser  Asp  Val  Ser  Leu  Glu  Glu  Asp  Arg  Glu  Ala
65                       70                       75                       80

Leu  Arg  Lys  Glu  Ala  Glu  Arg  Gln  Ala  Leu  Ala  Gln  Leu  Glu  Lys  Ala
               85                       90                       95

Lys  Thr  Lys  Pro  Val  Ala  Phe  Ala  Val  Arg  Thr  Asn  Val  Gly  Tyr  Asn
               100                      105                      110

Pro  Ser  Pro  Gly  Asp  Glu  Val  Pro  Val  Glu  Gly  Val  Ala  Ile  Thr  Phe
          115                      120                      125

Glu  Pro  Lys  Asp  Phe  Leu  His  Ile  Lys  Glu  Lys  Tyr  Asn  Asn  Asp  Trp
     130                      135                      140

Trp  Ile  Gly  Arg  Leu  Val  Lys  Glu  Gly  Cys  Glu  Val  Gly  Phe  Ile  Pro
145                      150                      155                      160

Ser  Pro  Val  Lys  Leu  Asp  Ser  Leu  Arg  Leu  Leu  Gln  Glu  Gln  Lys  Leu
               165                      170                      175

Leu  Gln  Ser  Arg  Leu  Ser  Ser  Ser  Lys  Ser  Gly  Asp  Asn  Ser  Ser  Ser
               180                      185                      190

Ser  Leu  Gly  Asp  Val  Val  Thr  Gly  Thr  Arg  Arg  Pro  Thr  Pro  Pro  Ala
          195                      200                      205

Ser  Gly  Asn  Glu  Met  Thr  Asn  Leu  Ala  Phe  Glu  Leu  Glu  Pro  Leu  Asp
     210                      215                      220

Leu  Glu  Glu  Asp  Glu  Ala  Glu  Leu  Gly  Glu  Gln  Ser  Gly  Ser  Ala  Lys
225                      230                      235                      240
```

-continued

| Thr | Ser | Val | Ser | Ser 245 | Val | Thr | Thr | Pro | Pro 250 | Pro | His | Gly | Thr | Arg 255 | Ile |
| Pro | Phe | Phe | Lys 260 | Lys | Thr | Glu | His | Val 265 | Pro | Pro | Tyr | Asp | Val 270 | Val | Pro |
| Ser | Met | Arg 275 | Pro | Ile | Ile | Leu | Val 280 | Gly | Pro | Ser | Leu | Lys 285 | Gly | Tyr | Glu |
| Val | Thr 290 | Asp | Met | Met | Gln 295 | Lys | Ala | Leu | Phe | Asp 300 | Phe | Leu | Lys | His | Arg |
| Phe 305 | Asp | Gly | Arg | Ile | Ser 310 | Ile | Thr | Arg | Val | Thr 315 | Ala | Asp | Ile | Ser | Leu 320 |
| Ala | Lys | Arg | Ser | Val 325 | Leu | Asn | Asn | Pro | Ser 330 | Lys | His | Ile | Ile | Ile 335 | Glu |
| Arg | Ser | Asn | Thr 340 | Arg | Ser | Ser | Leu | Ala 345 | Glu | Val | Gln | Ser | Glu 350 | Ile | Glu |
| Arg | Ile | Phe 355 | Glu | Leu | Ala | Arg | Thr 360 | Leu | Gln | Leu | Val | Ala 365 | Leu | Asp | Ala |
| Asp | Thr 370 | Ile | Asn | His | Pro | Ala 375 | Gln | Leu | Ser | Lys | Thr 380 | Ser | Leu | Ala | Pro |
| Ile 385 | Ile | Val | Tyr | Ile | Lys 390 | Ile | Thr | Ser | Pro | Lys 395 | Val | Leu | Gln | Arg | Leu 400 |
| Ile | Lys | Ser | Arg | Gly 405 | Lys | Ser | Gln | Ser | Lys 410 | His | Leu | Asn | Val | Gln 415 | Ile |
| Ala | Ala | Ser | Glu 420 | Lys | Leu | Ala | Gln | Cys 425 | Pro | Pro | Glu | Met | Phe 430 | Asp | Ile |
| Ile | Leu | Asp 435 | Glu | Asn | Gln | Leu | Glu 440 | Asp | Ala | Cys | Glu | His 445 | Leu | Ala | Glu |
| Tyr | Leu 450 | Glu | Ala | Tyr | Trp | Lys 455 | Ala | Thr | His | Pro | Pro 460 | Ser | Ser | Thr | Pro |
| Pro 465 | Asn | Pro | Leu | Leu | Asn 470 | Arg | Thr | Met | Ala | Thr 475 | Ala | Ala | Leu | Ala | Ala 480 |
| Ser | Pro | Ala | Pro | Val 485 | Ser | Asn | Leu | Gln | Val 490 | Gln | Val | Leu | Thr | Ser 495 | Leu |
| Arg | Arg | Asn | Leu 500 | Ser | Phe | Trp | Gly | Gly 505 | Leu | Glu | Thr | Ser | Gln 510 | Arg | Gly |
| Gly | Gly | Ala 515 | Val | Pro | Gln | Gln | Gln 520 | Glu | His | Ala | Met | | | | |

(2) INFORMATION FOR SEQ ID NO:7:

(i) SEQUENCE CHARACTERISTICS:
        (A) LENGTH: 1873 amino acids
        (B) TYPE: amino acid
        (C) STRANDEDNESS: single
        (D) TOPOLOGY: linear (ii) MOLECULE TYPE: protein (v) FRAGMENT TYPE: internal (vi) ORIGINAL SOURCE:

(xi) SEQUENCE DESCRIPTION: SEQ ID NO:7:

| Met 1 | Glu | Pro | Ser | Ser 5 | Pro | Gln | Asp | Glu | Gly 10 | Leu | Arg | Lys | Lys | Gln 15 | Pro |
| Lys | Lys | Pro | Leu 20 | Pro | Glu | Val | Leu | Pro 25 | Arg | Pro | Pro | Arg | Ala 30 | Leu | Phe |
| Cys | Leu | Thr 35 | Leu | Gln | Asn | Pro | Leu 40 | Arg | Lys | Ala | Cys | Ile 45 | Ser | Ile | Val |

-continued

| | | | | | | | | | | | | | | |
|---|---|---|---|---|---|---|---|---|---|---|---|---|---|---|
| Glu | Trp 50 | Lys | Pro | Phe | Glu 55 | Thr | Ile | Leu | Leu | Thr 60 | Ile | Phe | Ala | Asn |
| Cys 65 | Val | Ala | Leu | Ala | Val 70 | Tyr | Leu | Pro | Met | Pro 75 | Glu | Asp | Asp | Asn 80 |
| Ser | Leu | Asn | Leu | Gly 85 | Leu | Glu | Lys | Leu | Glu 90 | Tyr | Phe | Phe | Leu | Thr 95 | Val |
| Phe | Ser | Ile | Glu 100 | Ala | Ala | Met | Lys | Ile 105 | Ile | Ala | Tyr | Gly | Phe 110 | Leu | Phe |
| His | Gln | Asp 115 | Ala | Tyr | Leu | Arg | Ser 120 | Gly | Trp | Asn | Val | Leu 125 | Asp | Phe | Ile |
| Ile | Val 130 | Phe | Leu | Gly | Val | Phe 135 | Thr | Ala | Ile | Leu | Glu 140 | Gln | Val | Asn | Val |
| Ile 145 | Gln | Ser | Asn | Thr | Ala 150 | Pro | Met | Ser | Ser | Lys 155 | Gly | Ala | Gly | Leu | Asp 160 |
| Val | Lys | Ala | Leu | Arg 165 | Ala | Phe | Arg | Val | Leu 170 | Arg | Pro | Leu | Arg | Leu 175 | Val |
| Ser | Gly | Val | Pro 180 | Ser | Leu | Gln | Val | Val 185 | Leu | Asn | Ser | Ile | Phe 190 | Lys | Ala |
| Met | Leu | Pro 195 | Leu | Phe | His | Ile | Ala 200 | Leu | Leu | Val | Leu | Phe 205 | Met | Val | Ile |
| Ile | Tyr 210 | Ala | Ile | Ile | Gly | Leu 215 | Glu | Leu | Phe | Lys | Gly 220 | Lys | Met | His | Lys |
| Thr 225 | Cys | Tyr | Tyr | Ile | Gly 230 | Thr | Asp | Ile | Val | Ala 235 | Thr | Val | Glu | Asn | Glu 240 |
| Lys | Pro | Ser | Pro | Cys 245 | Ala | Arg | Thr | Gly | Ser 250 | Gly | Arg | Pro | Cys | Thr 255 | Ile |
| Asn | Gly | Ser | Glu 260 | Cys | Arg | Gly | Gly | Trp 265 | Pro | Gly | Pro | Asn | His 270 | Gly | Ile |
| Thr | His | Phe 275 | Asp | Asn | Phe | Gly | Phe 280 | Ser | Met | Leu | Thr | Val 285 | Tyr | Gln | Cys |
| Ile | Thr 290 | Met | Glu | Gly | Trp | Thr 295 | Asp | Val | Leu | Tyr | Trp 300 | Val | Asn | Asp | Ala |
| Ile 305 | Gly | Asn | Glu | Trp | Pro 310 | Trp | Ile | Tyr | Phe | Val 315 | Thr | Leu | Ile | Leu | Leu 320 |
| Gly | Ser | Phe | Phe | Ile 325 | Leu | Asn | Leu | Val | Leu 330 | Gly | Val | Leu | Ser | Gly 335 | Glu |
| Phe | Thr | Lys | Glu 340 | Arg | Glu | Lys | Ala | Lys 345 | Ser | Arg | Gly | Thr | Phe 350 | Gln | Lys |
| Leu | Arg | Glu 355 | Lys | Gln | Gln | Leu | Glu 360 | Glu | Asp | Leu | Arg | Gly 365 | Tyr | Met | Ser |
| Trp | Ile 370 | Thr | Gln | Gly | Glu | Val 375 | Met | Asp | Val | Glu | Asp 380 | Leu | Arg | Glu | Gly |
| Lys 385 | Leu | Ser | Leu | Glu | Glu 390 | Gly | Gly | Ser | Asp | Thr 395 | Glu | Ser | Leu | Tyr | Glu 400 |
| Ile | Glu | Gly | Leu | Asn 405 | Lys | Ile | Ile | Gln | Phe 410 | Ile | Arg | His | Trp | Arg 415 | Gln |
| Trp | Asn | Arg | Val 420 | Phe | Arg | Trp | Lys | Cys 425 | His | Asp | Leu | Val | Lys 430 | Ser | Arg |
| Val | Phe | Tyr 435 | Trp | Leu | Val | Ile | Leu 440 | Ile | Val | Ala | Leu | Asn 445 | Thr | Leu | Ser |
| Ile | Ala 450 | Ser | Glu | His | His | Asn 455 | Gln | Pro | Leu | Trp | Leu 460 | Thr | His | Leu | Gln |
| Asp 465 | Thr | Ala | Asn | Arg | Val 470 | Leu | Leu | Ser | Leu | Phe 475 | Thr | Ile | Glu | Met | Leu 480 |

```
Leu Lys Met Tyr Gly Leu Gly Leu Arg Gln Tyr Phe Met Ser Ile Phe
            485             490             495
Asn Arg Phe Asp Cys Phe Val Val Cys Ser Gly Ile Leu Glu Leu Leu
            500             505             510
Leu Val Glu Ser Gly Ala Met Thr Pro Leu Gly Ile Ser Val Leu Arg
            515             520             525
Cys Ile Arg Leu Leu Arg Leu Phe Lys Ile Thr Lys Tyr Trp Thr Ser
    530             535             540
Leu Ser Asn Leu Val Ala Ser Leu Leu Asn Ser Ile Arg Ser Ile Ala
545             550             555             560
Ser Leu Leu Leu Leu Leu Phe Leu Phe Ile Ile Ile Phe Ala Leu Leu
                565             570             575
Gly Ile Gln Leu Phe Gly Gly Arg Tyr Asp Phe Glu Asp Thr Glu Val
            580             585             590
Arg Arg Ser Asn Phe Asp Asn Phe Pro Gln Ala Leu Ile Ser Val Phe
        595             600             605
Gln Val Leu Thr Gly Glu Asp Trp Asn Ser Val Met Tyr Asn Gly Ile
    610             615             620
Met Ala Tyr Gly Gly Pro Ser Tyr Pro Gly Val Leu Val Cys Ile Tyr
625             630             635             640
Phe Ile Ile Leu Phe Val Cys Gly Asn Tyr Ile Leu Leu Asn Val Phe
                645             650             655
Leu Ala Ile Ala Val Asp Asn Leu Ala Glu Ala Glu Ser Leu Thr Ser
            660             665             670
Ala Gln Lys Ala Lys Ala Glu Glu Arg Lys Arg Arg Lys Met Ser Arg
    675             680             685
Gly Leu Pro Asp Lys Thr Glu Glu Lys Ser Val Met Ala Lys Lys
690             695             700
Leu Glu Gln Lys Pro Lys Gly Glu Gly Ile Pro Thr Thr Ala Lys Leu
705             710             715             720
Lys Val Asp Glu Phe Glu Ser Asn Val Asn Glu Val Lys Asp Pro Tyr
            725             730             735
Pro Ser Ala Asp Phe Pro Gly Asp Asp Glu Glu Asp Glu Pro Glu Ile
            740             745             750
Pro Val Ser Pro Arg Pro Arg Pro Leu Ala Glu Leu Gln Leu Lys Glu
            755             760             765
Lys Ala Val Pro Ile Pro Glu Ala Ser Ser Phe Phe Ile Phe Ser Pro
            770             775             780
Thr Asn Lys Val Arg Val Leu Cys His Arg Ile Val Asn Ala Thr Trp
785             790             795             800
Phe Thr Asn Phe Ile Leu Leu Phe Ile Leu Leu Ser Ser Ala Ala Leu
                805             810             815
Ala Ala Glu Asp Pro Ile Arg Ala Glu Ser Val Arg Asn Gln Ile Leu
            820             825             830
Gly Tyr Phe Asp Ile Ala Phe Thr Ser Val Phe Thr Val Glu Ile Val
            835             840             845
Leu Lys Met Thr Thr Tyr Gly Ala Phe Leu His Lys Gly Ser Phe Cys
    850             855             860
Arg Asn Tyr Phe Asn Ile Leu Asp Leu Leu Val Val Ala Val Ser Leu
865             870             875             880
Ile Ser Met Gly Leu Glu Ser Ser Thr Ile Ser Val Val Lys Ile Leu
            885             890             895
Arg Val Leu Arg Val Leu Arg Pro Leu Arg Ala Ile Asn Arg Ala Lys
```

```
                    900                      905                       910
Gly Leu Lys His Val Val Gln Cys Val Phe Val Ala Ile Arg Thr Ile
        915                 920                 925
Gly Asn Ile Val Leu Val Thr Thr Leu Leu Gln Phe Met Phe Ala Cys
        930                 935                 940
Ile Gly Val Gln Leu Phe Lys Gly Lys Phe Phe Ser Cys Asn Asp Leu
945                 950                 955                     960
Ser Lys Met Thr Glu Glu Cys Arg Gly Tyr Tyr Tyr Val Tyr Lys
                965                 970                 975
Asp Gly Asp Pro Thr Gln Met Glu Leu Arg Pro Arg Gln Trp Ile His
            980                 985                 990
Asn Asp Phe His Phe Asp Asn Val Leu Ser Ala Met Met Ser Leu Phe
            995                 1000                1005
Thr Val Ser Thr Phe Glu Gly Trp Pro Gln Leu Leu Tyr Arg Ala Ile
        1010                1015                1020
Asp Ser Asn Glu Glu Asp Met Gly Pro Val Tyr Asn Asn Arg Val Glu
1025                1030                1035                    1040
Met Ala Ile Phe Phe Ile Ile Tyr Ile Ile Leu Ile Ala Phe Phe Met
                1045                1050                1055
Met Asn Ile Phe Val Gly Phe Val Ile Val Thr Phe Gln Glu Gln Gly
                1060                1065                1070
Glu Thr Glu Tyr Lys Asn Cys Glu Leu Asp Lys Asn Gln Arg Gln Cys
        1075                1080                1085
Val Gln Tyr Ala Leu Lys Ala Arg Pro Leu Arg Ser Tyr Ile Pro Lys
        1090                1095                1100
Asn Pro Tyr Gln Tyr Gln Val Trp Tyr Val Val Thr Ser Ser Tyr Phe
1105                1110                1115                    1120
Glu Tyr Leu Met Phe Ala Leu Ile Met Leu Asn Thr Ile Cys Leu Gly
                1125                1130                1135
Met Gln His Tyr His Gln Ser Glu Glu Met Asn His Ile Ser Asp Ile
                1140                1145                1150
Leu Asn Val Ala Phe Thr Ile Ile Phe Thr Leu Glu Met Ile Leu Lys
        1155                1160                1165
Leu Leu Ala Phe Lys Ala Arg Gly Tyr Phe Gly Asp Pro Trp Asn Val
        1170                1175                1180
Phe Asp Phe Leu Ile Val Ile Arg Ser Ile Ile Asp Val Ile Leu Ser
1185                1190                1195                    1200
Glu Thr Asp Thr Phe Leu Ala Ser Ser Gly Gly Leu Tyr Cys Leu Gly
                1205                1210                1215
Gly Gly Cys Gly Asn Val Asp Pro Asp Glu Ser Ala Arg Ile Ser Ser
            1220                1225                1230
Ala Phe Phe Arg Leu Phe Arg Val Met Arg Leu Ile Lys Leu Leu Ser
        1235                1240                1245
Arg Ala Glu Gly Val Arg Thr Leu Leu Trp Thr Phe Ile Lys Ser Phe
        1250                1255                1260
Gln Ala Leu Pro Tyr Val Ala Leu Leu Ile Val Met Leu Phe Phe Ile
1265                1270                1275                    1280
Tyr Ala Val Ile Gly Met Gln Met Phe Gly Lys Ile Ala Leu Val Asp
                1285                1290                1295
Gly Thr Gln Ile Asn Arg Asn Asn Asn Phe Gln Thr Phe Pro Gln Ala
            1300                1305                1310
Val Leu Leu Leu Phe Arg Cys Ala Thr Gly Glu Ala Trp Gln Glu Ile
        1315                1320                1325
```

```
Leu Leu Ala Cys Ser Tyr Gly Lys Leu Cys Asp Pro Glu Ser Asp Tyr
    1330            1335                1340
Ala Pro Gly Glu Glu Tyr Thr Cys Gly Thr Asn Phe Ala Tyr Tyr Tyr
1345             1350                1355                1360
Phe Ile Ser Phe Tyr Met Leu Cys Ala Phe Leu Ile Ile Asn Leu Phe
            1365                1370                1375
Val Ala Val Ile Met Asp Asn Phe Asp Tyr Leu Thr Arg Asp Trp Ser
        1380                1385                1390
Ile Leu Gly Pro His His Leu Asp Glu Phe Lys Ala Ile Trp Ala Glu
        1395            1400                1405
Tyr Asp Pro Glu Ala Lys Gly Arg Ile Lys His Leu Asp Val Val Thr
    1410            1415                1420
Leu Leu Arg Arg Ile Gln Pro Pro Leu Gly Phe Gly Lys Phe Cys Pro
1425            1430            1435                1440
His Arg Val Ala Cys Lys Arg Leu Val Gly Met Asn Met Pro Leu Asn
            1445            1450                1455
Ser Asp Gly Thr Val Thr Phe Asn Ala Thr Leu Phe Ala Leu Val Arg
        1460            1465                1470
Thr Ala Leu Lys Ile Lys Thr Glu Gly Asn Phe Glu Gln Ala Asn Glu
    1475            1480                1485
Glu Leu Arg Ala Ile Ile Lys Lys Ile Trp Lys Arg Thr Ser Met Lys
    1490                1495            1500
Leu Leu Asp Gln Val Ile Pro Pro Ile Gly Asp Asp Glu Val Thr Val
1505            1510            1515                1520
Gly Lys Phe Tyr Ala Thr Phe Leu Ile Gln Glu His Phe Arg Lys Phe
        1525            1530                1535
Met Lys Arg Gln Glu Glu Tyr Tyr Gly Tyr Arg Pro Lys Lys Asp Thr
        1540            1545                1550
Val Gln Ile Gln Ala Gly Leu Arg Thr Ile Glu Glu Glu Ala Ala Pro
    1555            1560                1565
Glu Ile Arg Arg Thr Ile Ser Gly Asp Leu Thr Ala Glu Glu Glu Leu
    1570            1575            1580
Glu Arg Ala Met Val Glu Ala Ala Met Glu Glu Arg Ile Phe Arg Arg
1585            1590            1595                1600
Thr Gly Gly Leu Phe Gly Gln Val Asp Thr Phe Leu Glu Arg Thr Asn
            1605            1610                1615
Ser Leu Pro Pro Val Met Ala Asn Gln Arg Pro Leu Gln Phe Ala Glu
        1620            1625                1630
Ile Glu Met Glu Glu Leu Glu Ser Pro Val Phe Leu Glu Asp Phe Pro
        1635            1640                1645
Gln Asp Ala Arg Thr Asn Pro Leu Ala Arg Ala Asn Thr Asn Asn Ala
    1650            1655            1660
Asn Ala Asn Val Ala Tyr Gly Asn Ser Asn His Ser Asn Asn Gln Met
1665            1670            1675                1680
Phe Ser Ser Val His Cys Glu Arg Glu Phe Pro Gly Glu Ala Glu Thr
            1685            1690                1695
Pro Ala Ala Gly Arg Gly Ala Leu Ser His Ser His Arg Ala Leu Gly
            1700            1705                1710
Pro His Ser Lys Pro Cys Ala Gly Lys Leu Asn Gly Gln Leu Val Gln
    1715            1720                1725
Pro Gly Met Pro Ile Asn Gln Ala Pro Pro Ala Pro Cys Gln Gln Pro
        1730            1735            1740
Ser Thr Asp Pro Pro Glu Arg Gly Gln Arg Arg Thr Ser Leu Thr Gly
1745            1750            1755                1760
```

```
Ser  Leu  Gln  Asp  Glu  Ala  Pro  Gln  Arg  Arg  Ser  Ser  Glu  Gly  Ser  Thr
              1765                1770                1775

Pro  Arg  Arg  Pro  Ala  Pro  Ala  Thr  Ala  Leu  Leu  Ile  Gln  Glu  Ala  Leu
         1780                1785                1790

Val  Arg  Gly  Gly  Leu  Asp  Thr  Leu  Ala  Ala  Asp  Ala  Gly  Phe  Val  Met
         1795                1800                1805

Ala  Thr  Ser  Gln  Ala  Leu  Val  Asp  Ala  Cys  Gln  Met  Glu  Pro  Glu  Glu
    1810                1815                1820

Val  Glu  Val  Ala  Ala  Thr  Glu  Leu  Leu  Lys  Glu  Arg  Glu  Ser  Val  Gln
1825                1830                1835                          1840

Gly  Met  Ala  Ser  Val  Pro  Gly  Ser  Leu  Ser  Arg  Arg  Ser  Ser  Leu  Gly
              1845                1850                          1855

Ser  Leu  Asp  Gln  Val  Gln  Gly  Ser  Gln  Glu  Thr  Leu  Ile  Pro  Pro  Arg
              1860                1865                1870

Pro
```

(2) INFORMATION FOR SEQ ID NO:8:

(i) SEQUENCE CHARACTERISTICS:
        (A) LENGTH: 1106 amino acids
        (B) TYPE: amino acid
        (C) STRANDEDNESS: single
        (D) TOPOLOGY: linear (ii) MOLECULE TYPE: protein (v) FRAGMENT TYPE: internal (vi) ORIGINAL SOURCE:

(xi) SEQUENCE DESCRIPTION: SEQ ID NO:8:

```
Met  Ala  Ala  Gly  Arg  Pro  Leu  Ala  Trp  Thr  Leu  Thr  Leu  Trp  Gln  Ala
 1             5                  10                      15

Trp  Leu  Ile  Leu  Ile  Gly  Pro  Ser  Ser  Glu  Glu  Pro  Phe  Pro  Ser  Ala
              20                  25                      30

Val  Thr  Ile  Lys  Ser  Trp  Val  Asp  Lys  Met  Gln  Glu  Asp  Leu  Val  Thr
              35                  40                      45

Leu  Ala  Lys  Thr  Ala  Ser  Gly  Val  His  Gln  Leu  Val  Asp  Ile  Tyr  Glu
    50                  55                      60

Lys  Tyr  Gln  Asp  Leu  Tyr  Thr  Val  Glu  Pro  Asn  Asn  Ala  Arg  Gln  Leu
65                  70                      75                          80

Val  Glu  Ile  Ala  Ala  Arg  Asp  Ile  Glu  Lys  Leu  Leu  Ser  Asn  Arg  Ser
              85                  90                      95

Lys  Ala  Leu  Val  Arg  Leu  Ala  Leu  Glu  Ala  Glu  Lys  Val  Gln  Ala  Ala
              100                 105                     110

His  Gln  Trp  Arg  Glu  Asp  Phe  Ala  Ser  Asn  Glu  Val  Val  Tyr  Tyr  Asn
              115                 120                     125

Ala  Lys  Asp  Asp  Leu  Asp  Pro  Glu  Lys  Asn  Glu  Ser  Glu  Pro  Gly  Ser
    130                 135                     140

Gln  Arg  Ile  Lys  Pro  Val  Phe  Ile  Asp  Asp  Ala  Asn  Phe  Arg  Arg  Gln
145                 150                     155                         160

Val  Ser  Tyr  Gln  His  Ala  Ala  Val  His  Ile  Pro  Thr  Asp  Ile  Tyr  Glu
              165                 170                     175

Gly  Ser  Thr  Ile  Val  Leu  Asn  Glu  Leu  Asn  Trp  Thr  Ser  Ala  Leu  Asp
              180                 185                     190

Asp  Val  Phe  Lys  Lys  Asn  Arg  Glu  Glu  Asp  Pro  Ser  Leu  Leu  Trp  Gln
              195                 200                     205
```

-continued

| | | | | | | | | | | | | | | |
|---|---|---|---|---|---|---|---|---|---|---|---|---|---|---|
| Val | Phe | Gly | Ser | Ala | Thr | Gly | Leu | Ala | Arg | Tyr | Tyr | Pro | Ala | Ser | Pro |
| 210 | | | | | 215 | | | | | 220 | | | | | |
| Trp | Val | Asp | Asn | Ser | Arg | Thr | Pro | Asn | Lys | Ile | Asp | Leu | Tyr | Asp | Val |
| 225 | | | | | 230 | | | | | 235 | | | | | 240 |
| Arg | Arg | Arg | Pro | Trp | Tyr | Ile | Gln | Gly | Ala | Ala | Ser | Pro | Lys | Asp | Met |
| | | | | 245 | | | | | 250 | | | | | 255 | |
| Leu | Ile | Leu | Val | Asp | Val | Ser | Gly | Ser | Val | Ser | Gly | Leu | Thr | Leu | Lys |
| | | | 260 | | | | | 265 | | | | 270 | | | |
| Leu | Ile | Arg | Thr | Ser | Val | Ser | Glu | Met | Leu | Glu | Thr | Leu | Ser | Asp | Asp |
| | | 275 | | | | | 280 | | | | | 285 | | | |
| Asp | Phe | Val | Asn | Val | Ala | Ser | Phe | Asn | Ser | Asn | Ala | Gln | Asp | Val | Ser |
| | 290 | | | | | 295 | | | | | 300 | | | | |
| Cys | Phe | Gln | His | Leu | Val | Gln | Ala | Asn | Val | Arg | Asn | Lys | Lys | Val | Leu |
| 305 | | | | | 310 | | | | | 315 | | | | | 320 |
| Lys | Asp | Ala | Val | Asn | Asn | Ile | Thr | Ala | Lys | Gly | Ile | Thr | Asp | Tyr | Lys |
| | | | | 325 | | | | | 330 | | | | | 335 | |
| Lys | Gly | Phe | Ser | Phe | Ala | Phe | Glu | Gln | Leu | Leu | Asn | Tyr | Asn | Val | Ser |
| | | | 340 | | | | | 345 | | | | 350 | | | |
| Arg | Ala | Asn | Cys | Asn | Lys | Ile | Ile | Met | Leu | Phe | Thr | Asp | Gly | Gly | Glu |
| | | 355 | | | | | 360 | | | | | 365 | | | |
| Glu | Arg | Ala | Gln | Glu | Ile | Phe | Ala | Lys | Tyr | Asn | Lys | Asp | Lys | Lys | Val |
| | 370 | | | | | 375 | | | | | 380 | | | | |
| Arg | Val | Phe | Thr | Phe | Ser | Val | Gly | Gln | His | Asn | Tyr | Asp | Arg | Gly | Pro |
| 385 | | | | | 390 | | | | | 395 | | | | | 400 |
| Ile | Gln | Trp | Met | Ala | Cys | Glu | Asn | Lys | Gly | Tyr | Tyr | Tyr | Glu | Ile | Pro |
| | | | | 405 | | | | | 410 | | | | | 415 | |
| Ser | Ile | Gly | Ala | Ile | Arg | Ile | Asn | Thr | Gln | Glu | Tyr | Leu | Asp | Val | Leu |
| | | | 420 | | | | | 425 | | | | 430 | | | |
| Gly | Arg | Pro | Met | Val | Leu | Ala | Gly | Asp | Lys | Ala | Lys | Gln | Val | Gln | Trp |
| | | 435 | | | | | 440 | | | | | 445 | | | |
| Thr | Asn | Val | Tyr | Leu | Asp | Ala | Leu | Glu | Leu | Gly | Leu | Val | Ile | Thr | Gly |
| | 450 | | | | | 455 | | | | | 460 | | | | |
| Thr | Leu | Pro | Val | Phe | Asn | Ile | Thr | Gly | Gln | Phe | Glu | Asn | Lys | Thr | Asn |
| 465 | | | | | 470 | | | | | 475 | | | | | 480 |
| Leu | Lys | Asn | Gln | Leu | Ile | Leu | Gly | Val | Met | Gly | Val | Asp | Val | Ser | Leu |
| | | | | 485 | | | | | 490 | | | | | 495 | |
| Glu | Asp | Ile | Lys | Arg | Leu | Thr | Pro | Arg | Phe | Thr | Leu | Cys | Pro | Asn | Gly |
| | | | 500 | | | | | 505 | | | | 510 | | | |
| Tyr | Tyr | Phe | Ala | Ile | Asp | Pro | Asn | Gly | Tyr | Val | Leu | Leu | His | Pro | Asn |
| | | 515 | | | | | 520 | | | | | 525 | | | |
| Leu | Gln | Pro | Lys | Pro | Ile | Gly | Val | Gly | Ile | Pro | Thr | Ile | Asn | Leu | Arg |
| | 530 | | | | | 535 | | | | | 540 | | | | |
| Lys | Arg | Arg | Pro | Asn | Val | Gln | Asn | Pro | Lys | Ser | Gln | Glu | Pro | Val | Thr |
| 545 | | | | | 550 | | | | | 555 | | | | | 560 |
| Leu | Asp | Phe | Leu | Asp | Ala | Glu | Leu | Glu | Asn | Asp | Ile | Lys | Val | Glu | Ile |
| | | | | 565 | | | | | 570 | | | | | 575 | |
| Arg | Asn | Lys | Met | Ile | Asp | Gly | Glu | Ser | Gly | Glu | Lys | Thr | Phe | Arg | Thr |
| | | | 580 | | | | | 585 | | | | 590 | | | |
| Leu | Val | Lys | Ser | Gln | Asp | Glu | Arg | Tyr | Ile | Asp | Lys | Gly | Asn | Arg | Thr |
| | | 595 | | | | | 600 | | | | | 605 | | | |
| Tyr | Thr | Trp | Thr | Pro | Val | Asn | Gly | Thr | Asp | Tyr | Ser | Ser | Leu | Ala | Leu |
| | 610 | | | | | 615 | | | | | 620 | | | | |
| Val | Leu | Pro | Thr | Tyr | Ser | Phe | Tyr | Tyr | Ile | Lys | Ala | Lys | Ile | Glu | Glu |
| 625 | | | | | 630 | | | | | 635 | | | | | 640 |

```
Thr  Ile  Thr  Gln  Ala  Arg  Tyr  Ser  Glu  Thr  Leu  Lys  Pro  Asp  Asn  Phe
               645                      650                      655

Glu  Glu  Ser  Gly  Tyr  Thr  Phe  Leu  Ala  Pro  Arg  Asp  Tyr  Cys  Ser  Asp
          660                      665                      670

Leu  Lys  Pro  Ser  Asp  Asn  Thr  Glu  Phe  Leu  Leu  Asn  Phe  Asn  Glu
          675                      680                      685

Phe  Ile  Asp  Arg  Lys  Thr  Pro  Asn  Asn  Pro  Ser  Cys  Asn  Thr  Asp  Leu
     690                      695                      700

Ile  Asn  Arg  Val  Leu  Leu  Asp  Ala  Gly  Phe  Thr  Asn  Glu  Leu  Val  Gln
705                      710                      715                      720

Asn  Tyr  Trp  Ser  Lys  Gln  Lys  Asn  Ile  Lys  Gly  Val  Lys  Ala  Arg  Phe
                    725                      730                      735

Val  Val  Thr  Asp  Gly  Gly  Ile  Thr  Arg  Val  Tyr  Pro  Lys  Glu  Ala  Gly
               740                      745                      750

Glu  Asn  Trp  Gln  Glu  Asn  Pro  Glu  Thr  Tyr  Glu  Asp  Ser  Phe  Tyr  Lys
          755                      760                      765

Arg  Ser  Leu  Asp  Asn  Asp  Asn  Tyr  Val  Phe  Thr  Ala  Pro  Tyr  Phe  Asn
     770                      775                      780

Lys  Ser  Gly  Pro  Gly  Ala  Tyr  Glu  Ser  Gly  Ile  Met  Val  Ser  Lys  Ala
785                      790                      795                      800

Val  Glu  Ile  Tyr  Ile  Gln  Gly  Lys  Leu  Leu  Lys  Pro  Ala  Val  Val  Gly
               805                      810                      815

Ile  Lys  Ile  Asp  Val  Asn  Ser  Trp  Ile  Glu  Asn  Phe  Thr  Lys  Thr  Ser
               820                      825                      830

Ile  Arg  Asp  Pro  Cys  Ala  Gly  Pro  Val  Cys  Asp  Cys  Lys  Arg  Asn  Ser
          835                      840                      845

Asp  Val  Met  Asp  Cys  Val  Ile  Leu  Asp  Asp  Gly  Gly  Phe  Leu  Leu  Met
     850                      855                      860

Ala  Asn  His  Asp  Asp  Tyr  Thr  Asn  Gln  Ile  Gly  Arg  Phe  Phe  Gly  Glu
865                      870                      875                      880

Ile  Asp  Pro  Ser  Leu  Met  Arg  His  Leu  Val  Asn  Ile  Ser  Val  Tyr  Ala
               885                      890                      895

Phe  Asn  Lys  Ser  Tyr  Asp  Tyr  Gln  Ser  Val  Cys  Glu  Pro  Gly  Ala  Ala
               900                      905                      910

Pro  Asn  Gln  Gly  Ala  Gly  His  Arg  Ser  Ala  Tyr  Val  Pro  Ser  Ile  Ala
          915                      920                      925

Asp  Ile  Leu  Gln  Ile  Gly  Trp  Trp  Ala  Thr  Ala  Ala  Ala  Trp  Ser  Ile
     930                      935                      940

Leu  Gln  Gln  Phe  Leu  Leu  Ser  Leu  Thr  Phe  Pro  Arg  Leu  Leu  Glu  Ala
945                      950                      955                      960

Ala  Asp  Met  Glu  Asp  Asp  Asp  Phe  Thr  Ala  Ser  Met  Ser  Lys  Gln  Ser
               965                      970                      975

Cys  Ile  Thr  Glu  Gln  Thr  Gln  Tyr  Phe  Phe  Asp  Asn  Asp  Ser  Lys  Ser
               980                      985                      990

Phe  Ser  Gly  Val  Leu  Asp  Cys  Gly  Asn  Cys  Ser  Arg  Ile  Phe  His  Val
          995                      1000                     1005

Glu  Lys  Leu  Ile  Asn  Thr  Asn  Leu  Ile  Phe  Ile  Met  Val  Glu  Ser  Lys
     1010                     1015                     1020

Gly  Thr  Cys  Pro  Cys  Asp  Thr  Arg  Leu  Leu  Ile  Gln  Ala  Glu  Gln  Thr
1025                     1030                     1035                     1040

Ser  Asp  Gly  Pro  Asp  Pro  Cys  Asp  Met  Val  Lys  Gln  Pro  Arg  Tyr  Arg
               1045                     1050                     1055

Lys  Gly  Pro  Asp  Val  Cys  Phe  Asp  Asn  Asn  Val  Leu  Glu  Asp  Tyr  Thr
```

|  | 1060 | | | | 1065 | | | | | 1070 | | | |
|---|---|---|---|---|---|---|---|---|---|---|---|---|---|
| Asp | Cys | Gly | Gly | Val | Ser | Gly | Leu | Asn | Pro | Ser | Leu | Trp | Ser | Ile Ile |
| | | 1075 | | | | 1080 | | | | | 1085 | | | |
| Gly | Ile | Gln | Phe | Val | Leu | Leu | Trp | Leu | Val | Ser | Gly | Ser | Arg | His Cys |
| | | 1090 | | | | 1095 | | | | | 1100 | | | |
| Leu | Leu | | | | | | | | | | | | | |
| 1105 | | | | | | | | | | | | | | |